(12) United States Patent
Simmons

(10) Patent No.: US 12,239,152 B2
(45) Date of Patent: Mar. 4, 2025

(54) COMPOSITIONS, THEIR USE, AND METHODS FOR THEIR FORMATION

(71) Applicant: Cambridge Glycoscience Ltd, Cambridge (GB)

(72) Inventor: Thomas J. Simmons, Cambridge (GB)

(73) Assignee: CAMBRIDGE GLYCOSCIENCE LTD, Cambridge (GB)

( * ) Notice: Subject to any disclaimer, the term of this patent is extended or adjusted under 35 U.S.C. 154(b) by 0 days.

(21) Appl. No.: 18/465,833

(22) Filed: Sep. 12, 2023

(65) Prior Publication Data

US 2024/0180216 A1 Jun. 6, 2024

Related U.S. Application Data

(63) Continuation of application No. 17/229,628, filed on Apr. 13, 2021, now Pat. No. 11,903,399, which is a continuation of application No. 16/844,960, filed on Apr. 9, 2020, now Pat. No. 11,006,658, which is a continuation of application No. PCT/EP2019/072026, filed on Aug. 16, 2019.

(60) Provisional application No. 62/764,660, filed on Aug. 15, 2018.

(51) Int. Cl.
- A23L 27/30 (2016.01)
- A23L 29/30 (2016.01)
- A23L 33/24 (2016.01)

(52) U.S. Cl.
CPC .............. *A23L 27/33* (2016.08); *A23L 29/30* (2016.08); *A23L 33/24* (2016.08); *A23V 2002/00* (2013.01)

(58) Field of Classification Search
None
See application file for complete search history.

(56) References Cited

U.S. PATENT DOCUMENTS

| | | |
|---|---|---|
| 4,927,646 A | 5/1990 | Jenner et al. |
| 6,667,066 B2 | 12/2003 | Labeille et al. |
| 7,033,626 B2 | 4/2006 | Spendler et al. |
| 7,151,079 B2 | 12/2006 | Fack et al. |
| 7,378,103 B2 | 5/2008 | Kanji et al. |
| 7,598,069 B2 | 10/2009 | Felby et al. |
| 7,754,456 B2 | 7/2010 | Penttila et al. |
| 7,993,463 B2 | 8/2011 | Griffin et al. |
| 7,993,890 B2 | 8/2011 | Soerensen et al. |
| 8,057,840 B2 | 11/2011 | Harrison et al. |
| 8,202,842 B2 | 6/2012 | Sinclair et al. |
| 8,247,200 B2 | 8/2012 | Foody et al. |
| 8,663,952 B2 | 3/2014 | He et al. |
| 8,679,794 B2 | 3/2014 | Muniglia et al. |
| 8,709,763 B2 | 4/2014 | Lali et al. |
| 8,894,771 B2 | 11/2014 | Floyd et al. |
| 8,927,038 B2 | 1/2015 | Broekaert et al. |
| 8,956,846 B2 | 2/2015 | Ben Chaabane et al. |
| 9,062,328 B2 | 6/2015 | Medoff |
| 9,090,916 B2 | 7/2015 | Casanave et al. |
| 9,113,652 B2 | 8/2015 | Pilling et al. |
| 9,150,895 B2 | 10/2015 | Kurihara et al. |
| 9,410,216 B2 | 8/2016 | Eyal et al. |
| 9,458,482 B2 | 10/2016 | Bals et al. |
| 9,580,729 B2 | 2/2017 | Noda et al. |
| 9,605,291 B2 | 3/2017 | Yamada et al. |
| 9,663,836 B2 | 5/2017 | Jansen et al. |
| 9,670,516 B2 | 6/2017 | Minamino et al. |
| 9,783,860 B2 | 10/2017 | Floyd et al. |
| 9,797,021 B2 | 10/2017 | Floyd et al. |
| 9,920,309 B2 | 3/2018 | Reisinger et al. |
| 9,920,346 B2 | 3/2018 | Funada et al. |
| 9,955,707 B2 | 5/2018 | Delbaere |
| 9,963,725 B2 | 5/2018 | Lali et al. |
| 9,963,728 B2 | 5/2018 | Minamino et al. |
| 9,982,280 B2 | 5/2018 | Noordam et al. |
| 9,988,657 B2 | 6/2018 | Nagy et al. |
| 10,041,138 B1 | 8/2018 | Eyal et al. |
| 10,131,923 B2 | 11/2018 | Noordam et al. |
| 10,167,576 B2 | 1/2019 | Chao et al. |
| 10,174,351 B2 | 1/2019 | Smits et al. |
| 10,253,343 B2 | 4/2019 | Yamada et al. |
| 10,351,633 B2 | 7/2019 | Cheng et al. |
| 10,368,569 B2 | 8/2019 | Toksoz et al. |
| 10,426,791 B2 | 10/2019 | Speelmans et al. |
| 10,428,362 B2 | 10/2019 | Nagy et al. |
| 10,472,657 B2 | 11/2019 | Nagy et al. |
| 10,487,369 B2 | 11/2019 | Floyd et al. |
| 10,557,153 B2 | 2/2020 | De et al. |

(Continued)

FOREIGN PATENT DOCUMENTS

| | | |
|---|---|---|
| CA | 2831543 A1 | 10/2012 |
| CN | 1482868 A | 3/2004 |

(Continued)

OTHER PUBLICATIONS

Aachary et al. Xylooligosaccharides (XOS) as an Emerging Prebiotic: Microbial Synthesis, Utilization, Structural Characterization, Bioactive Properties, and Applications. Comprehensive Reviews in Food Science and Food Safety, vol. 10, pp. 2-16 (2011).

Basholli-Salihu et al. The Use of Cellobiose and Fructooligosaccharide on Growth and Stability of Bifidobacterium infantis in Fermented Milk. Food and Nutrition Sciences, 2013, 4, 1301-1306. Published Online Dec. 2013. DOI: http://dx.doi.org/10.4236/fns.2013.412167.

Beldman et al. Application of cellulase and pectinase from fungal origin for the liquefaction and saccharification of biomass. Enzyme and Microbial Technology, vol. 6, Issue 11, pp. 503-507 (Nov. 1984). DOI: https://doi.org/10.1016/0141-0229(84)90004-8.

(Continued)

*Primary Examiner* — Jyoti Chawla
(74) *Attorney, Agent, or Firm* — Wilson Sonsini Goodrich & Rosati

(57) ABSTRACT

Compositions comprising polysaccharides and oligosaccharides are provided. Methods for the formation of the compositions, including the enzymatic production of the oligosaccharides, and the uses of the compositions in foodstuffs, cosmetics, and nutraceuticals are also provided.

20 Claims, 13 Drawing Sheets

Specification includes a Sequence Listing.

(56) References Cited

U.S. PATENT DOCUMENTS

| | | | |
|---|---|---|---|
| 10,563,238 B2 | 2/2020 | Yamada et al. |
| 10,570,432 B2 | 2/2020 | Nishino et al. |
| 10,633,461 B2 | 4/2020 | Richard et al. |
| 10,752,705 B2 | 8/2020 | Geremia et al. |
| 10,858,712 B2 | 12/2020 | Kilambi et al. |
| 11,006,658 B2 | 5/2021 | Simmons |
| 11,134,709 B2 | 10/2021 | Hofmekler |
| 11,151,848 B2 | 10/2021 | Strong et al. |
| 11,180,786 B2 | 11/2021 | Cao et al. |
| 11,193,005 B2 | 12/2021 | Behabtu |
| 11,208,674 B2 | 12/2021 | Konishi et al. |
| 11,248,247 B2 | 2/2022 | Simmons |
| 11,253,818 B2 | 2/2022 | Kurihara et al. |
| 11,254,957 B2 | 2/2022 | Retsina et al. |
| 11,279,960 B2 | 3/2022 | Kasahara et al. |
| 11,297,865 B2 | 4/2022 | Simmons et al. |
| 11,596,165 B2 | 3/2023 | Simmons |
| 11,771,123 B2 | 10/2023 | Simmons et al. |
| 11,871,763 B2 | 1/2024 | Simmons |
| 11,903,399 B2 | 2/2024 | Simmons |
| 2003/0091691 A1 | 5/2003 | Olsen et al. |
| 2004/0258829 A1 | 12/2004 | Zheng et al. |
| 2007/0248649 A1 | 10/2007 | Sawatzki et al. |
| 2008/0102163 A1 | 5/2008 | O'Toole et al. |
| 2009/0042266 A1 | 2/2009 | Vehmaanpera et al. |
| 2009/0062232 A1 | 3/2009 | Fujikawa et al. |
| 2009/0232892 A1 | 9/2009 | Yamasaki et al. |
| 2009/0305935 A1 | 12/2009 | Cascao-Pereira et al. |
| 2011/0143402 A1 | 6/2011 | De Laat et al. |
| 2011/0171710 A1 | 7/2011 | Yu et al. |
| 2012/0035127 A1 | 2/2012 | Goffin et al. |
| 2012/0115192 A1 | 5/2012 | Lali et al. |
| 2012/0135500 A1 | 5/2012 | Aehle et al. |
| 2012/0231147 A1 | 9/2012 | Srinivasan et al. |
| 2012/0264873 A1 | 10/2012 | Eyal et al. |
| 2013/0095531 A1 | 4/2013 | Schooneveld-Bergmans et al. |
| 2013/0157318 A1 | 6/2013 | Ishikawa et al. |
| 2013/0164420 A1 | 6/2013 | Catani et al. |
| 2014/0030381 A1 | 1/2014 | Markysyan |
| 2015/0065454 A1 | 3/2015 | Dupasquier et al. |
| 2016/0007642 A1 | 1/2016 | Geremia et al. |
| 2016/0081381 A1 | 3/2016 | Medoff |
| 2016/0082022 A1 | 3/2016 | Medoff |
| 2016/0208300 A1 | 7/2016 | Yamada et al. |
| 2016/0235098 A1 | 8/2016 | Cox |
| 2016/0326559 A1 | 11/2016 | Funada et al. |
| 2016/0340705 A1 | 11/2016 | Lali et al. |
| 2017/0114371 A1 | 4/2017 | Pedersen et al. |
| 2017/0295805 A1 | 10/2017 | Abu-Hardan et al. |
| 2017/0303548 A1 | 10/2017 | Krogh et al. |
| 2017/0303550 A1 | 10/2017 | Abu-Hardan et al. |
| 2018/0134741 A1 | 5/2018 | Falck |
| 2018/0362669 A1 | 12/2018 | Fujita et al. |
| 2019/0029272 A1 | 1/2019 | Niemann |
| 2019/0153555 A1 | 5/2019 | Eyal et al. |
| 2019/0233862 A1 | 8/2019 | Cao et al. |
| 2019/0281874 A1 | 9/2019 | Davidek et al. |
| 2020/0071736 A1 | 3/2020 | Hammerer et al. |
| 2020/0113215 A1 | 4/2020 | Hofmekler |
| 2020/0123577 A1 | 4/2020 | De Laat et al. |
| 2020/0128860 A1 | 4/2020 | Hofmekler |
| 2020/0216574 A1 | 7/2020 | Richard et al. |
| 2020/0263265 A1 | 8/2020 | Wu et al. |
| 2020/0299791 A1 | 9/2020 | McKay et al. |
| 2020/0308212 A1 | 10/2020 | Falck |
| 2021/0120855 A1 | 4/2021 | Park et al. |
| 2021/0177021 A1 | 6/2021 | Simmons |
| 2021/0207321 A1 | 7/2021 | Loureiro et al. |
| 2021/0227853 A1 | 7/2021 | Pia |
| 2021/0253977 A1 | 8/2021 | Huang et al. |
| 2021/0315245 A1 | 10/2021 | Simmons |
| 2021/0347694 A1 | 11/2021 | Havenith et al. |
| 2021/0395284 A1 | 12/2021 | Baur et al. |
| 2022/0017766 A1 | 1/2022 | Kalb |
| 2022/0132896 A1 | 5/2022 | Kannar et al. |
| 2022/0273013 A1 | 9/2022 | Simmons et al. |
| 2022/0338516 A1 | 10/2022 | Simmons et al. |
| 2024/0114940 A1 | 4/2024 | Simmons et al. |

FOREIGN PATENT DOCUMENTS

| | | | |
|---|---|---|---|
| CN | 101272794 A | 9/2008 |
| CN | 101677603 A | 3/2010 |
| CN | 101899488 A | 12/2010 |
| CN | 102084055 A | 6/2011 |
| CN | 102925516 A | 2/2013 |
| CN | 103053903 A | 4/2013 |
| CN | 105722407 A | 6/2016 |
| CN | 106367449 A | 2/2017 |
| CN | 107746866 A | 3/2018 |
| CN | 108135222 A | 6/2018 |
| CN | 108157664 A | 6/2018 |
| CN | 108588144 A | 9/2018 |
| EP | 1228098 B1 | 9/2006 |
| EP | 1466926 B1 | 8/2007 |
| EP | 1751296 B1 | 4/2009 |
| EP | 1699974 B1 | 7/2009 |
| EP | 2256208 A1 | 12/2010 |
| EP | 2235195 B1 | 7/2011 |
| EP | 2076271 B1 | 9/2011 |
| EP | 1871400 B1 | 10/2011 |
| EP | 1811038 B1 | 2/2012 |
| EP | 2225387 B1 | 9/2012 |
| EP | 2265127 B1 | 10/2013 |
| EP | 2665823 A1 | 11/2013 |
| EP | 2427565 B1 | 1/2014 |
| EP | 1977652 B1 | 3/2015 |
| EP | 3010352 A1 | 4/2016 |
| EP | 3013155 A1 | 5/2016 |
| EP | 3037005 A1 | 6/2016 |
| EP | 1706477 B1 | 10/2016 |
| EP | 2313514 B1 | 11/2016 |
| EP | 2784156 B1 | 6/2017 |
| EP | 2817374 B1 | 6/2017 |
| EP | 2996492 B1 | 7/2017 |
| EP | 3041941 B1 | 12/2017 |
| EP | 2548966 B1 | 7/2018 |
| EP | 2548965 B1 | 8/2018 |
| EP | 3374315 A1 | 9/2018 |
| EP | 2117322 B1 | 10/2018 |
| EP | 3177728 B1 | 10/2018 |
| EP | 3177729 B1 | 10/2018 |
| EP | 3182830 B1 | 10/2018 |
| EP | 3190189 B1 | 12/2018 |
| EP | 3415632 A1 | 12/2018 |
| EP | 3438272 A1 | 2/2019 |
| EP | 2734633 B1 | 5/2019 |
| EP | 2917359 B1 | 7/2019 |
| EP | 3511418 A1 | 7/2019 |
| EP | 3530743 A1 | 8/2019 |
| EP | 3541870 A1 | 9/2019 |
| EP | 2917355 B1 | 10/2019 |
| EP | 3088530 B1 | 4/2020 |
| EP | 3511418 B1 | 7/2020 |
| EP | 3737769 A1 | 11/2020 |
| EP | 3010352 B1 | 12/2020 |
| EP | 3784045 A1 | 3/2021 |
| EP | 3815540 A1 | 5/2021 |
| EP | 3960772 A1 | 3/2022 |
| EP | 3981379 A2 | 4/2022 |
| EP | 3993644 A1 | 5/2022 |
| EP | 3438272 B1 | 6/2022 |
| JP | S5840066 A | 3/1983 |
| JP | H10117800 A | 5/1998 |
| JP | 2002223721 A | 8/2002 |
| JP | 2003334000 A | 11/2003 |
| JP | 2004520318 A | 7/2004 |
| JP | 2006087319 A | 4/2006 |
| JP | 2007049914 A | 3/2007 |
| JP | 2008120789 A | 5/2008 |
| JP | 2009089626 A | 4/2009 |
| JP | 2009125064 A | 6/2009 |
| JP | 2010527613 A | 8/2010 |
| JP | 2010200720 A | 9/2010 |

(56) References Cited

FOREIGN PATENT DOCUMENTS

| | | |
|---|---|---|
| JP | 2010215556 A | 9/2010 |
| JP | 2010226995 A | 10/2010 |
| JP | 2011103874 A | 6/2011 |
| JP | 2012527886 A | 11/2012 |
| JP | 2014140347 A | 8/2014 |
| JP | 2017502701 A | 1/2017 |
| KR | 20190133438 A | 12/2019 |
| WO | WO-2012107204 A1 | 8/2012 |
| WO | WO-2012133495 A1 | 10/2012 |
| WO | WO-2012141256 A1 | 10/2012 |
| WO | WO-2013016115 A1 | 1/2013 |
| WO | WO-2013096603 A2 | 6/2013 |
| WO | WO-2013159005 A2 | 10/2013 |
| WO | WO-2014170498 A1 | 10/2014 |
| WO | WO-2015107413 A1 | 7/2015 |
| WO | WO-2017057718 A1 | 4/2017 |
| WO | WO-2017104687 A1 | 6/2017 |
| WO | WO-2017107527 A1 | 6/2017 |
| WO | WO-2018106656 A1 | 6/2018 |
| WO | WO-2019010336 A1 | 1/2019 |
| WO | WO-2019055717 A1 | 3/2019 |
| WO | WO-2019102218 A2 | 5/2019 |
| WO | WO-2019138024 A1 | 7/2019 |
| WO | WO-2019162416 A1 | 8/2019 |
| WO | WO-2019227525 A1 | 12/2019 |
| WO | WO-2019229228 A1 | 12/2019 |
| WO | WO-2019239366 A1 | 12/2019 |
| WO | WO-2020009964 A1 | 1/2020 |
| WO | WO-2020035599 A1 | 2/2020 |
| WO | WO-2020097458 A1 | 5/2020 |
| WO | WO-2021032647 A1 | 2/2021 |
| WO | WO-2021074271 A1 | 4/2021 |
| WO | WO-2021074316 A1 | 4/2021 |
| WO | WO-2021116437 A2 | 6/2021 |
| WO | WO-2021116437 A3 | 7/2021 |
| WO | WO-2021140225 A1 | 7/2021 |
| WO | WO-2021243151 A1 | 12/2021 |
| WO | WO-2021257921 A1 | 12/2021 |
| WO | WO-2022034078 A1 | 2/2022 |
| WO | WO-2022060726 A1 | 3/2022 |
| WO | WO-2022067131 A1 | 3/2022 |
| WO | WO-2022069084 A1 | 4/2022 |
| WO | WO-2022073646 A1 | 4/2022 |

OTHER PUBLICATIONS

Bhale et al. Enzymatic activity of *trichoderma* species. Novus Natural Science Research, 2012, vol. 1, No. 4. 8 pages.

Brijwani et al. Production of a cellulolytic enzyme system in mixed-culture solid-state fermentation of soybean hulls supplemented with wheat bran. Process Biochemistry, vol. 45, No. 1, 120-128 (2010).

Chen et al. Characterization of a novel xylanase from Aspergillus flavus with the unique properties in production of xylooligosaccharides. J Basic Microbiol. Apr. 2019;59(4):351-358. doi: 10.1002/jobm.201800545. Epub Feb. 12, 2019.

Chica, et al. Semi-rational approaches to engineering enzyme activity: combining the benefits of directed evolution and rational design. Curr Opin Biotechnol. Aug. 2005;16(4):378-84.

Dallabernardina et al. Mixed-Linkage Glucan Oligosaccharides Produced by Automated Glycan Assembly Serve as Tools To Determine the Substrate Specificity of Lichenase. Chemistry. Mar. 2, 2017;23(13):3191-3196. doi: 10.1002/chem.201605479. Epub Feb. 3, 2017.

Danneels et al. A quantitative indicator diagram for lytic polysaccharide monooxygenases reveals the role of aromatic surface residues in HjLPMO9A regioselectivity. PLoS One. 2017; 12(5): e0178446. Published online May 31, 2017. doi: 10.1371/journal.pone.0178446.

De La Fuente et al. Development of a robust method for the quantitative determination of disaccharides in honey by gas chromatography. J Chromatogr A, 1135 (2006) 212-218.

Dos Santos et al. Structural basis for xyloglucan specificity and $\alpha$-d-Xylp(1 → 6)-D-Glcp recognition at the −1 subsite within the GH5 family. Biochemistry. Mar. 17, 2015;54(10):1930-42. doi: 10.1021/acs.biochem.5b00011. Epub Mar. 6, 2015.

EFSA Panel on Dietetic Products, Nutrition and Allergies (NDA) (2018). Safety of xylo-oligosaccharides (XOS) as a novel food pursuant to Regulation (EU) 2015/2283: (Scientific Opinion). E F S A Journal, 16(7), [5361]. DOI: https://doi.org/10.2903/j.efsa.2018.5361. 20 pages.

El Khoury et al. Beta Glucan: Health Benefits in Obesity and Metabolic Syndrome. J Nutr Metab. 2012; 2012: 851362. Published online Dec. 11, 2011. doi: 10.1155/2012/851362. 28 pages.

EP18157957.4 Extended European Search Report dated Jul. 13, 2018.

Falck et al. Arabinoxylanase from glycoside hydrolase family 5 is a selective enzyme for production of specific arabinoxylooligosaccharides. Food Chem. Mar. 1, 2018;242:579-584. doi: 10.1016/j.foodchem.2017.09.048. Epub Sep. 12, 2017.

Fanuel et al. The Podospora anserina lytic polysaccharide monooxygenase PaLPMO9H catalyzes oxidative cleavage of diverse plant cell wall matrix glycans. Biotechnol Biofuels. 2017; 10: 63. Published online Mar. 11, 2017. doi: 10.1186/s13068-017-0749-5.

Gorton. Spare the sugar. bakingbusiness.com. Mar. 31, 2013. Retrieved Sep. 16, 2020 from: https://www.bakingbusiness.com/articles/34774-spare-the-sugar. 8 pages.

Goubet et al. Polysaccharide analysis using carbohydrate gel electrophoresis: a method to study plant cell wall polysaccharides and polysaccharide hydrolases. Anal Biochem. Jan. 1, 2002;300(1):53-68.

Gras Notification—Claim of GRAS Status (Revised May 21, 2010), Claim of Exemption from the Requirement for Premarket Approval Requirements Pursuant to Proposed 21 CFR § 170.36(c)(1), pp. 000007 and 000015. EAS Consulting Group, LLC, Alexandria, Virginia, USA. Retrieved Dec. 2 from URL: http://wayback.archive-it.org/7993/20171031045331/https://www.fda.gov/downloads/Food/IngredientsPackagingLabeling/GRAS/NoticeInventory/UCM269544.pdf.

Greek Yogurt with Honey Base, Database Accession No. 4046243, Database GNPD online (Jun. 6, 2016). Mintel. 4 pages.

Green et al. Industrial Fungal Enzymes: An Occupational Allergen Perspective. Journal of Allergy, vol. 2011, Article ID 682574, 11 pages.

Gupta et al. Xylooligosaccharide—A Valuable Material from Waste to Taste: A Review. J Environ Res Develop, vol. 10, No. 3, pp. 555-563 (Jan.-Mar. 2016).

Hakala et al. Enzyme-aided alkaline extraction of oligosaccharides and polymeric xylan from hardwood kraft pulp. Carbohydr Polym. Mar. 1, 2013;93(1):102-8. doi: 10.1016/j.carbpol.2012.05.013. Epub May 11, 2012.

Hang et al. Enzymatic Production of Soluble Sugars from Corn Husks. LWT—Food Science and Technology, vol. 32, Issue 4, pp. 208-210 (Jun. 1999). DOI: https://doi.org/10.1006/fstl.1998.0530.

Jayapal et al. Value addition to sugarcane bagasse: Xylan extraction and its process optimization for xylooligosaccharides production. Industrial Crops and Products, vol. 42, pp. 14-24 (2013).

Jousse et al. Simplified Kinetic Scheme of Flavor Formation by the Maillard Reaction. Journal of Food Science, vol. 67, No. 7, pp. 2534-2542 (2002).

Karadeniz et al. Sugar composition of apple juices. European Food Research and Technology, vol. 215, pp. 145-148 (2002).

Kracher et al. Active-site copper reduction promotes substrate binding of fungal lytic polysaccharide monooxygenase and reduces stability. J Biol Chem. Feb. 2, 2018; 293(5): 1676-1687. Published online Dec. 19, 2017. doi: 10.1074/jbc.RA117.000109.

Kuhad et al. Microbial Cellulases and Their Industrial Applications. Enzyme Res. 2011; 2011: 280696. Published online Sep. 7, 2011. doi: 10.4061/2011/280696.

Lecumberri et al. A diet rich in dietary fiber from cocoa improves lipid profile and reduces malondialdehyde in hypercholesterolemic rats. Nutrition. Apr. 2007;23(4):332-41. doi: 10.1016/j.nut.2007.01.013. Epub Mar. 23, 2007.

Linares-Pastén et al. Structural Considerations on the Use of Endo-Xylanases for the Production of prebiotic Xylooligosaccharides

(56) References Cited

OTHER PUBLICATIONS from Biomass. Curr Protein Pept Sci. Jan. 2018;19(1): 48-67. Published online Jan. 2018. doi: 10.2174/1389203717666160923155209.

Loose et al. Activation of bacterial lytic polysaccharide monooxygenases with cellobiose dehydrogenase. Protein Sci. Dec. 2016; 25(12): 2175-2186. Published online Sep. 26, 2016. doi: 10.1002/pro.3043.

Lu et al. Extraction and modification of hemicellulose from lignocellulosic biomass: A review. Green Processing and Synthesis 2021; 10: 779-804.

Maehara et al. GH30 Glucuronoxylan-Specific Xylanase from *Streptomyces turgidiscabies* C56. Appl Environ Microbiol. Feb. 15 2018; 84(4): e01850-17. Published online Jan. 31, 2018. Prepublished online Nov. 27, 2017.

Maple et al. Detailed Tautomeric Equilibrium of Aqueous D-Glucose. Observation of Six Tautomers by Ultrahigh Resolution Carbon-13 NMR. J Am Chem Soc 1987, 109, 3168-3169.

Mathew et al. Xylo- and arabinoxylooligosaccharides from wheat bran by endoxylanases, utilisation by probiotic bacteria, and structural studies of the enzymes. Appl Microbiol Biotechnol. Apr. 2018;102(7):3105-3120. doi: 10.1007/s00253-018-8823-x. Epub Feb. 14, 2018.

Meier et al. Oxygen Activation by Cu LPMOs in Recalcitrant Carbohydrate Polysaccharide Conversion to Monomer Sugars. Chem Rev. Mar. 14, 2018; 118(5): 2593-2635. Published online Nov. 20, 2017. doi: 10.1021/acs.chemrev.7b00421.

Motta et al. Chapter 10: "A Review of Xylanase Production by the Fermentation of Xylan: Classification, Characterization and Applications," pp. 251-275. In Sustainable Degradation of Lignocellulosic Biomass, Chandel and Da Silva, eds. (May 15, 2013).

Nordberg Karlsson et al. Endo-xylanases as tools for production of substituted xylooligosaccharides with prebiotic properties. Appl Microbiol Biotechnol. 2018; 102(21): 9081-9088. Published online Sep. 8, 2018. doi: 10.1007/s00253-018-9343-4.

Park et al. Effect of fructo-oligosaccharide and isomalto-oligosaccharide addition on baking quality of frozen dough. Food Chem. Dec. 15, 2016;213:157-162. doi: 10.1016/j.foodchem.2016.06.067. Epub Jun. 21, 2016.

PCT/EP2019/054380 International Search Report and Written Opinion dated Jun. 27, 2019.

PCT/EP2019/072026 International Search Report and Written Opinion dated Dec. 2, 2019.

PCT/EP2020/072929 International Search Report and Written Opinion dated Dec. 8, 2020.

PCT/EP2020/085810 International Search Report and Written Opinion dated Jun. 9, 2021.

PCT/EP2021/050311 International Search Report and Written Opinion dated May 3, 2021.

Qi et al. Application of ultrafiltration and nanofiltration for recycling cellulase and concentrating glucose from enzymatic hydrolyzate of steam exploded wheat straw. Bioresour Technol. Jan. 2012;104:466-72. doi: 10.1016/j.biortech.2011.10.049. Epub Oct. 31, 2011.

Qing et al. "Chapter 19: Xylooligosaccharides Production, Quantification, and Characterization in Context of Lignocellulosic Biomass Pretreatment," pp. 391-415. In Aqueous Pretreatment of Plant Biomass for Biological and Chemical Conversion to Fuels and Chemicals, First Edition. Edited by Charles E. Wyman (2013).

Réhault-Godbert et al. The Golden Egg: Nutritional Value, Bioactivities, and Emerging Benefits for Human Health. Nutrients 11, 684 (Mar. 22, 2019). 26 pages.

Schmiele et al. Mixolab™ for rheological evaluation of wheat flour partially replaced by soy protein hydrolysate and fructooligosaccharides for bread production. LWT—Food Science and Technology, vol. 76, Part B, pp. 259-269 (Mar. 2017). Available online Jul. 5, 2016. DOI: https://doi.org/10.1016/j.lwt.2016.07.014.

Senevirathne et al. Effect of Mixed Microbial Culture Treatment on the Nutritive Value of Coffee, Green Tea and Oolong Tea Residues and the Effect of the Fermented Residues on in Vitro Rumen Fermentation. APCBEE Procedia 4 (2012) 66-72.

Short-Chain Fructooligosaccharides: Handling/Processing. Technical Evaluation Report. U.S. Department of Agriculture (USDA) Agricultural Marketing Service (AMS). Aug. 11, 2006. Retrieved Sep. 16, 2020 from URL: https://www.ams.usda.gov/sites/default/files/media/Fructooligosaccharides%20TR.pdf, 7 pages.

Simmons et al. An unexpectedly lichenase-stable hexasaccharide from cereal, horsetail and lichen mixed-linkage β-glucans (MLGs): implications for MLG subunit distribution. Phytochemistry. Nov. 2013;95:322-32. doi: 10.1016/j.phytochem.2013.08.003. Epub Sep. 8, 2013.

Simmons et al. Bonds broken and formed during the mixed-linkage glucan : xyloglucan endotransglucosylase reaction catalysed by Equisetum hetero-trans-β-glucanase. Biochem J. Apr. 1, 2017; 474(7): 1055-1070. Published online Mar. 8, 2017. Prepublished online Jan. 20, 2017. doi: 10.1042/BCJ20160935.

Simmons et al. Structural and electronic determinants of lytic polysaccharide monooxygenase reactivity on polysaccharide substrates. Nat Commun. 2017; 8: 1064. Published online Oct. 20, 2017. doi: 10.1038/s41467-017-01247-3.

Singh et al. Protein Engineering Approaches in the Post-Genomic Era. Curr Protein Pept Sci. 18: 1-11 (2017).

Sun et al. Hydrolysis of lignocellulosic materials for ethanol production: a review. Bioresour Technol. May 2002;83(1):1-11. doi: 10.1016/s0960-8524(01)00212-7.

Tanaka et al. Creation of cellobiose and xylooligosaccharides-coutilizing *Escherichia coli* displaying both β-glucosidase and β-xylosidase on its cell surface. ACS Synth. Biol. 2014, 3, 7, 446-453. Published online Oct. 24, 2013. DOI: https://doi.org/10.1021/sb400070q.

U.S. Appl. No. 16/844,960 Notice of Allowance dated Feb. 3, 2021.
U.S. Appl. No. 16/844,960 Office Action dated Sep. 22, 2020.
U.S. Appl. No. 16/999,483 Office Action dated Jul. 28, 2023.
U.S. Appl. No. 17/033,321 Notice of Allowance dated Oct. 6, 2021.
U.S. Appl. No. 17/033,321 Office Action dated Aug. 2, 2021.
U.S. Appl. No. 17/033,321 Office Action dated Jan. 11, 2021.
U.S. Appl. No. 17/083,121 Notice of Allowance dated Aug. 23, 2021.
U.S. Appl. No. 17/083,121 Notice of Allowance dated Dec. 8, 2021.
U.S. Appl. No. 17/083,121 Office Action dated May 14, 2021.
U.S. Appl. No. 17/571,199 Notice of Allowance dated Feb. 7, 2023.
U.S. Appl. No. 17/571,199 Notice of Allowance dated Oct. 14, 2022.
U.S. Appl. No. 17/571,199 Office Action dated Apr. 28, 2022.
U.S. Appl. No. 17/571,199 Office Action dated Sep. 7, 2022.
U.S. Appl. No. 17/837,868 Office Action dated Feb. 8, 2023.
U.S. Appl. No. 17/837,868 Office Action dated Jun. 5, 2023.
U.S. Appl. No. 17/837,868 Office Action dated Oct. 5, 2022.
U.S. Appl. No. 17/846,188 Notice of Allowance dated Aug. 14, 2023.
U.S. Appl. No. 17/846,188 Notice of Allowance dated Aug. 24, 2023.
U.S. Appl. No. 17/846,188 Notice of Allowance dated Jun. 20, 2023.
U.S. Appl. No. 17/846,188 Notice of Allowance dated May 30, 2023.
U.S. Appl. No. 17/846,188 Office Action dated Mar. 21, 2023.
U.S. Appl. No. 17/846,188 Office Action dated Nov. 28, 2022.

Villares et al. Lytic polysaccharide monooxygenases disrupt the cellulose fibers structure. Sci Rep. 2017; 7: 40262. Published online Jan. 10, 2017. doi: 10.1038/srep40262.

Wang et al. Relative fermentation of oligosaccharides from human milk and plants by gut microbes. European Food Research and Technology, vol. 243, pp. 133-146 (2017). Published online Jun. 20, 2016.

Watanabe, Eiichi. Membrane Separation in Cellulose Saccharification and Mixed Enzyme Culture Liquid Recycling. [Medicine and Biology, vol. No. 119, Issue No. 3, Sep. 10, 1989]. 7 pages.

Xiao et al. Application of Xylo-oligosaccharide in modifying human intestinal function. African Journal of Microbiology Research 6(9):2116-2119 (Mar. 9, 2012).

Zhang et al. Hemicellulose isolation, characterization, and the production of xylo-oligosaccharides from the wastewater of a

(56) References Cited

OTHER PUBLICATIONS viscose fiber mill. Carbohydr Polym. May 5, 2016;141:238-43. doi: 10.1016/j.carbpol.2016.01.022. Epub Jan. 12, 2016.

Zivkovic et al. Bovine Milk as a Source of Functional Oligosaccharides for Improving Human Health. Adv Nutr 2:284-289 (2011).

Co-pending U.S. Appl. No. 17/865,142, inventors Bartosiak-Jentys; Jeremy et al., filed on Jul. 14, 2022.

Machine translation of JP2008-120789, Ichiro et al., publication date: May 29, 2008. pp. 1-31.

Machine translation of JP2009-089626, Mitsuyo et al., publication date: Apr. 30, 2009. pp. 1-26.

Translation of JP 2008-120789, published May 29, 2008. 19 pages.

U.S. Appl. No. 16/999,483 Office Action dated Dec. 12, 2023.

U.S. Appl. No. 17/229,628 Notice of Allowance dated Jun. 20, 2023.

U.S. Appl. No. 17/229,628 Notice of Allowance dated Sep. 15, 2023.

U.S. Appl. No. 17/229,628 Office Action dated Apr. 5, 2023.

U.S. Appl. No. 17/229,628 Office Action dated Nov. 10, 2022.

U.S. Appl. No. 17/837,868 Notice of Allowance dated Dec. 4, 2023.

U.S. Appl. No. 17/837,868 Notice of Allowance dated Oct. 20, 2023.

U.S. Appl. No. 17/837,868 Notice of Allowance dated Sep. 27, 2023.

Co-pending U.S. Appl. No. 18/486,738, inventors Simmons; Thomas J. et al., filed on Oct. 13, 2023.

Tosh, Susan, et al., Structural characteristics and rheological properties of partially hydrolyzed oat b-glucan: the effects of molecular weight and hydrolysis method. Carbohydrate Polymers 55:425-436 (2004).

U.S. Appl. No. 16/999,483 Office Action dated Apr. 23, 2024.

Ying, Danyang, et al., Enhanced survival of spray-dried microencapsulated Lactobacillus rhamnosus GG in the presence of glucose. Journal of Food Engineering 109:597-602 (2012). Available online Oct. 18, 2011.

Meyer, P.D. Nondigestible oligosaccharides as dietary fiber. Journal of AOAC International, 87(3), 718-726 (2004).

Shigeo Sakai New oligosaccharides and funcionality, Food Industry, vol. 46 No. 6, Japan, Inc. Shikisha Korin (Tsuneo Kamata), Feb. 28, 2003, pp. 43-52. With English translation.

SEQUENCE LISTING

```
Sequence total quantity: 25
SEQ ID NO: 1                moltype = AA  length = 293
FEATURE                     Location/Qualifiers
source                      1..293
                            mol_type = protein
                            organism = Podospora anserine
SEQUENCE: 1
MKGLLSVAAL SLAVSEVSAH YIFQQLSTGS TKHGVFQYIR QNTNYNSPVT DLSSNDLRCN   60
EGGASGANTQ TVTVRAGDSF TFHLDTPVYH QGPVSVYLSK APGSASSYDG SGTWFKIKDW  120
GPTFPGGQWT LAGSYTAQLP SCITDGEYLL RIQSLGIHNP YPAGTPQFYI SCAQIKVTGG  180
GSVNPSGVAI PGAFKATDPG YTANIYSNFN SYTVPGPSVF SCGSNGGGSS PVEPQPQPTT  240
TLVTSTRAPV ATQPAGCAVA KWGQCGGNGW TGCTTCAAGS TCNTQNAYYH QCV         293

SEQ ID NO: 2                moltype = AA  length = 242
FEATURE                     Location/Qualifiers
source                      1..242
                            mol_type = protein
                            organism = Bacillus subtilis
SEQUENCE: 2
MPYLKRVLLL LVTGLFMSLF AVTATASAQT GGSFFDPFNG YNSGFWQKAD GYSNGNMFNC   60
TWRANNVSMT SLGEMRLALT SPAYNKFDCG ENRSVQTYGY GLYEVRMKPA KNTGIVSSFF  120
TYTGPTDGTP WDEIDIEFLG KDTTKVQFNY YTNGAGNHEK IVDLGFDAAN AYHTYAFDWQ  180
PNSIKWYVDG QLKHTATNQI PTTPGKIMMN LWNGTGVDEW LGSYNGVNPL YAHYDWVRYT  240
KK                                                                 242

SEQ ID NO: 3                moltype = AA  length = 948
FEATURE                     Location/Qualifiers
source                      1..948
                            mol_type = protein
                            organism = Ruminiclostridium thermocellum
SEQUENCE: 3
MGASIKTSIK IRTVAFVSII AIALSILSFI PNRAYASPQR GRPRLNAART TFVGDNGQPL   60
RGPYTSTEWT AAAPYDQIAR VKELGFNAVH LYAECFDPRY PAPGSKAPGY AVNEIDKIVE  120
RTRELGLYLV ITIGNGANNG NHNAQWARDF WKFYAPRYAK ETHVLYEIHN EPVAWGPPYS  180
SSTANPPGAV DMEIDVYRII RTYAPETPVL LFSYAVFGGK GGAAEALKDI RAFNKAVFGN  240
ENAVWTNEAV AFHGYAGWQE TTIAVEELLK AGYPCFMTEY AGGAWGSGMG GLDVELTYEL  300
ERLGVSWLTF QYIPPTGVSD DVTKPEYFSA LVENSGLSWT PDYGNWPAAR GVYGNGGLAR  360
ETATWINNFL TGTTRIEAED FDWGGNGVSY YDTDSVNVGG QYRPDEGVDI EKTSDTGGGY  420
NVGWISEGEW LEYTIRVRNP GYYNLSLRVA GISGSRVQVS FGNQDKTGVW ELPATGGFQT  480
WTTATRQVFL GAGLQKLRIN ALSGGFNLNW IELSPISTGT IPDGTYKFLN RANGKTLQEV  540
TGNNSIITAD YKGITEQHWK IQHIGGGQYR ISSAGRGWNN NWWMGFGTVG WWGTGSSTCF  600
IISPTGDGYI RIVLVGDGTN LQISSGDPSK IEGKAFHGGA NQQWAILPVS APAFPTGLSA  660
VLDSSGNTAN LTWNAAPGAN SYNVKRSTKS GGPYTTIATN ITSTNYTDTG VATGTKYYYV  720
VSAVSNGVET LNSAEAILQY PKLTGTVIGT QGSWNNIGNT IHKAFDGDLN TFFDGPTANG  780
CWLGLDFGEG VRNVITQIKF CPRSGYEQRM IGGIFQGANK EDFSDAVTLF TITSLPGSGT  840
```

```
LTSVDVDNPT  GFRYVRYLSP  DGSNGNIAEL  QFFGTPAGEE  NDDVHLGDIN  DDGNINSTDL   900
QMLKRHLLRS  IRLTEKQLLN  ADTNRDGRVD  STDLALLKRY  ILRVITTL                 948

SEQ ID NO: 4              moltype = AA   length = 443
FEATURE                   Location/Qualifiers
source                    1..443
                          mol_type = protein
                          organism = Gonapodya prolifera
SEQUENCE: 4
MARLSSLIAL  VLAFVAVSAP  ALAARGRPRL  NGKTFVADSG  VPLRGPFTST  EWTPAVPAAN    60
IANMRNYNFN  AIHLYAETFD  PNYPAAGSQK  PGYAATRVDQ  IVAATKAANM  YVVIVLANGA   120
NNGKFNLNYA  KDFWSFYAAR  YKNETHVIYE  IHNEPVQWGP  PYISSTQSPG  AVSMNADCYK   180
IIRAVAPDTP  VLLFTYASIG  GGSSAAGAVK  DAQSFNTAVF  GNANAQWTNE  AIAIHGYWGA   240
QGASDAAKAL  NAAGFSVVLT  EFAAATSPTS  PNGGQDTVLT  GFMEQQGVSW  LTFLHVPPTG   300
VSGDVTDPNQ  YTNRMTAAGI  GFDRDPGLNA  VGGGQAAPVP  VPAPAPVPSP  VPAPVPAVPA   360
VRTTTARPAP  SPSPVPAPVP  APAPVPAPVP  APVPAPVPAP  VPAPVPASPA  ATTTRRHRTR   420
PPRTTTAPAV  PAPPPAATPK  VCG                                              443

SEQ ID NO: 5              moltype = AA   length = 413
FEATURE                   Location/Qualifiers
source                    1..413
                          mol_type = protein
                          organism = Dickeya chrysanthemi
SEQUENCE: 5
MNGNVSLWVR  HCLHAALFVS  ATAGSFSVYA  DTVKIDANVN  YQIIQGFGGM  SGVGWINDLT    60
TEQINTAYGS  GVGQIGLSIM  RVRIDPDSSK  WNIQLPSARQ  AVSLGAKIMA  TPWSPPAYMK   120
SNNSLINGGR  LLPANYSAYT  SHLLDFSKYM  QTNGAPLYAI  SIQNEPDWKP  DYESCEWSGD   180
EFKSYLKSQG  SKFGSLKVIV  AESLGFNPAL  TDPVLKDSDA  SKYVSIIGGH  LYGTTPKPYP   240
LAQNAGKQLW  MTEHYVDSKQ  SANNWTSAIE  VGTELNASMV  SNYSAYVWWY  IRRSYGLLTE   300
DGKVSKRGYV  MSQYARFVRP  GALRIQATEN  PQSNVHLTAY  KNTDGKMVIV  AVNTNDSDQM   360
LSLNISNANV  TKFEKYSTSA  SLNVEYGGSS  QVDSSGKATV  WLNPLSVTTF  VSK          413

SEQ ID NO: 6              moltype = AA   length = 422
FEATURE                   Location/Qualifiers
source                    1..422
                          mol_type = protein
                          organism = Bacillus subtilis
SEQUENCE: 6
MIPRIKKTIC  VLLVCFTMLS  VMLGPGATEV  LAASDVTVNV  SAEKQVIRGF  GGMNHPAWAG    60
DLTAAQRETA  FGNGQNQLGF  SILRIHVDEN  RNNWYKEVET  AKSAVKHGAI  VFASPWNPPS   120
DMVETFNRNG  DTSAKRLKYN  KYAAYAQHLN  DFVTFMKNNG  VNLYAISVQN  EPDYAHEWTW   180
WTPQEILRFM  RENAGSINAR  VIAPESFQYL  KNLSDPILND  PQALANMDIL  GTHLYGTQVS   240
QFPYPLFKQK  GAGKDLWMTE  VYYPNSDTNS  ADRWPEALDV  SQHIHNAMVE  GDFQAYVWWY   300
IRRSYGPMKE  DGTISKRGYN  MAHFSKFVRP  GYVRIDATKN  PNANVYVSAY  KGDNKVVIVA   360
INKSNTGVNQ  NFVLQNGSAS  NVSRWITSSS  SNLQPGTNLT  VSGNHFWAHL  PAQSVTTFVV   420
NR                                                                       422

SEQ ID NO: 7              moltype = AA   length = 547
FEATURE                   Location/Qualifiers
source                    1..547
                          mol_type = protein
                          organism = Bacteroides ovatus
SEQUENCE: 7
MKNITLLFCL  FLANILLGAC  SGGEDEKKEM  DEGKGAYALF  LKKSITVSTG  ESQTDVVEW     60
AKTSWEITLG  EGDIVKSVTP  TSGGSNTGEK  QYTKVRVSCG  ANSTMKKRTQ  TIHLFDKTNE   120
TTVDLLVEQE  PPFKSVTLTV  DPSVKYQPVV  GFGGMYNPKI  WCGDNLISAS  QLDKMYGAGG   180
LGYSILRLMI  YPNESDWSAD  VEAAKAAQAN  GAIIFACPWD  CTDALADKIT  VNGKEMKHLK   240
KENYEAYANH  LIRYVTFMKE  KGVNLYAISV  QNEPDMEFTY  WTPSEVVDFV  KQYGARIRET   300
GVKLMSPEAC  GMQPEYTDPI  INNAEAFAQT  DILAGHLYNG  FTDLSSGYVK  NRHDYICGVY   360
SRIQGKTWWM  TEHLFNDGEN  SDDSSKWEFL  KWQYSLNHLG  KEIHMCMEGY  CSAYIYWYLK   420
RFYGLMGDTD  KRSPTSEGEI  TKNGYIMAHY  AQYATETTRI  KVVTNNEEVC  ATAYWDEKTG   480
EVTIVLLNLN  GASQWLEIPL  AGIKKASAVE  TNETKNMEVI  DTGLMESAEG  ITVLLSANSI   540
TSVRLTF                                                                  547

SEQ ID NO: 8              moltype = AA   length = 502
FEATURE                   Location/Qualifiers
source                    1..502
                          mol_type = protein
                          organism = Bacteroides ovatus
SEQUENCE: 8
MEKQSFSDGL  FSPLGIKRVI  FMLVLLTTSF  ISCSNSDEKG  GSLEVAQEYR  NLEFDARGSR    60
QTIQIDGPAE  WHISTSESWC  KSSHTIGEGK  QYVNITVEAN  DTQKERTATV  TVSASGAPDI   120
IINVKQSLYS  VPAYDEYIAP  DNTGMRDLTS  MQLSALMKAG  VNVGNTFEAV  IVGNDGSLSG   180
DETCWGNPTP  NKVLFEGIKA  AGFDVVRIPV  AYSHQFEDAA  TYKIKSAWMD  KVEAAVKAAL   240
DAGLYVIINI  HWEGGWLNHP  VDANKEALDE  RLEAMWKQIA  LRFRDYDDRL  LFAGTNEVNN   300
DDANGAQPTE  ENYRVQNGFN  QVFVNTVRAT  GGRNHYRHLI  VQAYNTDVAK  AVAHFTMPLD   360
IVQNRIFLEC  HYYDPYDFTI  MPNDENFKSQ  WGAAFAGGDV  SATGQEGDIE  ATLSSLNVFI   420
NNNVPVIIGE  YGPTLRDQLT  GEALENHLKS  RNDYIEYVVK  TCVKNKLVPL  YWDAGYTEKL   480
FDRTTGQPHN  AASIAAIMKG  LN                                               502
```

```
SEQ ID NO: 9                moltype = AA  length = 838
FEATURE                     Location/Qualifiers
source                      1..838
                            mol_type = protein
                            organism = Trichoderma reesei
SEQUENCE: 9
MKVSRVLALV LGAVIPAHAA FSWKNVKLGG GGGFVPGIIF HPKTKGVAYA RTDIGGLYRL   60
NADDSWTAVT DGIADNAGWH NWGIDAVALD PQDDQKVYAA VGMYTNSWDP SNGAIIRSSD  120
RGATWSFTNL PFKVGGNMPG RGAGERLAVD PANSNIIYFG ARSGNGLWKS TDGGVTFSKV  180
SSFTATGTYI PDPSDSNGYN SDKQGLMWVT FDSTSSTTGG ATSRIFVGTA DNITASVYVS  240
TNAGSTWSAV PGQPGKYFPH KAKLQPAEKA LYLTYSDGTG PYDGTLGSVW RYDIAGGTWK  300
DITPVSGSDL YFGFGGLGLD LQKPGTLVVA SLNSWWPDAQ LFRSTDSGTT WSPIWAWASY  360
PTETYYYSIS TPKAPWIKNN FIDVTSESPS DGLIKRLGWM IESLEIDPTD SNHWLYGTGM  420
TIFGGHDLTN WDTRHNVSIQ SLADGIEEFS VQDLASAPGG SELLAAVGDD NGFTFASRND  480
LGTSPQTVWA TPTWATSTSV DYAGNSVKSV VRVGNTAGTQ QVAISSDGGA TWSIDYAADT  540
SMNGGTVAYS ADGDTILWST ASSGVQRSQF QGSFASVSSL PAGAVIASDK KTNSVFYAGS  600
GSTFYVSKDT GSSFTRGPKL GSAGTIRDIA AHPTTAGTLY VSTDVGIFRS TDSGTTFGQV  660
STALTNTYQI ALGVGSGSNW NLYAFGTGPS GARLYASGDS GASWTDIQGS QGFGSIDSTK  720
VAGSGSTAGQ VYVGTNGRGV FYAQGTVGGG TGGTSSSTKQ SSSSTSSASS STTLRSSVVS  780
TTRASTVTSS RTSSAAGPTG SGVAGHYAQC GGIGWTGPTQ CVAPYVCQKQ NDYYYQCV    838

SEQ ID NO: 10               moltype = AA  length = 513
FEATURE                     Location/Qualifiers
source                      1..513
                            mol_type = protein
                            organism = Trichoderma reesei
SEQUENCE: 10
MYRKLAVISA FLATARAQSA CTLQSETHPP LTWQKCSSGG TCTQQTGSVV IDANWRWTHA   60
TNSSTNCYDG NTWSSTLCPD NETCAKNCCL DGAAYASTYG VTTSGNSLSI GFVTQSAQKN  120
VGARLYLMAS DTTYQEFTLL GNEFSFDVDV SQLPCGLNGA LYFVSMDADG GVSKYPTNTA  180
GAKYGTGYCD SQCPRDLKFI NGQANVEGWE PSSNNANTGI GGHGSCCSEM DIWEANSISE  240
ALTPHPCTTV GQEICEGDGC GGTYSDNRYG GTCDPDGCDW NPYRLGNTSF YGPGSSFTLD  300
TTKKLTVVTQ FETSGAINRY YVQNGVTFQQ PNAELGSYNG NELNDDYCTA EEAEFGGSSF  360
SDKGGLTQFK KATSGGMVLV MSLWDDYYAN MLWLDSTYPT NETSSTPGAV RGSCSTSSGV  420
PAQVESQSPN AKVTFSNIKF GPIGSTGNPS GGNPPGGNRG TTTTRRPATT TGSSPGPTQS  480
HYGQCGGIGY SGPTVCASGT TCQVLNPYYS QCL                               513

SEQ ID NO: 11               moltype = AA  length = 471
FEATURE                     Location/Qualifiers
source                      1..471
                            mol_type = protein
                            organism = Trichoderma reesei
SEQUENCE: 11
MIVGILTTLA TLATLAASVP LEERQACSSV WGQCGGQNWS GPTCCASGST CVYSNDYYSQ   60
CLPGAASSSS STRAASTTSR VSPTTSRSSS ATPPPGSTTT RVPPVGSGTA TYSGNPFVGV  120
TPWANAYAGQ FVVYDLPDRDC AALASNGEYS IADGGVAKYK NYIDTIRQIV VEYSDIRTLL  240
VIEPDSLANL VTNLGTPKCA NAQSAYLECI NYAVTQLNLP NVAMYLDAGH AGWLGWPANQ  300
DPAAQLFANV YKNASSPRAL RGLATNVANY NGWNITSPPS YTQGNAVYNE KLYIHAIGPL  360
LANHGWSNAF FITDQGRSGK QPTGQQQWGD WCNVIGTGFG IRPSANTGDS LLDSFVWVKP  420
GGECDGTSDS SAPRFDSHCA LPDALQPAPQ AGAWFQAYFV QLLTNANPSF L           471

SEQ ID NO: 12               moltype = AA  length = 239
FEATURE                     Location/Qualifiers
source                      1..239
                            mol_type = protein
                            organism = Aspergillus niger
SEQUENCE: 12
MKLPVTLAML AATAMGQTMC SQYDSASSPP YSVNQNLWGE YQGTGSQCVY VDKLSSSGAS   60
WHTEWTWSGG EGTVKSYSNS GVTFNKKLVS DVSSIPTSVE WKQDNTNVNA DVAYDLFTAA  120
NVDHATSSGD YELMIWLARY GNIQPIGKQI ATATVGGKSW EVWYGSTTQA GAEQRTYSFV  180
SESPINSYSG DINAFFSYLT QNQGFPASSQ YLINLQFGTE AFTGGPATFT VDNWTASVN   239

SEQ ID NO: 13               moltype = AA  length = 416
FEATURE                     Location/Qualifiers
source                      1..416
                            mol_type = protein
                            organism = Aspergillus niger
SEQUENCE: 13
MRISNLIVAA SAASMVSALP SRQMKKRDSG FKWVGTSESG AEFGSALPGT LGTDYTWPET   60
SKIQVLRNKG MNIFRIPFLM ERLTPDGLTS SFASTYLSDL KSTVEFVTNS GAYAVLDPHN  120
YGRFDGSIIT STSDPKTWWK NVATEFADND KVIFDTNNEY HDMEQSLVLD LNQAAINGIR  180
AAGATTQYIF VEGNAYTGAW DWTTYNDNLS GLTDSEDKII YEMHQYLDSD SSGTSETCVS  240
STIGQERLEK ATEWLKTNNK QGIVGEFAGG VNSVCEEAVE GMLAYMSENS DVWVGASWWS  300
AGPWWGTYMY SLEPTDGTAY STYLPILEKY FPSGDASASS SASVSVAAAT STASTTTAAF  360
EQTTTPATQG PSATNSAGEV NQYYQCGGIN WTGPTVCASP YTCKVQNDYY YQCVAE      416

SEQ ID NO: 14               moltype = AA  length = 331
```

```
FEATURE              Location/Qualifiers
source               1..331
                     mol_type = protein
                     organism = Aspergillus niger
SEQUENCE: 14
MKFQSTLLLA AAAGSALAVP HGSGHKKRAS VFEWFGSNES GAEFGTNIPG VWGTDYIFPD   60
PSTISTLIGK GMNFFRVQFM MERLLPDSMT GSYDEEYLAN LTTVVKAVTD GGAHALIDPH  120
NYGRYNGEII SSTSDFQTFW QNLAGQYKDN DLVMFDTNNE YYDMDQDLVL NLNQAAINGI  180
RAAGASQYIF VEGNSWTGAW TWVDVNDNMK NLTDPEDKIV YEMHQYLDSD GSGTSETCVS  240
GTIGKERITD ATQWLKDNKK VGFIGEYAGG SNDVCRSAVS GMLEYMANNT DVWKGASWWA  300
AGPWWGDYIF SLEPPDGTAY TGMLDILETY L                                331

SEQ ID NO: 15        moltype = AA  length = 465
FEATURE              Location/Qualifiers
source               1..465
                     mol_type = protein
                     organism = Trichoderma reesei
SEQUENCE: 15
MKSSISVVLA LLGHSAAWSY ATKSQYRANI KINARQTYQT MIGGGCSGAF GIACQQFGSS   60
GLSPENQQKV TQILFDENIG GLSIVRNDIG SSPGTTILPT CPATPQDKFD YVWDGSDNCQ  120
FNLTKTALKY NPNLYVYADA WSAPGCMKTV GTENLGGQIC GVRGTDCKHD WRQAYADYLV  180
QYVRFYKEEG IDISLLGAWN EPDFNPFTYE SMLSDGYQAK DFLEVLYPTL KKAFPKVDVS  240
CCDATGARQE RNILYELQQA GGERYFDIAT WHNYQSNPER PFNAGGKPNI QTEWADGTGP  300
WNSTWDYSGQ LAEGLQWALY MHNAFVNSDT SGYTHWWCAQ NTNGDNALIR LDRDSYEVSA  360
RLWAFAQYFR FARPGSVRIG ATSDVENVYV TAYVNKNGTV AIPVINAAHF PYDLTIDLEG  420
IKKRKLSEYL TDNSHNVTLQ SRYKVSGSSL KVTVEPRAMK TFWLE                 465

SEQ ID NO: 16        moltype = AA  length = 211
FEATURE              Location/Qualifiers
source               1..211
                     mol_type = protein
                     organism = Aspergillus niger
SEQUENCE: 16
MKVTAAFAGL LVTAFAAPVP EPVLVSRSAG INYVQNYNGN LGDFTYDESA GTFSMYWEDG   60
VSSDFVVGLG WTTGSSKAIT YSAEYSASGS SSYLAVYGWV NYPQAEYYIV EDYGDYNPCS  120
SATSLGTVYS DGSTYQVCTD TRTNEPSITG TSTFTQYFSV RESTRTSGTV TVANHFNFWA  180
QHGFGNSDFN YQVMAVEAWS GAGSASVTIS S                                211

SEQ ID NO: 17        moltype = AA  length = 437
FEATURE              Location/Qualifiers
source               1..437
                     mol_type = protein
                     organism = Trichoderma reesei
SEQUENCE: 17
MMMLSKSLLS AATAASALAA VLQPVPRASS FVTISGTQFN IDGKVGYFAG TNCYWCSFLT   60
NHADVDSTFS HISSSGLKVV RVWGFNDVNT QPSPGQIWFQ KLSATGSTIN TGADGLQTLD  120
YVVQSAEQHN LKLIIPFVNN WSDYGGINAY VNAFGGNATT WYTNTAAQTQ YRKYVQAVVS  180
RYANSTAIFA WELGNEPRCN GCSTDVIVQW ATSVSQYVKS LDSNHLVTLG DEGLGLSTGD  240
GAYPYTYGEG TDFAKNVQIK SLDFGTFHLY PDSWGTNYTW GNGWIQTHAA ACLAAGKPCV  300
FEEYGAQQNP CTNEAPWQTT SLTTRGMGGD MFWQWGDTFA NGAQSNSDPY TVWYNSSNWQ  360
CLVKNHVDAI NGGTTTPPPV SSTTTTSSRT SSTPPPPGGS CSPLYGQCGG SGYTGPTCCA  420
QGTCIYSNYW YSQCLNT                                                437

SEQ ID NO: 18        moltype = AA  length = 335
FEATURE              Location/Qualifiers
source               1..335
                     mol_type = protein
                     organism = Aspergillus niger
SEQUENCE: 18
MFAKLSLLSL LFSSAALGAS NQTLSYGNID KSATPEARAL LKYIQLQYGS HYISGQQDID   60
SWNWVEKNIG VAPAILGSDF TYYSPSAVAH GGKSHAVEDV IQHAGRNGIN ALVWHWYAPT  120
CLLDTAKEPW YKGFYTEATC FNVSEAVNDH GNGTNYKLLL RDIDAIAAQI KRLDQAKVPI  180
LFRPLHEPEG GWFWWGAQGP APFKKLWDIL YDRITRYHNL HNMVWVCNTA DPAWYPGNDK  240
CDIATIDHYP AVGDHGVAAD QYKKLQTVTN NERVLAMAEV GPIPDPDKQA RENVNWAYWM  300
VWSGDFIEDG KQNPNQFLHK VYNDTRVVAL NWEGA                            335

SEQ ID NO: 19        moltype = AA  length = 383
FEATURE              Location/Qualifiers
source               1..383
                     mol_type = protein
                     organism = Aspergillus niger
SEQUENCE: 19
MKLSNALLTL ASLALANVST ALPKASPAPS TSSSAASTSF ASTSGLQFTI DGETGYFAGT   60
NSYWIGFLTD NADVDLVMGH LKSSGLKILR VWGFNDVTSQ PSSGTVWYQL HQDGKSTINT  120
GADGLQRLDY VVSSAEQHDI KLIINFVNYW TDYGGMSAYV SAYGGSGETD FYTSDTMQSA  180
YQTYIKTVVE RYSNSSAVFA WELANEPRCP SCDTSVLYNW IEKTSKFIKG LDADRMVCIG  240
DEGFGLNIDS DGSYPYQFSE GLNFTMNLGI DTIDFGTLHL YPDSWGTSDD WGNGWITAHG  300
AACKAAGKPC LLEEYGVTSN HCSVEGSWQK TALSTTGVGA DLFWQYGDDL STGKSPDDGN  360
TIYYGTSDYQ CLVTDHVAAI GSA                                         383
```

```
SEQ ID NO: 20           moltype = AA  length = 452
FEATURE                 Location/Qualifiers
source                  1..452
                        mol_type = protein
                        organism = Aspergillus niger
SEQUENCE: 20
MHQRALLFSA LLTAVRAQQA GTLTEEVHPS LTWQKCTSEG SCTEQSGSVV IDSNWRWTHS    60
VNDSTNCYTG NTWDATLCPD DETCAANCAL DGADYESTYG VTTDGDSLTL KFVTGSNVGS   120
RLYLMDTSDE GYQTFNLLDA EFTFDVDVSN LPCGLNGALY FTAMDADGGV SKYPANKAGA   180
KYGTGYCDSQ CPRDLKFIDG QANVDGWEPS SNNDDNTGIGN HGSCCPEMDI WEANKISTAL  240
TPHPCDSSEQ TMCEGNDCGG TYSDDRYGGT CDPDGCDFNP YRMGNDSFYG PGKTIDTGSK   300
MTVVTQPFITD GSGSLSEIKR YYVQNGNVIA NADSNISGVT GNSITTDFCT AQKKAFGDED  360
IFAEHNGLAG ISDAMSSMVL ILSLWDDYYA SMEWLDSDYP ENATATDPGV ARGTCDSESG   420
VPATVEGAHP DSSVTFSNIK FGPINSTFSA SA                                 452

SEQ ID NO: 21           moltype = AA  length = 536
FEATURE                 Location/Qualifiers
source                  1..536
                        mol_type = protein
                        organism = Aspergillus niger
SEQUENCE: 21
MSSFQIYRAA LLLSILATAN AQQVGTYTTE THPSLTWQTC TSDGSCTTND GEVVIDANWR    60
WVHSTSSATN CYTGNEWDTS ICTDDVTCAA NCALDGATYE ATYGVTTSGS ELRLNFVTQG   120
SSKNIGSRLY LMSDDSNYEL FKLLGQEFTF DVDVSNLPCG LNGALYFVAM DADGGTSEYS   180
GNKAGAKYGT GYCDSQCPRD LKFINGEANC DGWEPSSNNV NTGVGDHGSC CAEMDVWEAN   240
SISNAFTAHP CDSVSQTMCD GDSCGGTYSA SGDRYSGTCD PDGCDYNPYR LGNTDFYGPG   300
LTVDTNSPFT VVTQFITDDG TSSGTLTEIK RLYVQNGEVI ANGASTYSSV NGSSITSAFC   360
ESEKTLFGDE NVFDKHGGLE GMGEAMAKGM VLVLSLWDDY AADMLWLDSD YPVNSSASTP   420
GVARGTCSTD SGVPATVEAE SPNAYVTYSN IKFGPIGSTY SSGSSSGSGS SSSSSSTTTK   480
ATSTTLKTTS TTSSGSSSTS AAQAYGQCGG QGWTGPTTCV SGYTCTYENA YYSQCL       536

SEQ ID NO: 22           moltype = AA  length = 744
FEATURE                 Location/Qualifiers
source                  1..744
                        mol_type = protein
                        organism = Trichoderma reesei
SEQUENCE: 22
MRYRTAAALA LATGPFARAD SHSTSGASAE AVVPPAGTPW GTAYDKAAA LAKLNLQDKV     60
GIVSGVGWNG GPCVGNTSPA SKISYPSLCL QDGPLGVRYS TGSTAFTPGV QAASTWDVNL   120
IRERGQFIGE EVKASGIHVI LGPVAGPLGK TPQGGRNWEG FGVDPYLTGI AMGQTINGIQ   180
SVGVQATAKH YILNEQELNR ETISSNPDDR TLHELYTWPF ADAVQANVAS VMCSYNKVNT   240
TWACEDQYTL QTVLKDQLGF PGYVMTDWNA QHTTVQSANS GLDMSMPGTD FNGNNRLWGP   300
ALTNAVNSNQ VPTSRVDDMV TRILAAWYLT GQDQAGYPSF NISRNVQGNH KTNVRAIARD   360
GIVLLKNDAN ILPLKKPASI AVVGSAAIIG NHARNSPSCN DKGCDDGALG MGWGSGAVNY   420
PYFVAPYDAI NTRASSQGTQ VTLSNTDNTS SGASAARGKD VAIVFITADS GEGYITVEGN   480
AGDRNNLDPW HNGNALVQAV AGANSNVIVV VHSVGAIILE QILALPQVKA VVWAGLPSQE   540
SGNALVDVLW GDVSPSGKLV YTIAKSPNDY NTRIVSGGSD SFSEGLFIDY KHFDDANITP   600
RYEFGYGLSY TKFNYSRLSV LSTAKSGPAT GAVVPGGPSD LFQNVATVTV DIANSGQVTG   660
AEVAQLYITY PSSAPRTPPK QLRGFAKLNL TPGQSGTATF NIRRRDLSYW DTASQKWVVP   720
SGSFGISVGA SSRDIRLTST LSVA                                          744

SEQ ID NO: 23           moltype = AA  length = 797
FEATURE                 Location/Qualifiers
source                  1..797
                        mol_type = protein
                        organism = Trichoderma reesei
SEQUENCE: 23
MVNNAALLAA LSALLPTALA QNNQTYANYS AQGQPDLYPE TLATLTLSFP DCEHGPLKNN    60
LVCDSSAGYV ERAQALISLF TLEELILNTQ NSGPGVPRLG LPNYQVWNEA LHGLDRANFA   120
TKGGQFEWAT SFPMPILTTA ALNRTLIHQI ADIISTQARA FSNSGRYGLD VYAPNVNGFR   180
SPLWGRGQET PGEDAFFLSS AYTYEYITGI QGGVDPEHLK VAATVKHFAG YDLENWNNQS   240
RLGFDAIITQ QDLSEYYTPQ FLAAARYAKS RSLMCAYNSV NGVPSCANSF FLQTLLRESW   300
GFPEWGYVSS DCDAVYNVFN PHDYASNQSS AAASSLRAGT DIDCGQTYPW HLNESFVAGE   360
VSRGEIERSV TRLYANLVRL GYFDKKNQYR SLGWKDVVKT DAWNISYEAA VEGIVLLKND   420
GTLPLSKKVR SIALIGPWAN ATTQMQGNYY GPAPYLISPL EAAKKAGYHV NFELGTEIAG   480
NSTTGFAKAI AAAKKSDAII YLGGIDNTIE QEGADRTDIA WPGNQLDLIK QLSEVGKPLV   540
VLQMGGGQVD SSSLKSNKKV NSLVWGGYPG QSGGVALFDI LSGKRAPAGR LVTTQYPAEY   600
VHQFPQNDMN LRPDGKSNPG QTYIWYTGKP VYEFGSGLFY TTFKETLASH PKSLKFNTSS   660
ILSAPHPGYT YSEQIPVFTF EANIKNSGKT ESPYTAMLFV RTSNAGPAPY PNKWLVGFDR   720
LADIKPGHSS KLSIPIPVSA LARVDSHGNR IVYPGKYELA LNTDESVKLE FELVGEEVTI   780
ENWPLEEQQI KDATPDA                                                  797

SEQ ID NO: 24           moltype = AA  length = 917
FEATURE                 Location/Qualifiers
MOD_RES                 511
                        note = Any amino acid
source                  1..917
                        mol_type = protein
```

-continued

```
                      organism = Trichoderma reesei
SEQUENCE: 24
MARHSIQLDK GWTFRQHQGS SPEWLPVEKV PTQVHMDLLA NKQIPDPFVD LNERAVQWIG  60
YKDWEYQVTF TPEAAQVEDA TRDLVFNGLD TFATVYLNEA KILEAENMFV SYRVNVTDRI 120
KASSENTLRI VFHSAIVRGE ELIKEHPEHN FLVRQTERSR VPVRKAQYNW GWDWGPILMT 180
AGPWKPVALE TYVARIDDVW AQSDVSQDLK TVSGIIFARV AGRPSQDDQV SLTLSLDGKA 240
VFQQTVDVAS AKDGLIKVPF KLEDPKLWYP RGYGSQPRYQ LNADLARKAS DASQIDSLSK 300
LVGFRRAELV QEPDAFGKSF YFRINNVDVF AGGSCWIPAD SYLAGVPPER YHAWAKLIAD 360
GNQVMLRVWG GGVYEEDALI EACDELGILV FHDPQFACAS YPAYPSYLEN LEVEARQQIR 420
RLRTHPSVII WAGNNEDYQV QERYKLDYEF ENKDPESWLK SSFPARYIYE HFLPKLVEEE 480
DPGKIYHPSS PWGDGKPTAD PTVGDIHQWN XPPPPISTQI THTQHPTDHP LHTVWHGTMN 540
KYQEAVNMGG RFVSEFGMEA YPHLSTTRRM ASDPAQLYPG SMVLDAHNKA IGHERRMMSY 600
VVDNFRPRHD LGGYTHLTQV VQSETMRAAY KAWRRQWGKP GARRCGGALV WQLNDCWPTM 660
SWAVVDYRLV KKPAYYAIAR ALRRVDVGVC RTWHDWTQTG AWVDENSGLV TGQVDHTLAA 720
REGTFDVWVV SSDTQPVALD LVVRFISVRT GRDVVDPILH SRVVAAANSA TDILQGKTLP 780
PSIPNPEDIT KPFPLAEYDP YVVHATITDA ATGTVIAADT AWPEPIKYLD LSDRGIAFEV 840
SSAGDEVVVS AEKPVKGFVF EEVEGLELSD NGFDVVPGEK QLVKVGGALK AGELLWTCIG 900
ADSASLKIEA SSSLAPR                                                917

SEQ ID NO: 25            moltype = AA  length = 344
FEATURE                  Location/Qualifiers
source                   1..344
                         mol_type = protein
                         organism = Trichoderma reesei
SEQUENCE: 25
MIQKLSNLLV TALAVATGVV GHGHINDIVI NGVWYQAYDP TTFPYESNPP IVVGWTAADL  60
DNGFVSPDAY QNPDIICHKN ATNAKGHASV KAGDTILFQW VPVPWPHPGP IVDYLANCNG 120
DCETVDKTTL EFFKIDGVGL LSGGDPGTWA SDVLISNNNT WVVKIPDNLA PGNYVLRHEI 180
IALHSAGQAN GAQNYPQCFN IAVSGSGSLQ PSGVLGTDLY HATDPGVLIN IYTSPLNYII 240
PGPTVVSGLP TSVAQGSSAA TATASATVPG GGSGPTSRTT TTARTTQASS RPSSTPPATT 300
SAPAGGPTQT LYGQCGGSGY SGPTRCAPPA TCSTLNPYYA QCLN                  344
```

COMPOSITIONS, THEIR USE, AND METHODS FOR THEIR FORMATION

CROSS REFERENCE

This is a continuation application of U.S. application Ser. No. 17/229,628, filed on Apr. 13, 2021, which is a continuation application of U.S. application Ser. No. 16/844,960, filed on Apr. 9, 2020 now U.S. Pat. No. 11,006,658 issued May 18, 2021, which claims priority to International Application No. PCT/EP2019/072026, filed on Aug. 16, 2019, which application claims the benefit of U.S. Provisional Application No. 62/764,660, filed Aug. 15, 2018, each of which is hereby incorporated by reference in its entirety.

SEQUENCE LISTING

The instant application contains a Sequence Listing which has been submitted electronically in XML format and is hereby incorporated by reference in its entirety. Said XML copy, created on Sep. 12, 2023, is named 56406_703_SL.txt and is 34,893 bytes in size.

BACKGROUND

Sugary foods and drinks are an important part of cultural and lifestyle habits across the world, but the sugar they contain has been linked to obesity, diabetes, poor dental health, and disruptive behavior in people. Because of this, consumer preferences have been shifting away from sugar-containing foods, and governments are increasingly implementing regulation to encourage the consumption of less sugar.

As such, industry has been searching for appropriate low-calorie sweeteners for many decades to substitute for sugar in food and beverages. Unfortunately, many sugar substitutes are produced from non-natural resources, and often offer bitter undertones or other unpleasant tastes along with their sweetness, both of which consumers find unappealing. Moreover, while many sweeteners are able to mimic the sweetness of sugar in food and drinks, few are able to mimic the broad range of roles that sugar plays in food, such as adding bulk, modulating texture, providing structure, acting as a preservative, and modulating colour and flavour through caramelisation and Maillard reactions. In addition, many bulking sweeteners that are able to mimic these physical properties of sugar have gastrointestinal tolerance issues that limit their use to levels well below the amount required to replace sugar in a standard Western diet.

Dietary fibre is an important part of a positive diet and helps maintain digestive health and a well-regulated gut flora. Such fibre comprises saccharides of varying chain lengths and types. In addition to being found naturally in a wide spectrum of foods, fibre can also be produced separately and added to other foods during their manufacture.

SUMMARY

Described herein are novel compositions comprising a mixture of oligosaccharides that surprisingly have improved and tunable properties that make them useful as ingredients in foodstuffs, cosmetics, and nutraceuticals, particularly as sugar substitutes. Furthermore, described herein are economical and efficient methods of preparing or manufacturing sugar substitutes comprising one or more oligosaccharides and one or more polysaccharides using enzymatic processes. These processes can be used to create different formulations comprising different types and amounts of the one or more oligosaccharides and the one or more polysaccharides to produce the desired properties.

In some aspects of the disclosure, a consumable composition is described. The consumable composition may comprise cello-oligosaccharides with a degree of polymerization of from two to six. The composition may also comprise at least one more type of oligosaccharide selected from: xylo-oligosaccharides with a degree of polymerization of from two to twelve, mixed-linkage glucan oligosaccharides with a degree of polymerization of from two to five or manno-oligosaccharides having a degree of polymerization of from two to twelve, xyloglucan oligosaccharides having a degree of polymerization of from four to twelve. The cello-oligosaccharide and the one more type of oligosaccharide can form at least 50% of the consumable composition w/w.

In some embodiments, the one more type of oligosaccharide may be xylo-oligosaccharides with a degree of polymerization of from two to twelve.

In some embodiments the one more type of oligosaccharide may be mixed-linkage glucan oligosaccharides with a degree of polymerization of from two to five.

In some embodiments the one more type of oligosaccharide may be manno-oligosaccharides having a degree of polymerization of from two to twelve.

In some embodiments the one more type of oligosaccharide may be xyloglucan oligosaccharides having a degree of polymerization of from four to twelve.

In some embodiments the compositions further comprise polysaccharides. In some embodiments the source of the polysaccharides may be a biomass. In some embodiments the biomass comprises corn stover, corn cob, wheat bran, wheat straw, hardwood, softwood, cellulose, chitin, chitosan, xylan, xyloglucan, mixed-linkage glucan, mannan, lignocellulose, or a combination thereof.

In some embodiments, the composition comprises at least 5% cello-oligosaccharides with a degree of polymerization of from two to six w/w.

In some embodiments, the composition comprises at most 90% cello-oligosaccharides with a degree of polymerization of from two to six w/w.

In some embodiments, the composition comprises at most 50% cello-oligosaccharides with a degree of polymerization of from two to six w/w.

In some embodiments, the consumable composition comprises at least 5% polysaccharides w/w.

In some embodiments, the consumable composition comprises at most 50% polysaccharides w/w.

In some embodiments, the cello-oligosaccharides are a mixture comprising cello-oligosaccharides with a degree of polymerization of two, three, four, five, six, or a combination thereof.

In some embodiments, the cello-oligosaccharide mixture comprises at least 5% of cello-oligosaccharides with a degree of polymerization of two w/w.

In some embodiments, the cello-oligosaccharide mixture comprises at least 15% of cello-oligosaccharides with a degree of polymerization of two w/w.

In some embodiments, the cello-oligosaccharide mixture comprises at least 30% of cello-oligosaccharides with a degree of polymerization of two w/w.

In some embodiments, the cello-oligosaccharide mixture comprises at least 50% of cello-oligosaccharides with a degree of polymerization of two w/w.

In some embodiments, the cello-oligosaccharide mixture comprises at least 80% of cello-oligosaccharides with a degree of polymerization of two w/w.

In some embodiments, the cello-oligosaccharide mixture comprises at least 90% of cello-oligosaccharides with a degree of polymerization of two w/w.

In some embodiments, the cello-oligosaccharide mixture comprises at least 5% of cello-oligosaccharides with a degree of polymerization of three w/w.

In some embodiments, the cello-oligosaccharide mixture comprises at least 5% of cello-oligosaccharides with a degree of polymerization of four w/w.

In some embodiments, the cello-oligosaccharide mixture comprises at least 5% of cello-oligosaccharides with a degree of polymerization of five w/w.

In some embodiments, the cello-oligosaccharide mixture comprises at least 5% of cello-oligosaccharides with a degree of polymerization of six w/w.

In some embodiments, the cello-oligosaccharide mixture comprises at most 20% of cello-oligosaccharides with a degree of polymerization of three w/w.

In some embodiments, the cello-oligosaccharide mixture comprises at most 15% of cello-oligosaccharides with a degree of polymerization of four w/w.

In some embodiments, the cello-oligosaccharide mixture comprises at most 10% of cello-oligosaccharides with a degree of polymerization of five w/w.

In some embodiments, the cello-oligosaccharide mixture comprises at most 8% of cello-oligosaccharides with a degree of polymerization of six w/w.

In some embodiments, the xylo-oligosaccharides are a mixture comprising xylo-oligosaccharides with a degree of polymerization of two, three, four, five, six, seven, eight, nine, ten, eleven, twelve, or a combination thereof.

In some embodiments, the composition comprises at least 5% xylo-oligosaccharides with a degree of polymerization of from two to twelve w/w.

In some embodiments, the xylo-oligosaccharide mixture comprises at least 4% of xylo-oligosaccharides with a degree of polymerization of two w/w.

In some embodiments, the xylo-oligosaccharide mixture comprises at least 15% of xylo-oligosaccharides with a degree of polymerization of two w/w.

In some embodiments, the xylo-oligosaccharide mixture comprises at least 30% of xylo-oligosaccharides with a degree of polymerization of two w/w.

In some embodiments, the xylo-oligosaccharide mixture comprises at least 50% of xylo-oligosaccharides with a degree of polymerization of two w/w.

In some embodiments, the xylo-oligosaccharide mixture comprises at least 70% of xylo-oligosaccharides with a degree of polymerization of two w/w.

In some embodiments, the xylo-oligosaccharide mixture comprises at least 5% of xylo-oligosaccharides with a degree of polymerization of three w/w.

In some embodiments, the xylo-oligosaccharide mixture comprises at least 8% of xylo-oligosaccharides with a degree of polymerization of three w/w.

In some embodiments, the xylo-oligosaccharide mixture comprises at least 15% of xylo-oligosaccharides with a degree of polymerization of three w/w.

In some embodiments, the xylo-oligosaccharide mixture comprises at least 5% of xylo-oligosaccharides with a degree of polymerization of four w/w.

In some embodiments, the xylo-oligosaccharide mixture comprises at least 5% of xylo-oligosaccharides with a degree of polymerization of five w/w.

In some embodiments, the xylo-oligosaccharide mixture comprises at least 10% of xylo-oligosaccharides with a degree of polymerization of six w/w.

In some embodiments, the xylo-oligosaccharide mixture comprises at least 3% of xylo-oligosaccharides with a degree of polymerization of seven w/w.

In some embodiments, the xylo-oligosaccharide mixture comprises at least 4% of xylo-oligosaccharides with a degree of polymerization of eight w/w.

In some embodiments, the xylo-oligosaccharide mixture comprises at least 2% of xylo-oligosaccharides with a degree of polymerization of nine w/w.

In some embodiments, the xylo-oligosaccharide mixture comprises at least 1% of xylo-oligosaccharides with a degree of polymerization of ten w/w.

In some embodiments, the xylo-oligosaccharide mixture comprises at least 1% of xylo-oligosaccharides with a degree of polymerization of eleven w/w.

In some embodiments, the xylo-oligosaccharide mixture comprises at most 15% of xylo-oligosaccharides with a degree of polymerization of four w/w.

In some embodiments, the xylo-oligosaccharide mixture comprises at most 15% of xylo-oligosaccharides with a degree of polymerization of five w/w.

In some embodiments, the xylo-oligosaccharide mixture comprises at most 20% of xylo-oligosaccharides with a degree of polymerization of six w/w.

In some embodiments, the xylo-oligosaccharide mixture comprises at most 15% of xylo-oligosaccharides with a degree of polymerization of seven w/w.

In some embodiments, the xylo-oligosaccharide mixture comprises at most 20% of xylo-oligosaccharides with a degree of polymerization of eight w/w.

In some embodiments, the xylo-oligosaccharide mixture comprises at most 10% of xylo-oligosaccharides with a degree of polymerization of nine w/w.

In some embodiments, the xylo-oligosaccharide mixture comprises at most 5% of xylo-oligosaccharides with a degree of polymerization of ten w/w.

In some embodiments, the xylo-oligosaccharide mixture comprises at most 5% of xylo-oligosaccharides with a degree of polymerization of eleven w/w.

In some embodiments, the manno-oligosaccharides are a mixture comprising manno-oligosaccharides with a degree of polymerization of two, three, four, five, six, seven, eight, nine, ten, eleven, twelve, or a combination thereof.

In some embodiments, the manno-oligosaccharide mixture comprises at least 4% of manno-oligosaccharides with a degree of polymerization of two w/w.

In some embodiments, the manno-oligosaccharide mixture comprises at least 15% of manno-oligosaccharides with a degree of polymerization of two w/w.

In some embodiments, the manno-oligosaccharide mixture comprises at least 30% of manno-oligosaccharides with a degree of polymerization of two w/w.

In some embodiments, the manno-oligosaccharide mixture comprises at least 50% of manno-oligosaccharides with a degree of polymerization of two w/w.

In some embodiments, the manno-oligosaccharide mixture comprises at least 70% of manno-oligosaccharides with a degree of polymerization of two w/w.

In some embodiments, the manno-oligosaccharide mixture comprises at least 5% of manno-oligosaccharides with a degree of polymerization of three w/w.

In some embodiments, the manno-oligosaccharide mixture comprises at least 8% of manno-oligosaccharides with a degree of polymerization of three w/w.

In some embodiments, the manno-oligosaccharide mixture comprises at least 15% of manno-oligosaccharides with a degree of polymerization of three w/w.

In some embodiments, the manno-oligosaccharide mixture comprises at least 5% of manno-oligosaccharides with a degree of polymerization of four w/w.

In some embodiments, the manno-oligosaccharide mixture comprises at least 5% of manno-oligosaccharides with a degree of polymerization of five w/w.

In some embodiments, the manno-oligosaccharide mixture comprises at least 10% of manno-oligosaccharides with a degree of polymerization of six w/w.

In some embodiments, the manno-oligosaccharide mixture comprises at least 3% of manno-oligosaccharides with a degree of polymerization of seven w/w.

In some embodiments, the manno-oligosaccharide mixture comprises at least 4% of manno-oligosaccharides with a degree of polymerization of eight w/w.

In some embodiments, the manno-oligosaccharide mixture comprises at least 2% of manno-oligosaccharides with a degree of polymerization of nine w/w.

In some embodiments, the manno-oligosaccharide mixture comprises at least 1% of manno-oligosaccharides with a degree of polymerization of ten w/w.

In some embodiments, the manno-oligosaccharide mixture comprises at least 1% of manno-oligosaccharides with a degree of polymerization of eleven w/w.

In some embodiments, the manno-oligosaccharide mixture comprises at most 15% of manno-oligosaccharides with a degree of polymerization of four w/w.

In some embodiments, the manno-oligosaccharide mixture comprises at most 15% of manno-oligosaccharides with a degree of polymerization of five w/w.

In some embodiments, the manno-oligosaccharide mixture comprises at most 20% of manno-oligosaccharides with a degree of polymerization of six w/w.

In some embodiments, the manno-oligosaccharide mixture comprises at most 15% of manno-oligosaccharides with a degree of polymerization of seven w/w.

In some embodiments, the manno-oligosaccharide mixture comprises at most 20% of manno-oligosaccharides with a degree of polymerization of eight w/w.

In some embodiments, the manno-oligosaccharide mixture comprises at most 10% of manno-oligosaccharides with a degree of polymerization of nine w/w.

In some embodiments, the manno-oligosaccharide mixture comprises at most 5% of manno-oligosaccharides with a degree of polymerization of ten w/w.

In some embodiments, the manno-oligosaccharide mixture comprises at most 5% of manno-oligosaccharides with a degree of polymerization of eleven w/w.

In some embodiments, the composition comprises at least 5% mixed-linkage glucan oligosaccharides with a degree of polymerization of from two to five w/w.

The consumable composition may be used as an ingredient in a finished product.

In some embodiments, the concentration of the consumable composition in the ingredient may be at least 20% w/w.

In some embodiments, the concentration of the consumable composition in the ingredient may be at least 40% w/w.

In some embodiments, the concentration of the consumable composition in the ingredient may be at least 60% w/w.

In some embodiments, the finished product may be a foodstuff.

In some embodiments, the finished product may be a cosmetic.

In some embodiments, the finished product may be a nutraceutical.

The concentration of the consumable composition in the finished product may be at least 1% w/w.

The concentration of the consumable composition in the finished product may be at least 2% w/w.

The concentration of the consumable composition in the finished product may be at least 5% w/w.

The concentration of the consumable composition in the finished product may be at least 10% w/w.

The composition may comprise less than 5% monosaccharides w/w.

In some embodiments, the composition may be used as a sweetener composition.

The sweetness of the compositions may be comparable to a control composition, wherein the control composition comprises primarily monosaccharides, disaccharides or a combination thereof.

The sweetness of the compositions may be higher than the sweetness of a control composition, wherein the control composition comprises primarily monosaccharides, disaccharides or a combination thereof.

In some embodiments, the composition may be used as a binding composition.

In some embodiments, the binding properties of the composition are comparable to a control composition, wherein the control composition comprises primarily monosaccharides, disaccharides or a combination thereof.

In some embodiments, the binding properties of the compositions are higher than the binding properties of a control composition, wherein the control composition comprises primarily monosaccharides, disaccharides or a combination thereof.

In some embodiments, the composition may be used as a fibre content enhancer.

In some embodiments, the fibre content of the compositions may be comparable to a control composition, wherein the control composition comprises primarily monosaccharides, disaccharides or a combination thereof.

In some embodiments, the fibre content of the compositions may be higher than the fibre content of a control composition, wherein the control composition comprises primarily monosaccharides, disaccharides or a combination thereof.

In some embodiments, the gastro-intestinal tolerance of the composition may be comparable or higher than the gastro-intestinal tolerance of a control composition, wherein the control composition comprises primarily monosaccharides, disaccharides or a combination thereof.

In some embodiments, the gastro-intestinal tolerance of the composition may be comparable or higher than the gastro-intestinal tolerance of a control composition, wherein the control composition comprises primarily one type of oligosaccharide.

In one aspect, a consumable composition is provided herein. The composition may comprise xylo-oligosaccharides with a degree of polymerization of from two to twelve. The composition may further comprise at least one more type of oligosaccharide selected from: cello-oligosaccharides with a degree of polymerization of from two to six, mixed-linkage glucan oligosaccharides with a degree of polymerization of from two to five, manno-oligosaccharides having a degree of polymerization of from two to twelve or xyloglucan oligosaccharides having a degree of polymerization of from four to twelve. The xylo-oligosaccharide and the one more type of oligosaccharide may form at least 50% of the consumable composition w/w.

In some embodiments, the one more type of oligosaccharide may be cello-oligosaccharides with a degree of polymerization of from two to six.

In some embodiments, the one more type of oligosaccharide may be mixed-linkage glucan oligosaccharides with a degree of polymerization of from two to five.

In some embodiments, the one more type of oligosaccharide may be manno-oligosaccharides having a degree of polymerization of from two to twelve.

In some embodiments, the one more type of oligosaccharide may be xyloglucan oligosaccharides having a degree of polymerization of from four to twelve.

In some embodiments, the composition further comprises polysaccharides.

In some embodiments, the source of the polysaccharides may be a biomass.

In some embodiments, the biomass comprises corn stover, corn cob, wheat bran, wheat straw, hardwood, softwood, cellulose, chitin, chitosan, xylan, xyloglucan, mixed-linkage glucan, mannan, lignocellulose, or a combination thereof.

In some embodiments, the composition comprises at least 5% cello-oligosaccharides with a degree of polymerization of from two to six w/w.

In some embodiments, the composition comprises at most 90% cello-oligosaccharides with a degree of polymerization of from two to six w/w.

In some embodiments, the composition comprises at most 50% cello-oligosaccharides with a degree of polymerization of from two to six w/w.

In some embodiments, the consumable composition comprises at least 5% polysaccharides w/w.

In some embodiments, the consumable composition comprises at most 50% polysaccharides w/w.

In some embodiments, the cello-oligosaccharides are a mixture comprising cello-oligosaccharides with a degree of polymerization of two, three, four, five, six, or a combination thereof.

In some embodiments, the cello-oligosaccharide mixture comprises at least 5% of cello-oligosaccharides with a degree of polymerization of two w/w.

In some embodiments, the cello-oligosaccharide mixture comprises at least 15% of cello-oligosaccharides with a degree of polymerization of two w/w.

In some embodiments, the cello-oligosaccharide mixture comprises at least 30% of cello-oligosaccharides with a degree of polymerization of two w/w.

In some embodiments, the cello-oligosaccharide mixture comprises at least 50% of cello-oligosaccharides with a degree of polymerization of two w/w.

In some embodiments, the cello-oligosaccharide mixture comprises at least 80% of cello-oligosaccharides with a degree of polymerization of two w/w.

In some embodiments, the cello-oligosaccharide mixture comprises at least 90% of cello-oligosaccharides with a degree of polymerization of two w/w.

In some embodiments, the cello-oligosaccharide mixture comprises at least 5% of cello-oligosaccharides with a degree of polymerization of three w/w.

In some embodiments, the cello-oligosaccharide mixture comprises at least 5% of cello-oligosaccharides with a degree of polymerization of four w/w.

In some embodiments, the cello-oligosaccharide mixture comprises at least 5% of cello-oligosaccharides with a degree of polymerization of five w/w.

In some embodiments, the cello-oligosaccharide mixture comprises at least 5% of cello-oligosaccharides with a degree of polymerization of six w/w.

In some embodiments, the cello-oligosaccharide mixture comprises at most 20% of cello-oligosaccharides with a degree of polymerization of three w/w.

In some embodiments, the cello-oligosaccharide mixture comprises at most 15% of cello-oligosaccharides with a degree of polymerization of four w/w.

In some embodiments, the cello-oligosaccharide mixture comprises at most 10% of cello-oligosaccharides with a degree of polymerization of five w/w.

In some embodiments, the cello-oligosaccharide mixture comprises at most 8% of cello-oligosaccharides with a degree of polymerization of six w/w.

In some embodiments, the xylo-oligosaccharides are a mixture comprising xylo-oligosaccharides with a degree of polymerization of two, three, four, five, six, seven, eight, nine, ten, eleven, twelve, or a combination thereof.

In some embodiments, the composition comprises at least 5% xylo-oligosaccharides with a degree of polymerization of from two to twelve w/w.

In some embodiments, the xylo-oligosaccharide mixture comprises at least 4% of xylo-oligosaccharides with a degree of polymerization of two w/w.

In some embodiments, the xylo-oligosaccharide mixture comprises at least 15% of xylo-oligosaccharides with a degree of polymerization of two w/w.

In some embodiments, the xylo-oligosaccharide mixture comprises at least 30% of xylo-oligosaccharides with a degree of polymerization of two w/w.

In some embodiments, the xylo-oligosaccharide mixture comprises at least 50% of xylo-oligosaccharides with a degree of polymerization of two w/w.

In some embodiments, the xylo-oligosaccharide mixture comprises at least 70% of xylo-oligosaccharides with a degree of polymerization of two w/w.

In some embodiments, the xylo-oligosaccharide mixture comprises at least 5% of xylo-oligosaccharides with a degree of polymerization of three w/w.

In some embodiments, the xylo-oligosaccharide mixture comprises at least 8% of xylo-oligosaccharides with a degree of polymerization of three w/w.

In some embodiments, the xylo-oligosaccharide mixture comprises at least 15% of xylo-oligosaccharides with a degree of polymerization of three w/w.

In some embodiments, the xylo-oligosaccharide mixture comprises at least 5% of xylo-oligosaccharides with a degree of polymerization of four w/w.

In some embodiments, the xylo-oligosaccharide mixture comprises at least 5% of xylo-oligosaccharides with a degree of polymerization of five w/w.

In some embodiments, the xylo-oligosaccharide mixture comprises at least 10% of xylo-oligosaccharides with a degree of polymerization of six w/w.

In some embodiments, the xylo-oligosaccharide mixture comprises at least 3% of xylo-oligosaccharides with a degree of polymerization of seven w/w.

In some embodiments, the xylo-oligosaccharide mixture comprises at least 4% of xylo-oligosaccharides with a degree of polymerization of eight w/w.

In some embodiments, the xylo-oligosaccharide mixture comprises at least 2% of xylo-oligosaccharides with a degree of polymerization of nine w/w.

In some embodiments, the xylo-oligosaccharide mixture comprises at least 1% of xylo-oligosaccharides with a degree of polymerization of ten w/w.

In some embodiments, the xylo-oligosaccharide mixture comprises at least 1% of xylo-oligosaccharides with a degree of polymerization of eleven w/w.

In some embodiments, the xylo-oligosaccharide mixture comprises at most 15% of xylo-oligosaccharides with a degree of polymerization of four w/w.

In some embodiments, the xylo-oligosaccharide mixture comprises at most 15% of xylo-oligosaccharides with a degree of polymerization of five w/w.

In some embodiments, the xylo-oligosaccharide mixture comprises at most 20% of xylo-oligosaccharides with a degree of polymerization of six w/w.

In some embodiments, the xylo-oligosaccharide mixture comprises at most 15% of xylo-oligosaccharides with a degree of polymerization of seven w/w.

In some embodiments, the xylo-oligosaccharide mixture comprises at most 20% of xylo-oligosaccharides with a degree of polymerization of eight w/w.

In some embodiments, the xylo-oligosaccharide mixture comprises at most 10% of xylo-oligosaccharides with a degree of polymerization of nine w/w.

In some embodiments, the xylo-oligosaccharide mixture comprises at most 5% of xylo-oligosaccharides with a degree of polymerization of ten w/w.

In some embodiments, the xylo-oligosaccharide mixture comprises at most 5% of xylo-oligosaccharides with a degree of polymerization of eleven w/w.

In some embodiments, the manno-oligosaccharides are a mixture comprising manno-oligosaccharides with a degree of polymerization of two, three, four, five, six, seven, eight, nine, ten, eleven, twelve, or a combination thereof.

In some embodiments, the composition comprises at least 5% mixed-linkage glucan oligosaccharides with a degree of polymerization of from two to five w/w.

In some embodiments, the consumable composition may be used as an ingredient in a finished product.

In some embodiments, the concentration of the consumable composition in the ingredient may be at least 20% w/w.

In some embodiments, the concentration of the consumable composition in the ingredient may be at least 40% w/w.

In some embodiments, the concentration of the consumable composition in the ingredient may be at least 60% w/w.

In some embodiments, the finished product may be a foodstuff.

In some embodiments, the finished product may be a cosmetic.

In some embodiments, the finished product may be a nutraceutical.

In some embodiments, the concentration of the consumable composition in the finished product may be at least 1% w/w.

In some embodiments, the concentration of the consumable composition in the finished product may be at least 2% w/w.

In some embodiments, the concentration of the consumable composition in the finished product may be at least 5% w/w.

In some embodiments, the concentration of the consumable composition in the finished product may be at least 10% w/w.

In some embodiments, the composition comprises less than 5% monosaccharides w/w. In some embodiments, the composition may be used as a sweetener composition.

In some embodiments, the sweetness of the compositions may be comparable to a control composition, wherein the control composition comprises primarily monosaccharides, disaccharides or a combination thereof.

In some embodiments, the sweetness of the compositions may be higher than the sweetness of a control composition, wherein the control composition comprises primarily monosaccharides, disaccharides or a combination thereof.

In some embodiments, the gastro-intestinal tolerance of the composition may be comparable or higher than the gastro-intestinal tolerance of a control composition, wherein the control composition comprises primarily monosaccharides, disaccharides or a combination thereof.

In some embodiments, the gastro-intestinal tolerance of the composition may be comparable or higher than the gastro-intestinal tolerance of a control composition, wherein the control composition comprises primarily one type of oligosaccharide.

In one aspect, provided herein is a foodstuff ingredient, cosmetic ingredient, or nutraceutical ingredient composition comprising at least two oligosaccharides. The oligosaccharides may be selected from the list consisting of cello-oligosaccharides having a degree of polymerisation of from two to six, xylo-oligosaccharides having a degree of polymerisation of from two to twelve, mixed-linkage glucan oligosaccharides having a degree of polymerisation of from two to five, manno-oligosaccharides having a degree of polymerisation of from two to twelve, xyloglucan oligosaccharides having a degree of polymerisation of from four to twelve, and chito-oligosaccharides having a degree of polymerisation of from two to twelve. The composition may comprise at least 10% by dry weight of each of the at least two oligosaccharides; wherein the ingredient comprises at least 50% by dry weight of saccharide present.

In some embodiments, the composition comprises at least 20% by dry weight, preferably at least 30% by dry weight, cello-oligosaccharides having a degree of polymerisation of from two to six.

In some embodiments, the composition comprises at least 20% by dry weight, preferably at least 30% by dry weight, xylo-oligosaccharides having a degree of polymerisation of from two to twelve.

In some embodiments, the composition comprises at least 20% by dry weight, preferably at least 30% by dry weight, mixed-linkage glucan oligosaccharides having a degree of polymerisation of from two to five.

In some embodiments, the composition comprises at least 20% by dry weight, preferably at least 30% by dry weight, manno-oligosaccharides having a degree of polymerisation of from two to twelve.

In some embodiments, the composition comprises at least 20% by dry weight, preferably at least 30% by dry weight, xyloglucan oligosaccharides having a degree of polymerisation of from four to twelve.

In some embodiments, the composition comprises at least 20% by dry weight, preferably at least 30% by dry weight, chito-oligosaccharides having a degree of polymerisation of from two to twelve.

In some embodiments, the composition comprises a polysaccharide, preferably a cellulosic polysaccharide, such as cellulose, or a polysaccharide derivative, preferably a cellulose derivative, such as carboxymethylcellulose, or a polysaccharide aggregate, such as lignocellulosic material, preferably undigested lignocellulosic material, such as from an enzymatic reaction that produced the oligosaccharides, preferably the composition comprises from greater than 0 to 40% by dry weight of the polysaccharide, the polysaccharide derivative or the polysaccharide aggregate.

In some embodiments, the composition comprises a phenolic compound, preferably a portion of lignin or a product of lignin breakdown.

In some embodiments, the composition may be in dry form.

In one aspect, provided herein is a foodstuff, cosmetic, or nutraceutical, comprising an oligosaccharide mixture, wherein the oligosaccharide mixture comprises two oligosaccharides. The oligosaccharides may be selected from the list consisting of cello-oligosaccharides having a degree of polymerisation of from two to six, xylo-oligosaccharides having a degree of polymerisation of from two to twelve, mixed-linkage glucan oligosaccharides having a degree of polymerisation of from two to five, manno-oligosaccharides having a degree of polymerisation of from two to twelve, xyloglucan oligosaccharides having a degree of polymerisation of from four to twelve; and chito-oligosaccharides having a degree of polymerisation of from two to twelve. The two oligosaccharides may be present in a ratio of from 1:9 to 9:1, preferably from 1:4 to 4:1, more preferably from 1:3 to 3:1, most preferably 2:3 to 3:2, in relation to each other, optionally wherein the oligosaccharide mixture comprises third oligosaccharides selected from the list. The ingredient may comprise at least 50% by dry weight of the two oligosaccharides present.

In one aspect, described herein is a foodstuff ingredient, cosmetic ingredient, or nutraceutical ingredient composition comprising a saccharide component. The saccharide component may comprise monosaccharides at <5% w/w of total saccharide component (comprising glucose, xylose and/or mannose), disaccharides at >20% w/w of total saccharide component (comprising cello-, xylo- and/or manno-oligosaccharides), wherein the disaccharides are at <50% w/w of total saccharide component, trisaccharides at >5% w/w of total saccharide component (comprising cello-, xylo- and/or manno-oligosaccharides), tetrasaccharides at >2% w/w of total saccharide component (comprising cello-, xylo- and/or manno-oligosaccharides). The total composition may comprise at least 20% by dry weight of saccharides.

In some embodiments, the foodstuff ingredient, cosmetic ingredient, or nutraceutical ingredient composition comprises less than 4% by dry weight of total saccharide component, preferably less than 3% by dry weight of total saccharide component, monosaccharides (comprising glucose, xylose and/or mannose).

In some embodiments, the composition comprises at least 25% by dry weight of total saccharide component, preferably at least 30% by dry weight of total saccharide component, disaccharides (comprising cello-, xylo- and/or manno-oligosaccharides).

In some embodiments, wherein the composition comprises at least 7.5% by dry weight of total saccharide component, preferably at least 10% by dry weight of total saccharide component, trisaccharides (comprising cello-, xylo- and/or manno-oligosaccharides).

In some embodiments, the composition comprises at least 3% by dry weight of total saccharide component, preferably at least 4% by dry weight of total saccharide component, tetrasaccharides (comprising cello-, xylo- and/or manno-oligosaccharides).

In some embodiments, the composition comprises at least 30%, preferably at least 40%, more preferably at least 50%, by dry weight saccharides.

In some embodiments, the composition comprises a polysaccharide, preferably a cellulosic polysaccharide, such as cellulose, or a hemicellulosic polysaccharide, such as xylan, or a polysaccharide derivative, preferably a cellulose derivative, such as carboxymethylcellulose, or a polysaccharide aggregate, such as lignocellulosic material, preferably undigested lignocellulosic material, such as from an enzymatic reaction that produced the oligosaccharides, preferably the composition comprises from greater than 0 to 40% by dry weight of the polysaccharide, the polysaccharide derivative or the polysaccharide aggregate.

In some embodiments, the composition comprises a phenolic compound, preferably a portion of lignin or a product of lignin breakdown.

In one aspect, described herein is a foodstuff ingredient, cosmetic ingredient, or nutraceutical ingredient comprising at least two oligosaccharides derived from lignocellulosic polymers. The oligosaccharides may be selected from the list consisting of cellulose, xylan, mixed-linkage glucan, mannan, xyloglucan, chitin, or a combination thereof. The ingredient can comprise at least 10% by dry weight of each of the at least two oligosaccharides, and at least 50% by dry weight of each of the at least two oligosaccharides.

According to an aspect of the disclosure, there is provided a foodstuff ingredient, cosmetic ingredient, or nutraceutical ingredient composition comprising at least two oligosaccharides selected from the list consisting of:
  i) cello-oligosaccharides having a degree of polymerisation of from two to six;
  ii) xylo-oligosaccharides having a degree of polymerisation of from two to twelve;
  iii) mixed-linkage glucan oligosaccharides having a degree of polymerisation of from two to five;
  iv) manno-oligosaccharides having a degree of polymerisation of from two to twelve;
  v) xyloglucan oligosaccharides having a degree of polymerisation of from four to twelve; and/or
  vi) chito-oligosaccharides having a degree of polymerisation of from two to twelve,
wherein the composition comprises at least 10%, by dry weight of each of the at least two oligosaccharides, and wherein the ingredient comprises at least 50% by dry weight of the two or more oligosaccharides present.

According to another aspect of the disclosure, there is provided the use of an oligosaccharide mixture in the formation of a foodstuff, cosmetic, or nutraceutical, wherein the oligosaccharide mixture comprises two oligosaccharides selected from the list consisting of:
  i) cello-oligosaccharides having a degree of polymerisation from two to six;
  ii) xylo-oligosaccharides having a degree of polymerisation of from two to twelve;
  iii) mixed-linkage glucan oligosaccharides having a degree of polymerisation of from two to five;
  iv) manno-oligosaccharides having a degree of polymerisation of from two to twelve;
  v) xyloglucan oligosaccharides having a degree of polymerisation of from four to twelve; and/or
  vi) chito-oligosaccharides having a degree of polymerisation of from two to twelve,
wherein the two oligosaccharides are present in a ratio of from 1:9 to 9:1, preferably from 1:4 to 4:1, more preferably from 1:3 to 3:1, most preferably 2:3 to 3:2, in relation to each other, optionally wherein the oligosaccharide mixture comprises third oligosaccharides selected from (i) to (vi), and wherein the ingredient comprises at least 50% by dry weight of the two or more oligosaccharides present.

According to another aspect of the disclosure, there is provided a method for producing a foodstuff ingredient, cosmetic ingredient, or nutraceutical ingredient, the ingredient comprising one or more oligosaccharides and one or more polysaccharides, wherein the method comprises the steps of:
  a) forming the one or more oligosaccharides and one or more polysaccharides by an enzymatic reaction, the enzymatic reaction comprising the step of contacting, in a solution or suspension, one or more polysaccharide-cleaving enzymes and one or more feedstocks, wherein the one or more feedstocks comprise sugar cane, corn stover, corn cob, wheat bran, wheat straw, hardwood, softwood, cellulose, chitin, chitosan, xylan, xyloglucan, mixed-linkage glucan, mannan, and/or lignocellulose;

b) separating the one or more oligosaccharides and the one or more polysaccharides from the enzymatic reaction mixture; and/or c) recombining the one or more oligosaccharides and the one or more polysaccharides to form the ingredient.

Optionally, the method for producing an ingredient may include a washing step to separate oligosaccharide fractions before recombining the one or more oligosaccharides.

Optionally, a portion of the one or more oligosaccharides may be recombined with a portion of the one or more polysaccharides to form an ingredient.

Preparing the foodstuff, cosmetic, or nutraceutical ingredient in this way can allow for efficient use of biomass by incorporating oligomeric and polymeric material from the same biomass source. Such preparation can also allow for optional purification, derivatisation and/or other modification, and/or control of oligomeric and polymeric proportions, which can improve the functional properties, nutritional properties, and/or tolerance of the ingredient.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Figure 1:
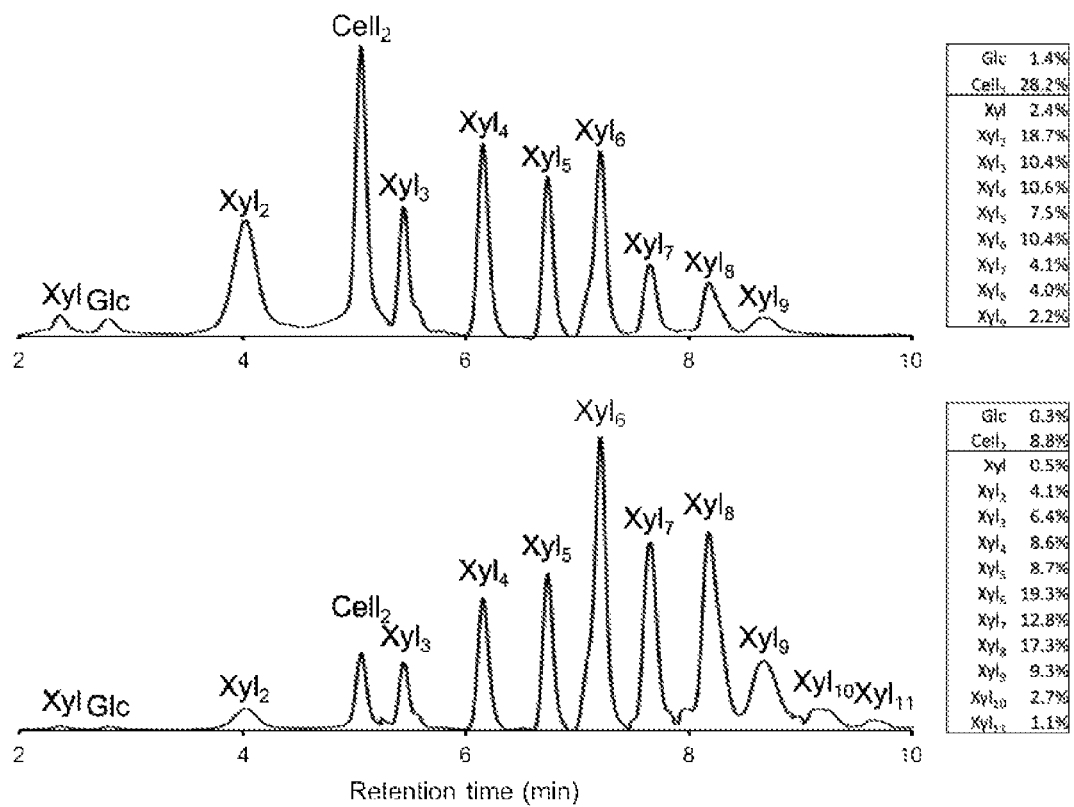
FIG. 1 shows HPLC trace data of oligosaccharide compositions that are expected to be created after digestion with enzymes.

Described herein are saccharide compositions that can be useful in foodstuff, cosmetic, or nutraceutical products. Some embodiments of the present disclosure additionally offer such foodstuff, cosmetic, or nutraceutical products with novel properties. The saccharide compositions may be consumable compositions including cello-oligosaccharides, xylo-oligosaccharides, mixed-linkage glucan oligosaccharides, manno-oligosaccharides, and/or xyloglucan oligosaccharides. Such consumable compositions may be used as sweeteners (e.g., in a foodstuff), binders, and/or fibre content enhancers.

As used herein, "food" and "foodstuff" refer to any item destined for consumption, which may be consumption by a human or by any other animal. It may be food, feed, a beverage, or an ingredient to be used in the production of any of the above.

As used herein, "nutraceutical" refers to any composition introduced into a human or other animal, whether by ingestion, injection, absorption, or any other method, for the purpose of providing nutrition to the human or other animal. Use of such a nutraceutical may take the form of a drink with added dietary fibre, a prebiotic additive, a pill or other capsule, or any other suitable use.

As used herein, "cosmetic" refers to any composition which is intended for use on humans or other animals to increase their aesthetic appeal or prevent future loss of aesthetic appeal, as well as any other compositions known in general parlance as cosmetics. Aesthetic appeal is not limited to visual aesthetics but applies as well to textural or any other appeal. The cosmetic may be mascara, foundation, lip gloss, eyeshadow, eyeliner, primer, lipstick blush, nail polish, bronzer, or any other makeup: shampoo, conditioner, styling mousse, styling gel, hairspray, hair dye, hair wax, or any other hair product: moisturiser, exfoliant, sun cream, cleanser, toothpaste, or a cream, a lotion, ointment or any other composition effective in modifying teeth, skin, hair, or other parts of the body in some aesthetic way. Or the cosmetic may be a composition used as a component of a face mask, brush, hair roller, other styling device, or other solid structure, or any other suitable composition.

As used herein, "polysaccharide" refers to a saccharide polymer of any length greater than about 20 residues. Polysaccharides may be highly branched, lightly branched, or unbranched, may comprise any manner of glycosidic bond in any combination, any number of, for example, α or β linkages, and any combination of monomer types, such as glucose, glucosamine, mannose, xylose, galactose, fucose, fructose, glucuronic acid, arabinose, or derivatives thereof such as any combination of the above monomers decorated with acetyl or other groups. The polysaccharide may be a cellulosic or hemicellulosic polymer, hemicellulosic polymers envisaged including xylan, glucuronoxylan, arabinoxylan, glucomannan, and xyloglucan. In some embodiments, cellulose is the preferred cellulosic polymer.

As used herein, "lignocellulose" refers to polysaccharide-comprising aggregates that are, or are derived from, plant cell wall material. For example, they may comprise one or more of the following polysaccharides associated together: cellulose, xylan, mannan, and mixed-linkage glucan.

As used herein "highly branched," "lightly branched," and "unbranched" refer to the number of side-chains per stretch of main chain in a saccharide. Highly branched saccharides have on average from 4 to 10 side chains per 10 main-chain residues, slightly branched saccharides have on average from 1 to 3 side chains per 10 main-chain residues, and unbranched saccharides have only one main chain and no side chains. The average is calculated by dividing the number of side chains in a saccharide by the number of main-chain residues.

As used herein, "saccharide" refers to any polysaccharide and/or oligosaccharide, such as monosaccharide and/or disaccharide.

As used herein, "oligosaccharide" refers to saccharide polymers having chain lengths less than or equal to about 20 saccharide residues. Oligosaccharides may be highly branched, lightly branched, or unbranched, may comprise glycosidic bonds in any combination, any number of α or β linkages, and any combination of monomer types, such as glucose, glucosamine, mannose, xylose, galactose, fucose, fructose, glucuronic acid, arabinose, or derivatives thereof. Suitable derivatives include the above monomers comprising acetyl or other groups.

As used herein, "monosaccharide" and "disaccharide" refer to saccharide compounds consisting respectively of one or two residues. Monosaccharides are compounds such as glucose, glucosamine, xylose, galactose, fucose, fructose, glucuronic acid, arabinose, galacturonic acid; or epimers or other derivatives thereof. Suitable derivatives include acetyl or other groups. Disaccharides are compounds consisting of two monosaccharides joined via any glycosidic bond.

As used herein, "cello-oligosaccharides" refers to oligosaccharides composed of one or more glucose residues linked by β-1,4-glycosidic bonds, and may be chemically related to that by oxidation, reduction, esterification, epimerisation, or another chemical modification.

As used herein, "xylo-oligosaccharides" refers to oligosaccharides composed primarily of xylose residues (typically linked by β-1,4-glycosidic bonds) and may also contain glucuronic acid residues and/or arabinose residues and/or acetyl groups and/or any other modification, and may be chemically related to that by oxidation, reduction, esterification, epimerisation, or another chemical modification.

As used herein, "mixed-linkage glucan-oligosaccharides" refers to oligosaccharides composed of one or more glucose residues linked by at least one β-1,3-glycosidic bond and at least one β-1,4-glycosidic bond, and may be chemically related to that by oxidation, reduction, esterification, epimerisation, or another chemical modification As used herein, "manno-oligosaccharides" refers to oligosaccharides composed of one or more mannose residues and optionally containing one or more glucose and/or galactose residues, and may be chemically related to that by oxidation, reduction, esterification, epimerisation, or another chemical modification:

As used herein, "chito-oligosaccharides" refers to oligosaccharides composed of one or more glucosamine and/or N-acetyl-glucosamine residues, and may be chemically related to that by oxidation, reduction, esterification, epimerisation, or another chemical modification.

As used herein, "cellulose" refers to polysaccharides composed of glucose residues linked by β-1,4-glycosidic bonds, and derivatives thereof. "Xylan" refers to polysaccharides composed of a backbone of xylose residues and may also contain glucuronic acid residues and/or arabinose residues and/or acetyl groups and/or any other modification. "Mixed-linkage glucan" refers to polysaccharides composed of glucose residues linked by β-1,3-glycosidic bonds and β-1,4-glycosidic bonds. "Mannan" refers to polysaccharides composed of greater than 40% mannose residues and optionally containing glucose and/or galactose residues. "Chitin" or "chitosan" refer to polysaccharides composed of glucosamine and/or N-acetyl-glucosamine residues.

The term "about" as used herein can mean within 1 or more than 1 standard deviation. Alternatively, "about" can mean a range of up to 10%, up to 5%, or up to 1% of a given value. For example, about can mean up to +10%, +9%, +8%, +7%, +6%, +5%, +4%, +3%, +2%, or +1% of a given value.

Compositions

The polysaccharide components of the composition may comprise one or more of any type of polysaccharide. Preferably they comprise cellulose, xylan, mixed-linkage glucan, mannan, xyloglucan, chitin or chitosan, or derivatives of any of the aforementioned polysaccharides.

The composition may comprise various oligosaccharides, and at varying amounts, depending on the desired properties. Suitably, the composition may comprise at least 20% by dry weight, preferably at least 30% by dry weight, cello-oligosaccharides having a degree of polymerisation of from two to six and/or the composition may comprise at least 20% by dry weight, preferably at least 30% by dry weight, xylo-oligosaccharides having a degree of polymerisation of from two to twelve and/or the composition may comprise at least 20% by dry weight, preferably at least 30% by dry weight, mixed-linkage glucan oligosaccharides having a degree of polymerisation of from two to five, and/or the composition may comprise at least 20% by dry weight, preferably at least 30% by dry weight, manno-oligosaccharides having a degree of polymerisation of from two to twelve, and/or the composition may comprise at least 20% by dry weight, preferably at least 30% by dry weight, xyloglucan oligosaccharides having a degree of polymerisation of from four to twelve, and/or the composition may comprise at least 20% by dry weight, preferably at least 30% by dry weight, chito-oligosaccharides having a degree of polymerisation of from two to twelve. The skilled person will understand that the composition can comprise a maximum of 100% by dry weight of the above oligosaccharides, therefore the above embodiment, wherein the oligosaccharides are present in at least 20% by dry weight, does not comprise all six types of oligosaccharides.

In another aspect, provided herein is the use of an oligosaccharide mixture in the formation of a foodstuff, cosmetic, or nutraceutical, wherein the oligosaccharide mixture comprises two oligosaccharides selected from the list consisting of:
  i) cello-oligosaccharides having a degree of polymerisation of from two to six;
  ii) xylo-oligosaccharides having a degree of polymerisation of from two to twelve;
  iii) mixed-linkage glucan oligosaccharides having a degree of polymerisation of from two to five;
  iv) manno-oligosaccharides having a degree of polymerisation of from two to twelve;
  v) xyloglucan oligosaccharides having a degree of polymerisation of from four to ten; and/or
  vi) chito-oligosaccharides having a degree of polymerisation of from two to twelve, wherein the two oligosaccharides may be present in a ratio of from 1:9 to 9:1, preferably 1:4 to 4:1, more preferably from 2:3 to 3:2, in relation to each other.

The amounts of each of the oligosaccharides may be varied depending on the desired properties of the resulting foodstuff, cosmetic, or nutraceutical. Preferably the two oligosaccharides may be present in a ratio of 1:9 to 9:1, preferably 1:2 to 2:1, more preferably 2:3 to 3:2, in relation to each other.

The oligosaccharide mixture may further comprise a third oligosaccharide and a fourth oligosaccharide. The oligosaccharide mixture may comprise a third oligosaccharide, a fourth oligosaccharide, and a fifth oligosaccharide. The oligosaccharide mixture may further comprise a third oligosaccharide, a fourth oligosaccharide, a fifth oligosaccharide, and a sixth oligosaccharide. These oligosaccharides may be selected from the same list as the at least two oligosaccharides as provided above.

Preferred oligosaccharide mixtures of the at least two oligosaccharides may comprise the cello-oligosaccharides, for instance, cello-oligosaccharides in combination with the xylo-oligosaccharides. An alternative preferable composition may comprise cello-oligosaccharides in combination with manno-oligosaccharides.

Optionally, the oligosaccharide mixtures of the at least two oligosaccharides may additionally include a polysaccharide, preferably a cellulosic polysaccharide, such as cellulose, or a polysaccharide derivative, preferably a cellulose derivative, such as carboxymethylcellulose, or a polysaccharide aggregate, preferably a portion of lignocellulosic biomass. Suitably, the ratio in the combination may be from 1:100 to 1:1 polysaccharide/polysaccharide derivative/polysaccharide aggregate:oligosaccharide, preferably from 1:90 to 1:2, preferably from 1:80 to 1:3, preferably from 1:70 to 1:4, and preferably from 1:60 to 1:5. As such, the ratio between the first oligosaccharide, the second oligosaccharide, and the polysaccharide may be from 2:2:1 to 30:30:1, preferably about 3:3:1.

Combinations of Oligosaccharides

A composition may comprise a mixture of one or more oligosaccharides. A mixture of oligosaccharides may comprise two forms of oligosaccharides, for instance, cello-oligosaccharides and xylo-oligosaccharides. A mixture of oligosaccharides may comprise three forms of oligosaccharides, for instance, cello-oligosaccharides, manno-oligosaccharides, and xylo-oligosaccharides. A mixture of oligosaccharides may comprise four forms of oligosaccharides, for instance, cello-oligosaccharides, manno-oligosaccharides, mixed-linkage glucan oligosaccharides, chito-oligosaccharides, and xylo-oligosaccharides.

An oligosaccharide mixture may comprise two forms of oligosaccharides, for example, a first oligosaccharide and a second oligosaccharide. An oligosaccharide mixture may comprise about 5% of a first oligosaccharide and about 95% of a second oligosaccharide w/w: An oligosaccharide mixture may comprise about 10% of a first oligosaccharide and about 90% of a second oligosaccharide w/w. An oligosaccharide mixture may comprise about 15% of a first oligosaccharide and about 85% of a second oligosaccharide w/w. An oligosaccharide mixture may comprise about 20% of a first oligosaccharide and about 80% of a second oligosaccharide w/w. An oligosaccharide mixture may comprise about 25% of a first oligosaccharide and about 75% of a second oligosaccharide w/w. An oligosaccharide mixture may comprise about 30% of a first oligosaccharide and about 70% of a second oligosaccharide w/w. An oligosaccharide mixture may comprise about 35% of a first oligosaccharide and about 65% of a second oligosaccharide w/w. An oligosaccharide mixture may comprise about 40% of a first oligosaccharide and about 50% of a second oligosaccharide w/w. An oligosaccharide mixture may comprise 45% of a first oligosaccharide and 55% of a second oligosaccharide w/w. An oligosaccharide mixture may comprise 50% of a first oligosaccharide and 50% of a second oligosaccharide w/w. An oligosaccharide mixture may comprise 55% of a first oligosaccharide and 45% of a second oligosaccharide w/w. An oligosaccharide mixture may comprise 60% of a first oligosaccharide and 30% of a second oligosaccharide w/w. An oligosaccharide mixture may comprise 65% of a first oligosaccharide and 35% of a second oligosaccharide w/w. An oligosaccharide mixture may comprise 70% of a first oligosaccharide and 30% of a second oligosaccharide w/w. An oligosaccharide mixture may comprise 75% of a first oligosaccharide and 25% of a second oligosaccharide w/w. An oligosaccharide mixture may comprise 80% of a first oligosaccharide and 20% of a second oligosaccharide w/w. An oligosaccharide mixture may comprise 85% of a first oligosaccharide and 15% of a second oligosaccharide w/w. An oligosaccharide mixture may comprise 90% of a first oligosaccharide and 10% of a second oligosaccharide w/w. An oligosaccharide mixture may comprise 95% of a first oligosaccharide and 5% of a second oligosaccharide w/w. In some examples, a first oligosaccharide may be cello-oligosaccharides and a second oligosaccharide may be xylo-oligosaccharides. In some examples, a first oligosaccharide may be cello-oligosaccharides and a second oligosaccharide may be manno-oligosaccharides. In some examples, a first oligosaccharide may be xylo-oligosaccharides and a second oligosaccharide may be manno-oligosaccharides. Other combinations of a first oligosaccharide and a second oligosaccharide are also within the scope of this disclosure.

An oligosaccharide mixture may comprise three forms of oligosaccharides, for example a first oligosaccharide, a second oligosaccharide, and a third oligosaccharide. An oligosaccharide mixture may comprise about 20% of a first oligosaccharide, 40% of a second oligosaccharide, and 40% of a third oligosaccharide w/w. An oligosaccharide mixture may comprise about 30% of a first oligosaccharide, 30% of a second oligosaccharide, and 40% of a third oligosaccharide w/w. An oligosaccharide mixture may comprise about 10% of a first oligosaccharide, 10% of a second oligosaccharide, and 80% of a third oligosaccharide w/w. An oligosaccharide mixture may comprise about 20% of a first oligosaccharide, 20% of a second oligosaccharide, and 60% of a third oligosaccharide w/w. An oligosaccharide mixture may comprise about 20% of a first oligosaccharide, 30% of a second oligosaccharide, and 50% of a third oligosaccharide w/w. In some examples, a first oligosaccharide may be manno-oligosaccharides, a second oligosaccharide may be xylo-oligosaccharides, and a third oligosaccharide may be cello-oligosaccharides. In some examples, a first oligosaccharide may be xyloglucan-oligosaccharides, a second oligosaccharide may be xylo-oligosaccharides, and a third oligosaccharide may be cello-oligosaccharides. Other combinations of a first oligosaccharide, a second oligosaccharide, and a third oligosaccharide are also within the scope of this disclosure.

An oligosaccharide mixture may comprise two or more oligosaccharides, a first oligosaccharide and a second oligosaccharide which is different than the first oligosaccharide. For instance, the first oligosaccharide may be a xylo-oligosaccharide or a cello-oligosaccharide or a manno-oligosaccharide or other oligosaccharides as provided herein whereas the second oligosaccharide can be a xylo-oligosaccharide or a cello-oligosaccharide or a manno-oligosaccharide or other oligosaccharides not used as the first oligosaccharides. The ratio of a first oligosaccharide to a second oligosaccharide in the mixture may be about 1:1. The ratio of a first oligosaccharide to a second oligosaccharide in the mixture may be about 1:2. The ratio of a first oligosaccharide to a second oligosaccharide in the mixture may be about 1:3. The ratio of a first oligosaccharide to a second oligosaccharide in the mixture may be about 1:4. The ratio of a first oligosaccharide to a second oligosaccharide in the mixture may be about 1:5. The ratio of a first oligosaccharide to a second oligosaccharide in the mixture may be about 1:6. The ratio of a first oligosaccharide to a second oligosaccharide in the mixture may be about 1:7. The ratio of a first oligosaccharide to a second oligosaccharide in the mixture may be about 1:8. The ratio of a first oligosaccharide to a second oligosaccharide in the mixture may be about 1:9.

The ratio of a first oligosaccharide to a second oligosaccharide in the mixture may be about 2:1. The ratio of a first oligosaccharide to a second oligosaccharide in the mixture may be about 2:3. The ratio of a first oligosaccharide to a second oligosaccharide in the mixture may be about 2:5. The ratio of a first oligosaccharide to a second oligosaccharide in the mixture may be about 2:7. The ratio of a first oligosaccharide to a second oligosaccharide in the mixture may be about 2:9. The oligosaccharides may be cello-oligosaccharides, manno-oligosaccharides, xylo-oligosaccharides, xyloglucan-oligosaccharides, mixed-linkage oligosaccharides, chito-oligosaccharides or other oligosaccharides as provided herein wherein the first oligosaccharide is selected to be a different oligosaccharide than the second oligosaccharide.

The ratio of a first oligosaccharide to a second oligosaccharide in the mixture may be about 3:1. The ratio of a first oligosaccharide to a second oligosaccharide in the mixture may be about 3:2. The ratio of a first oligosaccharide to a second oligosaccharide in the mixture may be about 3:4. The ratio of a first oligosaccharide to a second oligosaccharide in the mixture may be about 3:5. The ratio of a first oligosaccharide to a second oligosaccharide in the mixture may be about 3:7. The ratio of a first oligosaccharide to a second oligosaccharide in the mixture may be about 3:8. The oligosaccharides may be cello-oligosaccharides, manno-oligosaccharides, xylo-oligosaccharides, xyloglucan-oligosaccharides, mixed-linkage oligosaccharides, chito-oligosaccharides or other oligosaccharides provided herein wherein the first oligosaccharide is selected to be a different oligosaccharide than the second oligosaccharide.

The ratio of a first oligosaccharide to a second oligosaccharide in an oligosaccharide mixture comprising two or more oligosaccharides may be from 1:9 to 9:1. The ratio of a first oligosaccharide to a second oligosaccharide may be from 1:4 to 4:1. The ratio of a first oligosaccharide to a second oligosaccharide may be from 1:3 to 3:1. The ratio of a first oligosaccharide to a second oligosaccharide may be from 2:3 to 3:2. The oligosaccharides may be cello-oligosaccharides, manno-oligosaccharides, xylo-oligosaccharides, xyloglucan-oligosaccharides, mixed-linkage oligosaccharides, chito-oligosaccharides or other oligosaccharides provided herein wherein the first oligosaccharide is selected to be a different oligosaccharide than the second oligosaccharide.

Oligosaccharide Compositions with Varying Degrees of Polymerization

The concentration of xylo-oligosaccharides with a degree of polymerization of two in a xylo-oligosaccharide mixture may be about 2% to about 80% w/w. The concentration of xylo-oligosaccharides with a degree of polymerization of two may be at least 2%, 4%, 6%, 8%, 10%, 12%, 15%, 18%, 20%, 25%, or 30% w/w. The concentration of xylo-oligosaccharides with a degree of polymerization of two may be higher in some cases, for instance, up to 35%, 40%, 45%, 50%, 55%, 60%, 65%, 70%, 75%, or 80% w/w.

The concentration of xylo-oligosaccharides with a degree of polymerization of three in a xylo-oligosaccharide mixture may be about 2% to about 20% w/w. The concentration of xylo-oligosaccharides with a degree of polymerization of three may be at least 2%, 4%, 6%, 8%, 10%, 12%, 15%, 18%, or 20% w/w.

The concentration of xylo-oligosaccharides with a degree of polymerization of four in a xylo-oligosaccharide mixture may be about 5% to about 20% w/w. The concentration of xylo-oligosaccharides with a degree of polymerization of four may be at least 5%, 8%, 10%, 12%, 15%, 18%, or 20% w/w.

The concentration of xylo-oligosaccharides with a degree of polymerization of five in a xylo-oligosaccharide mixture may be about 5% to about 20% w/w. The concentration of xylo-oligosaccharides with a degree of polymerization of five may be at least 5%, 7%, 8%, 10%, 12%, 15%, 18%, or 20% w/w.

The concentration of xylo-oligosaccharides with a degree of polymerization of six in a xylo-oligosaccharide mixture may be about 5% to about 25% w/w. The concentration of xylo-oligosaccharides with a degree of polymerization of six may be at least 5%, 8%, 10%, 12%, 15%, 18%, 20%, or 25% w/w.

The concentration of xylo-oligosaccharides with a degree of polymerization of seven in a xylo-oligosaccharide mixture may be about 2% to about 20% w/w. The concentration of xylo-oligosaccharides with a degree of polymerization of seven may be at least 2%, 4%, 6%, 8%, 10%, 12%, 15%, 17%, or 20% w/w.

The concentration of xylo-oligosaccharides with a degree of polymerization of eight in a xylo-oligosaccharide mixture may be about 1% to about 15% w/w. The concentration of xylo-oligosaccharides with a degree of polymerization of eight may be at least 1%, 2%, 3%, 4%, 5%, 6%, 7%, 8%, 9%, 10%, or 15% w/w.

The concentration of xylo-oligosaccharides with a degree of polymerization of nine in a xylo-oligosaccharide mixture may be about 2% to about 15% w/w. The concentration of xylo-oligosaccharides with a degree of polymerization of nine may be at least 1%, 2%, 3%, 4%, 5%, 6%, 7%, 8%, 9%, 10%, or 15% w/w.

The concentration of xylo-oligosaccharides with a degree of polymerization of ten in a xylo-oligosaccharide mixture may be about 2% to about 15% w/w. The concentration of xylo-oligosaccharides with a degree of polymerization of ten may be at least 1%, 2%, 3%, 4%, 5%, 6%, 7%, 8%, 9%, 10%, or 15% w/w.

The concentration of xylo-oligosaccharides with a degree of polymerization of eleven in a xylo-oligosaccharide mixture may be about 2% to about 15% w/w. The concentration of xylo-oligosaccharides with a degree of polymerization of eleven may be at least 1%, 2%, 3%, 4%, 5%, 6%, 7%, 8%, 9%, 10%, or 15% w/w.

The concentration of xylo-oligosaccharides with a degree of polymerization of twelve in a xylo-oligosaccharide mixture may be about 2% to about 15% w/w. The concentration of xylo-oligosaccharides with a degree of polymerization of twelve may be at least 1%, 2%, 3%, 4%, 5%, 6%, 7%, 8%, 9%, 10%, or 15% w/w.

The concentration of cello-oligosaccharides with a degree of polymerization of two in a cello-oligosaccharide mixture may be about 2% to about 80% w/w. The concentration of cello-oligosaccharides with a degree of polymerization of two may be at least 2%, 4%, 6%, 8%, 10%, 12%, 15%, 18%, 20%, 25%, or 30% w/w. The concentration of cello-oligosaccharides with a degree of polymerization of two may be higher in some cases, for instance, at least 35%, 40%, 45%, 50%, 55%, 60%, 65%, 70%, 75%, or 80% w/w.

The concentration of cello-oligosaccharides with a degree of polymerization of three in a cello-oligosaccharide mixture may be about 2% to about 20% w/w. The concentration of cello-oligosaccharides with a degree of polymerization of three may be at least 2%, 4%, 6%, 8%, 10%, 12%, 15%, 18%, or 20% w/w.

The concentration of cello-oligosaccharides with a degree of polymerization of four in a cello-oligosaccharide mixture may be about 5% to about 20% w/w. The concentration of cello-oligosaccharides with a degree of polymerization of four may be at least 5%, 8%, 10%, 12%, 15%, 18%, or 20% w/w.

The concentration of cello-oligosaccharides with a degree of polymerization of five in a cello-oligosaccharide mixture may be about 5% to about 20% w/w. The concentration of cello-oligosaccharides with a degree of polymerization of five may be at least 5%, 7%, 8%, 10%, 12%, 15%, 18%, or 20% w/w.

The concentration of cello-oligosaccharides with a degree of polymerization of six in a cello-oligosaccharide mixture may be about 5% to about 25% w/w. The concentration of cello-oligosaccharides with a degree of polymerization of six may be at least 5%, 8%, 10%, 12%, 15%, 18%, 20%, or 25% w/w.

The concentration of manno-oligosaccharides with a degree of polymerization of two in a manno-oligosaccharide mixture may be about 2% to about 30% w/w. The concentration of manno-oligosaccharides with a degree of polymerization of two may be at least 2%, 4%, 6%, 8%, 10%, 12%, 15%, 18%, 20%, 25%, or 30% w/w.

The concentration of manno-oligosaccharides with a degree of polymerization of three in a manno-oligosaccharide mixture may be about 2% to about 20% w/w. The concentration of manno-oligosaccharides with a degree of polymerization of three may be at least 2%, 4%, 6%, 8%, 10%, 12%, 15%, 18%, or 20% w/w.

The concentration of manno-oligosaccharides with a degree of polymerization of four in a manno-oligosaccharide mixture may be about 5% to about 20% w/w. The concentration of manno-oligosaccharides with a degree of polymerization of four may be at least 5%, 8%, 10%, 12%, 15%, 18%, or 20% w/w.

The concentration of manno-oligosaccharides with a degree of polymerization of five in a manno-oligosaccharide mixture may be about 5% to about 20% w/w. The concentration of manno-oligosaccharides with a degree of polymerization of five may be at least 5%, 7%, 8%, 10%, 12%, 15%, 18%, or 20% w/w.

The concentration of manno-oligosaccharides with a degree of polymerization of six in a manno-oligosaccharide mixture may be about 5% to about 25% w/w. The concentration of manno-oligosaccharides with a degree of polymerization of six may be at least 5%, 8%, 10%, 12%, 15%, 18%, 20%, or 25% w/w.

The concentration of manno-oligosaccharides with a degree of polymerization of seven in a manno-oligosaccharide mixture may be about 2% to about 20% w/w. The concentration of manno-oligosaccharides with a degree of polymerization of seven may be at least 2%, 4%, 6%, 8%, 10%, 12%, 15%, 17%, or 20% w/w.

The concentration of manno-oligosaccharides with a degree of polymerization of eight in a manno-oligosaccharide mixture may be about 1% to about 15% w/w. The concentration of manno-oligosaccharides with a degree of polymerization of eight may be at least 1%, 2%, 3%, 4%, 5%, 6%, 7%, 8%, 9%, 10%, or 15% w/w.

The concentration of manno-oligosaccharides with a degree of polymerization of nine in a manno-oligosaccharide mixture may be about 2% to about 15% w/w. The concentration of manno-oligosaccharides with a degree of polymerization of nine may be at least 1%, 2%, 3%, 4%, 5%, 6%, 7%, 8%, 9%, 10%, or 15% w/w.

The concentration of manno-oligosaccharides with a degree of polymerization of ten in a manno-oligosaccharide mixture may be about 2% to about 15% w/w. The concentration of manno-oligosaccharides with a degree of polymerization of ten may be at least 1%, 2%, 3%, 4%, 5%, 6%, 7%, 8%, 9%, 10%, or 15% w/w.

The concentration of manno-oligosaccharides with a degree of polymerization of eleven in a manno-oligosaccharide mixture may be about 2% to about 15% w/w. The concentration of manno-oligosaccharides with a degree of polymerization of eleven may be at least 1%, 2%, 3%, 4%, 5%, 6%, 7%, 8%, 9%, 10%, or 15% w/w.

The concentration of manno-oligosaccharides with a degree of polymerization of twelve in a manno-oligosaccharide mixture may be about 2% to about 15% w/w. The concentration of manno-oligosaccharides with a degree of polymerization of twelve may be at least 1%, 2%, 3%, 4%, 5%, 6%, 7%, 8%, 9%, 10%, or 15% w/w.

The concentration of xyloglucan-oligosaccharides with a degree of polymerization of four in a xyloglucan-oligosaccharide mixture may be about 5% to about 20% w/w. The concentration of xyloglucan-oligosaccharides with a degree of polymerization of four may be at least 5%, 8%, 10%, 12%, 15%, 18%, or 20% w/w.

The concentration of xyloglucan-oligosaccharides with a degree of polymerization of five in a xyloglucan-oligosaccharide mixture may be about 5% to about 20% w/w. The concentration of xyloglucan-oligosaccharides with a degree of polymerization of five may be at least 5%, 7%, 8%, 10%, 12%, 15%, 18%, or 20% w/w.

The concentration of xyloglucan-oligosaccharides with a degree of polymerization of six in a xyloglucan-oligosaccharide mixture may be about 5% to about 25% w/w. The concentration of xyloglucan-oligosaccharides with a degree of polymerization of six may be at least 5%, 8%, 10%, 12%, 15%, 18%, 20%, or 25% w/w.

The concentration of xyloglucan-oligosaccharides with a degree of polymerization of seven in a xyloglucan-oligosaccharide mixture may be about 2% to about 20% w/w. The concentration of xyloglucan-oligosaccharides with a degree of polymerization of seven may be at least 2%, 4%, 6%, 8%, 10%, 12%, 15%, 17%, or 20% w/w.

The concentration of xyloglucan-oligosaccharides with a degree of polymerization of eight in a xyloglucan-oligosaccharide mixture may be about 1% to about 15% w/w. The concentration of xyloglucan-oligosaccharides with a degree of polymerization of eight may be at least 1%, 2%, 3%, 4%, 5%, 6%, 7%, 8%, 9%, 10%, or 15% w/w.

The concentration of xyloglucan-oligosaccharides with a degree of polymerization of nine in a xyloglucan-oligosaccharide mixture may be about 2% to about 15% w/w. The concentration of xyloglucan-oligosaccharides with a degree of polymerization of nine may be at least 1%, 2%, 3%, 4%, 5%, 6%, 7%, 8%, 9%, 10%, or 15% w/w.

The concentration of xyloglucan-oligosaccharides with a degree of polymerization of ten in a xyloglucan-oligosaccharide mixture may be about 2% to about 15% w/w. The concentration of xyloglucan-oligosaccharides with a degree of polymerization of ten may be at least 1%, 2%, 3%, 4%, 5%, 6%, 7%, 8%, 9%, 10%, or 15% w/w.

The concentration of mixed-linkage glucan-oligosaccharides with a degree of polymerization of two in a mixed-linkage glucan-oligosaccharide mixture may be about 2% to about 30% w/w. The concentration of mixed-linkage glucan-oligosaccharides with a degree of polymerization of two may be at least 2%, 4%, 6%, 8%, 10%, 12%, 15%, 18%, 20%, 25%, or 30% w/w.

The concentration of mixed-linkage glucan-oligosaccharides with a degree of polymerization of three in a mixed-linkage glucan-oligosaccharide mixture may be about 2% to about 20% w/w. The concentration of mixed-linkage glucan-oligosaccharides with a degree of polymerization of three may be at least 2%, 4%, 6%, 8%, 10%, 12%, 15%, 18%, or 20% w/W.

The concentration of mixed-linkage glucan-oligosaccharides with a degree of polymerization of four in a mixed-linkage glucan-oligosaccharide mixture may be about 5% to about 20% w/w. The concentration of mixed-linkage glucan-oligosaccharides with a degree of polymerization of four may be at least 5%, 8%, 10%, 12%, 15%, 18%, or 20% w/w.

The concentration of mixed-linkage glucan-oligosaccharides with a degree of polymerization of five in a mixed-linkage glucan-oligosaccharide mixture may be about 5% to about 20% w/w. The concentration of mixed-linkage glucan-oligosaccharides with a degree of polymerization of five may be at least 5%, 7%, 8%, 10%, 12%, 15%, 18%, or 20% w/w.

The concentration of chito-oligosaccharides with a degree of polymerization of two in a chito-oligosaccharide mixture may be about 2% to about 30% w/w. The concentration of chito-oligosaccharides with a degree of polymerization of two may be at least 2%, 4%, 6%, 8%, 10%, 12%, 15%, 18%, 20%, 25%, or 30% w/w.

The concentration of chito-oligosaccharides with a degree of polymerization of three in a chito-oligosaccharide mixture may be about 2% to about 20% w/w. The concentration of chito-oligosaccharides with a degree of polymerization of three may be at least 2%, 4%, 6%, 8%, 10%, 12%, 15%, 18%, or 20% w/w.

The concentration of chito-oligosaccharides with a degree of polymerization of four in a chito-oligosaccharide mixture may be about 5% to about 20% w/w. The concentration of chito-oligosaccharides with a degree of polymerization of four may be at least 5%, 8%, 10%, 12%, 15%, 18%, or 20% w/w.

The concentration of chito-oligosaccharides with a degree of polymerization of five in a chito-oligosaccharide mixture may be about 5% to about 20% w/w. The concentration of chito-oligosaccharides with a degree of polymerization of five may be at least 5%, 7%, 8%, 10%, 12%, 15%, 18%, or 20% w/w.

The concentration of chito-oligosaccharides with a degree of polymerization of six in a chito-oligosaccharide mixture may be about 5% to about 25% w/w. The concentration of chito-oligosaccharides with a degree of polymerization of six may be at least 5%, 8%, 10%, 12%, 15%, 18%, 20%, or 25% w/w.

The concentration of chito-oligosaccharides with a degree of polymerization of seven in a chito-oligosaccharide mixture may be about 2% to about 20% w/w. The concentration of chito-oligosaccharides with a degree of polymerization of seven may be at least 2%, 4%, 6%, 8%, 10%, 12%, 15%, 17%, or 20% w/w.

The concentration of chito-oligosaccharides with a degree of polymerization of eight in a chito-oligosaccharide mixture may be about 1% to about 15% w/w. The concentration of chito-oligosaccharides with a degree of polymerization of eight may be at least 1%, 2%, 3%, 4%, 5%, 6%, 7%, 8%, 9%, 10%, or 15% w/w.

The concentration of chito-oligosaccharides with a degree of polymerization of nine in a chito-oligosaccharide mixture may be about 2% to about 15% w/w. The concentration of chito-oligosaccharides with a degree of polymerization of nine may be at least 1%, 2%, 3%, 4%, 5%, 6%, 7%, 8%, 9%, 10%, or 15% w/w.

The concentration of chito-oligosaccharides with a degree of polymerization of ten in a chito-oligosaccharide mixture may be about 2% to about 15% w/w. The concentration of chito-oligosaccharides with a degree of polymerization of ten may be at least 1%, 2%, 3%, 4%, 5%, 6%, 7%, 8%, 9%, 10% or 15% w/w.

The concentration of chito-oligosaccharides with a degree of polymerization of eleven in a chito-oligosaccharide mixture may be about 2% to about 15% w/w. The concentration of chito-oligosaccharides with a degree of polymerization of eleven may be at least 1%, 2%, 3%, 4%, 5%, 6%, 7%, 8%, 9%, 10%, or 15% w/w.

The concentration of chito-oligosaccharides with a degree of polymerization of twelve in a chito-oligosaccharide mixture may be about 2% to about 15% w/w. The concentration of chito-oligosaccharides with a degree of polymerization of twelve may be at least 1%, 2%, 3%, 4%, 5%, 6%, 7%, 8%, 9%, 10%, or 15% w/w.

Compositions with Combinations of Polysaccharides and Oligosaccharides

A composition may comprise a combination of polysaccharides and oligosaccharides. The source of the polysaccharides in such compositions may contain cellulose, such as plant biomass, for example the undigested component of partially digested plant biomass, such as the undigested plant biomass from the same reaction as that which produced the oligosaccharides. The polysaccharides in the undigested biomass may comprise lignin, polyphenol, cellulose, lignocellulose, or any other suitable polysaccharides as described herein. Addition of polysaccharides to oligosaccharide mixtures can be done to improve the gastrointestinal tolerance of the oligosaccharide mixtures. Oligosaccharide consumption can cause gastrointestinal distress, including diarrhea, discomfort, and bloating. The compositions described herein may have an improved gastrointestinal tolerance such as, less or no discomfort, bloating, diarrhea or gastrointestinal distress as compared to a saccharide composition available commercially or a saccharide composition comprising primarily monosaccharides and/or disaccharides.

The concentration of undigested biomass in a composition may be 1% to 50% w/w. The concentration of undigested biomass in a composition may be 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of undigested biomass in a composition may be 1%, 5%, 10%, 15%, 20%, 25%, 30%, 35%, 40%, 45%, or 50% w/w. The concentration of undigested biomass in a composition may be at least 1%, 5%, 10%, 15%, 20%, 25%, 30%, 35%, 40%, or 45% w/w. The concentration of undigested biomass in a composition may be at most 5%, 10%, 15%, 20%, 25%, 30%, 35%, 40%, 45%, or 50% w/w.

The concentration of xylo-oligosaccharides in a composition may be 1% to 50% w/w. The concentration of xylo-oligosaccharides in a composition may be 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of xylo-oligosaccharides in a composition may be 1%, 5%, 10%, 15%, 20%, 25%, 30%, 35%, 40%, 45%, or 50% w/w. The concentration of xylo-oligosaccharides in a composition may be at least 1%, 5%, 10%, 15%, 20%, 25%, 30%, 35%, 40%, or 45% w/w. The concentration of xylo-oligosaccharides in a composition may be at most 5%, 10%, 15%, 20%, 25%, 30%, 35%, 40%, 45%, or 50% w/w.

The concentration of cello-oligosaccharides in a composition may be 1% to 50% w/w. The concentration of cello-oligosaccharides in a composition may be 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of cello-oligosaccharides in a composition may be 1%, 5%, 10%, 15%, 20%, 25%, 30%, 35%, 40%, 45%, or 50% w/w. The concentration of cello-oligosaccharides in a composition may be at least 1%, 5%, 10%, 15%, 20%, 25%, 30%, 35%, 40%, or 45% w/w. The concentration of cello-oligosaccharides in a composition may be at most 5%, 10%, 15%, 20%, 25%, 30%, 35%, 40%, 45%, or 50% w/w.

The concentration of manno-oligosaccharides in a composition may be 1% to 50% w/w. The concentration of manno-oligosaccharides in a composition may be 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of manno-oligosaccharides in a composition may be 1%, 5%, 10%, 15%, 20%, 25%, 30%, 35%, 40%, 45%, or 50% w/w. The concentration of manno-oligosaccharides in a composition may be at least 1%, 5%, 10%, 15%, 20%, 25%, 30%, 35%, 40%, or 45% w/w. The concentration of manno-oligosaccharides in a composition may be at most 5%, 10%, 15%, 20%, 25%, 30%, 35%, 40%, 45%, or 50% w/w.

The concentration of chito-oligosaccharides in a composition may be 1% to 50% w/w. The concentration of chito-oligosaccharides in a composition may be 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of chito-oligosaccharides in a composition may be 1%, 5%, 10%, 15%, 20%, 25%, 30%, 35%, 40%, 45%, or 50% w/w. The concentration of chito-oligosaccharides in a composition may be at least 1%, 5%, 10%, 15%, 20%, 25%, 30%, 35%, 40%, or 45% w/w. The concentration of chito-oligosaccharides in a composition may be at most 5%, 10%, 15%, 20%, 25%, 30%, 35%, 40%, 45%, or 50% w/w.

The concentration of xyloglucan-oligosaccharides in a composition may be 1% to 50% w/w. The concentration of xyloglucan-oligosaccharides in a composition may be 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of xyloglucan-oligosaccharides in a composition may be 1%, 5%, 10%, 15%, 20%, 25%, 30%, 35%, 40%, 45%, or 50% w/w. The concentration of xyloglucan-oligosaccharides in a composition may be at least 1%, 5%, 10%, 15%, 20%, 25%, 30%, 35%, 40%, or 45% w/w. The concentration of xyloglucan-oligosaccharides in a composition may be at most 5%, 10%, 15%, 20%, 25%, 30%, 35%, 40%, 45%, or 50% w/w.

The concentration of mixed-linkage glucan-oligosaccharides in a composition may be 1% to 50% w/w. The concentration of mixed-linkage glucan-oligosaccharides in a composition may be 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of mixed-linkage glucan-oligosaccharides in a composition may be 1%, 5%, 10%, 15%, 20%, 25%, 30%, 35%, 40%, 45%, or 50% w/w. The concentration of mixed-linkage glucan-oligosaccharides in a composition may be at least 1%, 5%, 10%, 15%, 20%, 25%, 30%, 35%, 40%, or 45% w/w. The concentration of mixed-linkage glucan-oligosaccharides in a composition may be at most 5%, 10%, 15%, 20%, 25%, 30%, 35%, 40%, 45%, or 50% w/w.

A composition may comprise polysaccharides and one or more oligosaccharides. The composition may comprise a polysaccharide and one type of oligosaccharide. The composition may comprise a polysaccharide and two forms of oligosaccharides. The composition may comprise a polysaccharide and three forms of oligosaccharides. The composition may comprise a polysaccharide and four forms of oligosaccharides. The composition may comprise a polysaccharide and five forms of oligosaccharides. The oligosaccharides may be xylo-oligosaccharides, cello-oligosaccharides, manno-oligosaccharides, xyloglucan-oligosaccharides, chito-oligosaccharides, or any other suitable oligosaccharides described herein.

The composition may comprise about 5% to 50% polysaccharides w/w; such as in the type of undigested biomass, and about 5% to about 95% oligosaccharides w/w. The composition of polysaccharides may be at least about 5%, 10%, 15%, 20%, 25%, 30%, 35%, 40%, 45%, or 50% w/w w/w. Oligosaccharides in such mixtures may be present at greater than 5%, 10%, 15%, 20%, 25%, 30%, 35%, 40%, 45%, 50%, 55%, 60%, 65%, 70%, 75%, 80%, 85%, 90%, or 95% w/w. The oligosaccharides may be a mixture of one or more oligosaccharides. For instance, a composition may comprise 5% undigested biomass and 50% oligosaccharide mixture w/w as described elsewhere herein.

The composition may comprise about 5% polysaccharides w/w; such as in the type of undigested biomass, and about 5% to about 95% oligosaccharides w/w. Oligosaccharides in such mixtures may be present at greater than 5%, 10%, 15%, 20%, 25%, 30%, 35%, 40%, 45%, 50%, 55%, 60%, 65%, 70%, 75%, 80%, 85%, 90% or 95% w/w. The oligosaccharides may be a mixture of one or more oligosaccharides. For instance, a composition may comprise 5% undigested biomass and 50% oligosaccharide mixture w/w as described elsewhere herein.

The composition may comprise about 7% polysaccharides w/w, such as in the type of undigested biomass and about 5% to about 93% oligosaccharides w/w. Oligosaccharides may form at least 5%, 10%, 15%, 20%, 25%, 30%, 35%, 40%, 45%, 50%, 55%, 60%, 65%, 70%, 75%, 80%, 85%, 90% or 93% w/w of such mixtures. The oligosaccharides may be a mixture of one or more oligosaccharides. For instance, a composition may comprise 7% undigested biomass and 50% oligosaccharide mixture w/w as described elsewhere herein.

The composition may comprise about 10% polysaccharides w/w; such as in the type of undigested biomass and about 5% to about 90% oligosaccharides w/w. Oligosaccharides may form at least 5%, 10%, 15%, 20%, 25%, 30%, 35%, 40%, 45%, 50%, 55%, 60%, 65%, 70%, 75%, 80%, 85% or 90% w/w of such mixtures. The oligosaccharides may be a mixture of one or more oligosaccharides. For instance, a composition may comprise 10% undigested biomass and 50% oligosaccharide mixture w/w as described elsewhere herein.

The composition may comprise about 12% polysaccharides w/w, such as in the type of undigested biomass and about 5% to about 95% oligosaccharides w/w. Oligosaccharides may form at least 5%, 10%, 15%, 20%, 25%, 30%, 35%, 40%, 45%, 50%, 55%, 60%, 65%, 70%, 75%, 80%, 85% or 88% w/w of such mixtures. The oligosaccharides may be a mixture of one or more oligosaccharides. For instance, a composition may comprise 12% undigested biomass and 50% oligosaccharide mixture w/w as described elsewhere herein.

The composition may comprise about 15% polysaccharides w/w, such as in the type of undigested biomass and about 5% to about 85% oligosaccharides w/w. Oligosaccharides may form at least 5%, 10%, 15%, 20%, 25%, 30%, 35%, 40%, 45%, 50%, 55%, 60%, 65%, 70%, 75%, 80% or 85% w/w of such mixtures. The oligosaccharides may be a mixture of one or more oligosaccharides. For instance, a composition may comprise 15% undigested biomass and 50% oligosaccharide mixture w/w as described elsewhere herein.

The composition may comprise about 20% polysaccharides w/w, such as in the type of undigested biomass and about 5% to about 80% oligosaccharides w/w. Oligosaccharides may form at least 5%, 10%, 15%, 20%, 25%, 30%, 35%, 40%, 45%, 50%, 55%, 60%, 65%, 70%, 75% or 80% w/w of such mixtures. The oligosaccharides may be a mixture of one or more oligosaccharides. For instance, a composition may comprise 20% undigested biomass and 50% oligosaccharide mixture w/w as described elsewhere herein.

The composition may comprise about 25% polysaccharides w/w, such as in the type of undigested biomass and about 5% to about 75% oligosaccharides w/w. Oligosaccharides may form at least 5%, 10%, 15%, 20%, 25%, 30%, 35%, 40%, 45%, 50%, 55%, 60%, 65%, 70% or 75% w/w of such mixtures. The oligosaccharides may be a mixture of one or more oligosaccharides. For instance, a composition may comprise 25% undigested biomass and 50% oligosaccharide mixture w/w as described elsewhere herein.

The composition may comprise about 30% polysaccharides w/w, such as in the type of undigested biomass and about 5% to about 70% oligosaccharides w/w. Oligosaccharides may form at least 5%, 10%, 15%, 20%, 25%, 30%, 35%, 40%, 45%, 50%, 55%, 60%, 65% or 70% w/w of such mixtures. The oligosaccharides may be a mixture of one or more oligosaccharides. For instance, a composition may comprise 30% undigested biomass and 50% oligosaccharide mixture w/w as described elsewhere herein.

The composition may comprise about 40% polysaccharides w/w, such as in the type of undigested biomass and about 5% to about 60% oligosaccharides w/w. Oligosaccharides may form at least 5%, 10%, 15%, 20%, 25%, 30%, 35%, 40%, 45%, 50%, 55% or 60% w/w of such mixtures. The oligosaccharides may be a mixture of one or more oligosaccharides. For instance, a composition may comprise 40% undigested biomass and 50% oligosaccharide mixture w/w as described elsewhere herein.

The composition may comprise about 50% polysaccharides w/w, such as in the type of undigested biomass and about 5% to about 50% oligosaccharides w/w. Oligosaccharides may form at least 5%, 10%, 15%, 20%, 25%, 30%, 35%, 40%, 45% or 50% w/w of such mixtures. The oligosaccharides may be a mixture of one or more oligosaccharides. For instance, a composition may comprise 50% undigested biomass and 50% oligosaccharide mixture w/w as described elsewhere herein.

Use of Compositions as Ingredients

In some embodiments, the composition is an ingredient. As used herein, "ingredient" is any composition suitable for incorporation into a foodstuff, cosmetic, or nutraceutical product, which may include those which are used directly as the product itself.

In some embodiments, the ingredient comprises at least 50%, 60%, 70%, 80%, 90%, 95%, 99%, 99.5% by dry weight of saccharide present. The ingredient may consist essentially of saccharides. As used herein, "consist essentially of" means that the material (for instance the ingredient) has less than 0.5% by dry weight, such as 0.3% by dry weight, for instance 0.1% by dry weight, of other substances.

The ingredient may comprise an oligosaccharide mixture as described elsewhere herein. The ingredient may comprise at least two of the oligosaccharides. For instance, it may comprise three of the oligosaccharides. It may comprise four oligosaccharides. It may comprise five oligosaccharides. It may comprise six oligosaccharides.

In some embodiments, the ingredient comprises cello-oligosaccharides, for instance cello-oligosaccharides in combination with the xylo-oligosaccharides. An alternative ingredient may comprise cello-oligosaccharides in combination with manno-oligosaccharides.

Ingredients may be used to prepare finished products. The ingredient may also be treated in some physical or chemical way before or during incorporation into a foodstuff, cosmetic, or nutraceutical. It may be directly incorporated into a product, or it may be incorporated into, for example, a dough, cake mixture, chocolate mixture, or other foodstuff precursor: a cosmetic base composition; or a nutraceutical, and be optionally cooked or otherwise treated in a way which may cause chemical modification, a change of texture a change of colour, or other modification.

A foodstuff, cosmetic, or nutraceutical may be produced from an ingredient described herein. For example, in the food industry the saccharide formulations produced by the current method may be used as sweeteners, bulking agents, added dietary fibre, or humectants. The ingredient may be used as a sugar substitute. The ingredient may be incorporated into cakes, bread, or other baked goods, or into chocolate or other confectionery such as toffee, fudge, meringue, jam, jelly or caramel; or drinks, for example, to provide favourable taste or colour characteristics or to increase dietary fibre content. Or they may be incorporated into animal feed, for example either as an isolated ingredient or by utilising the enzymatic reaction mixture directly as feed.

In the cosmetics industry, saccharides can be useful as ingredients, as they may improve texture and moisture retention, act as UV-absorbing molecules, maintain a gel or cream structure, and/or serve as bulking agents. The compositions described herein can be incorporated into nutraceutical compositions, as the dietary fibre they provide has been shown to encourage digestive health, well-regulated gut flora, and other benefits to wellbeing. In this context, they may also function as an ingredient in a probiotic drink or other prebiotic or probiotic formulation.

Compositions or ingredients as described herein may be used to alter one or more properties of the finished product. Such properties include, but are not limited to, sweetness, texture, mouthfeel, binding, glazing, smoothness, moistness, viscosity, color, hygroscopicity, flavor, bulking, water-retention, caramelization, surface texture, crystallization, structural properties and dissolution.

In some cases, the compositions and/or ingredients described herein may provide a property to a finished product which is comparable to or better than the same property as provided by a saccharide mixture comprising primarily monosaccharides and/or disaccharides. The control composition may be a saccharide used commonly in consumables, for instance, a monosaccharide composition such as glucose, fructose, etc, a disaccharide composition such as sucrose or an artificial sugar composition. The term "comparable" as used herein may mean that the two compositions may be up to 100%, up to 95%, up to 90%, up to 80% identical. For instance, comparable can mean that the composition is up to 90% identical to the control composition.

In some cases, the compositions described herein may be used as sweetener compositions. Sweetener compositions may be used by themselves or as an ingredient in a finished product. The compositions described herein may provide about the same level of sweetness or greater sweetness than an identical amount of a control composition wherein the control composition comprises primarily monosaccharides and/or disaccharides. The compositions described herein may be used to replace the control composition as the sweetener in a finished product. In some cases, the sweetness of a composition may be 5%, 10%, 15%, 20%, 30%, 40%, 50%, 70%, 80%, 90% or 100% more than an identical amount of the control composition.

The compositions described herein may provide a comparable flavor profile or better flavor profile than an identical amount of a control composition wherein the control composition comprises primarily monosaccharides and/or disaccharides. The compositions described herein may be used to replace the control composition as a flavor enhancer in a finished product. In some cases, the flavor of a composition may be 5%, 10%, 15%, 20%, 30%, 40%, 50%, 70%, 80%, 90% or 100% more than an identical amount of the control composition.

The compositions described herein may provide a comparable texture profile or better texture profile than an identical amount of a control composition wherein the control composition comprises primarily monosaccharides and/or disaccharides. The compositions described herein may be used to replace the control composition as a texture enhancer in a finished product.

The compositions described herein may provide a comparable binding profile or better binding profile than an identical amount of a control composition wherein the control composition comprises primarily monosaccharides and/or disaccharides. The compositions described herein may be used to replace the control composition as a binding enhancer in a finished product.

The compositions described herein may provide a comparable glazing profile or better glazing profile than an identical amount of a control composition wherein the control composition comprises primarily monosaccharides and/or disaccharides. The compositions described herein may be used to replace the control composition as a glazing enhancer in a finished product.

The compositions described herein may provide a comparable moistness or better moistness than an identical amount of a control composition wherein the control composition comprises primarily monosaccharides and/or disaccharides. The compositions described herein may be used to replace the control composition to provide moistness in a finished product.

The compositions described herein may provide a comparable color profile or better color profile than an identical amount of a control composition wherein the control composition comprises primarily monosaccharides and/or disaccharides. The compositions described herein may be used to replace the control composition as a color enhancer in a finished product.

The compositions described herein may provide a comparable dissolution profile or better dissolution profile than an identical amount of a control composition wherein the control composition comprises primarily monosaccharides and/or disaccharides. The compositions described herein may be used to replace the control composition as a dissolution enhancer in a finished product. In some cases, the dissolution of a composition may be 5%, 10%, 15%, 20%, 30%, 40%, 50%, 70%, 80%, 90% or 100% more than an identical amount of the control composition.

The compositions described herein may provide a comparable mouthfeel or better mouthfeel than an identical amount of a control composition wherein the control composition comprises primarily monosaccharides and/or disaccharides.

The compositions described herein may provide a comparable viscosity or better viscosity than an identical amount of a control composition wherein the control composition comprises primarily monosaccharides and/or disaccharides.

The compositions described herein may provide a comparable hygroscopicity or better hygroscopicity than an identical amount of a control composition wherein the control composition comprises primarily monosaccharides and/or disaccharides. In some cases, the hygroscopicity of a composition may be 5%, 10%, 15%, 20%, 30%, 40%, 50%, 70%, 80%, 90% or 100% more than an identical amount of the control composition.

The compositions described herein may provide a comparable water-retention or better water-retention than an identical amount of a control composition wherein the control composition comprises primarily monosaccharides and/or disaccharides. In some cases, the water-retention of a composition may be 5%, 10%, 15%, 20%, 30%, 40%, 50%, 70%, 80%, 90% or 100% more than an identical amount of the control composition.

The compositions described herein may provide a lower calorie composition than an identical amount of a control composition wherein the control composition comprises primarily monosaccharides and/or disaccharides. In some cases, the calorie count of a composition may be 5%, 10%, 15%, 20%, 30%, 40%, 50%, 70%, 80%, 90% or 100% less than an identical amount of the control composition.

The compositions described herein may provide a lower glycemic index than an identical amount of a control composition wherein the control composition comprises primarily monosaccharides and/or disaccharides. In some cases, the glycemic index of a composition may be 5%, 10%, 15%, 20%, 30%, 40%, 50%, 70%, 80%, 90% or 100% less than an identical amount of the control composition.

The compositions described herein may provide a comparable bulking or better bulking than an identical amount of a control composition wherein the control composition comprises primarily monosaccharides and/or disaccharides.

The compositions described herein may provide a comparable caramelization or better caramelization than an identical amount of a control composition wherein the control composition comprises primarily monosaccharides and/or disaccharides.

The compositions described herein may provide a comparable surface texture or better surface texture than an identical amount of a control composition wherein the control composition comprises primarily monosaccharides and/or disaccharides.

The compositions described herein may provide a comparable crystallization or better crystallization than an identical amount of a control composition wherein the control composition comprises primarily monosaccharides and/or disaccharides.

The compositions described herein may provide comparable structural properties as an identical amount of a control composition wherein the control composition comprises primarily monosaccharides and/or disaccharides.

The compositions described herein may provide less aftertaste compared to an identical amount of a control composition wherein the control composition comprises primarily monosaccharides and/or disaccharides.

Different compositions of oligosaccharides may have improved dissolution profiles, hygroscopicity profiles, and taste profiles compared to the oligosaccharides used alone.

The compositions or ingredients as described herein may be used to increase the fibre content of a finished product such as a foodstuff or a nutraceutical. The compositions may provide a higher level of fibre in the finished product as compared to an identical amount of a control composition wherein the control composition comprises primarily monosaccharides and/or disaccharides. In some cases, the compositions may improve the fibre content of the finished product without negatively affecting any other properties such as taste, sweetness, mouthfeel, texture, binding, or any other properties described herein. In some cases, the fibre content of a composition may be 5%, 10%, 15%, 20%, 30%, 40%, 50%, 70%, 80%, 90% or 100% more than an identical amount of the control composition.

Ingredients may be used to alter the properties of a finished product such as foodstuff or nutraceutical or cosmetic. In order to alter the properties of the finished products, the finished products may additionally comprise a polysaccharide, preferably a cellulosic polysaccharide, such as cellulose, or a polysaccharide derivative, preferably a cellulose derivative, such as carboxymethylcellulose, or a polysaccharide aggregate, preferably a portion of lignocellulosic biomass. Suitably, the finished products can comprise from greater than 0% to 40% by dry weight of polysaccharide, polysaccharide derivative, or polysaccharide aggregate, preferably from greater than 1% to 30% by dry weight of polysaccharide, polysaccharide derivative, or polysaccharide aggregate, preferably from greater than 5% to 25% by dry weight of polysaccharide, polysaccharide derivative, or polysaccharide aggregate, preferably from greater than 10% to 20% by dry weight of polysaccharide, polysaccharide derivative, or polysaccharide aggregate.

The concentration of a composition comprising polysaccharides and a mixture of oligosaccharides in a finished product may be anywhere from 0.1% to 40% w/w. The concentration of a composition comprising polysaccharides and a mixture of oligosaccharides in a finished product may be about 0.1% to about 0.5%, about 0.1% to about 1%, about 0.1% to about 5%, about 0.1% to about 10%, about 0.1% to about 15%, about 0.1% to about 20%, about 0.1% to about 25%, about 0.1% to about 30%, about 0.1% to about 35%, about 0.1% to about 40%, about 0.5% to about 1%, about 0.5% to about 5%, about 0.5% to about 10%, about 0.5% to about 15%, about 0.5% to about 20%, about 0.5% to about 25%, about 0.5% to about 30%, about 0.5% to about 35%, about 0.5% to about 40%, about 1% to about 5%, about 1% to about 10%, about 1% to about 15%, about 1% to about 20%, about 1% to about 25%, about 1% to about 30%, about 1% to about 35%, about 1% to about 40)%, about 5% to about 10%, about 5% to about 15%, about 5% to about 20%, about 5% to about 25%, about 5% to about 30%, about 5% to about 35%, about 5% to about 40%, about 10% to about 15%, about 10% to about 20%, about 10% to about 25%, about 10% to about 30%, about 10% to about 35%, about 10% to about 40%, about 15% to about 20%, about 15% to about 25%, about 15% to about 30%, about 15% to about 35%, about 15% to about 40%, about 20% to about 25%, about 20% to about 30%, about 20% to about 35%, about 20% to about 40%, about 25% to about 30%, about 25% to about 35%, about 25% to about 40%, about 30% to about 35%, about 30% to about 40%, or about 35% to about 40% w/w. The concentration of a composition comprising polysaccharides and a mixture of oligosaccharides in a finished product may be about 0.1%, about 0.5%, about 1%, about 5%, about 10%, about 15%, about 20%, about 25%, about 30%, about 35%, or about 40% w/w. The concentration of a composition comprising polysaccharides and a mixture of oligosaccharides in a finished product may be at least 0.1%, 0.5%, 1%, 5%, 10%, 15%, 20%, 25%, 30%, or 35% w/w. The concentration of a composition comprising polysaccharides and a mixture of oligosaccharides in a finished product may be at most 0.5%, 1%, 5%, 10%, 15%, 20%, 25%, 30%, 35%, or 40% w/w.

Enzymatic Reactions

One step of the method of forming or manufacturing the composition??? may be an enzymatic reaction, in which one or more enzymes are placed in a suitable reaction vessel together with one or more feedstocks, which may be soluble or insoluble in water, and a suitable solvent.

A variety of enzymes may be suitable for use in the enzymatic reaction. Any enzyme which produces oligosaccharides when acting on a polysaccharide-containing feedstock may be appropriate, and it is within the ability of the skilled person to select suitable enzymes. Preferably, the enzymatic reaction comprises a cellulase, an endo-glucanase, a cellobiohydrolase, a lytic polysaccharide monooxygenase (LPMO), a lichenase, a xyloglucan endoglucanase (XEG), a mannanase, a chitinase, and/or a xylanase.

More preferably, the enzymatic reaction comprises a cellulolytic preparation from a species, such as *Trichoderma reesei*, which may be purified and/or pre-treated and/or may be supplemented with one or more additional enzymes, for example, adding a beta-glucanase (SEQ ID NO: 14), a beta-xylanase (SEQ ID NO: 16) and a cellobiohydrolase, or a beta-glucanase, a beta-xylanase, an LPMO and a cellobiohydrolase, or an LPMO and a xylanase, or an LPMO, a xylanase, and a lichenase. Each enzyme may be provided to the enzymatic reaction as a purified enzyme, a semi-purified mixture derived from some natural source or lab-grown culture, in the form of a microbial strain engineered to produce the enzyme, or in any other manner. Fusions of these enzymes, either with other enzymes or with non-enzymatic modules such as carbohydrate-binding modules (CBMs), are also envisaged within each respective term, for example, an LPMO fused to a CBM, a xylanase fused to a CBM, or a xylanase fused to an LPMO.

As used herein, "cellulase" refers to an enzyme that has, or a group of enzymes that collectively have, hydrolytic activity against cellulose, for example, an enzyme preparation containing endo-1,4-beta-glucanase, cellobiohydrolase, and/or beta-glucosidase activities. Such enzymes may be able to cleave glycosidic bonds in one or more forms of cellulose, including cellulose found in plant biomass. In doing so, they can produce products including glucose and cello-oligosaccharides.

As used herein, "cellobiohydrolase" refers to an enzyme that has hydrolytic activity against cellulose and produces mainly cellobiose as a product. Cellobiose is a disaccharide and is a cello-oligosaccharide. Such enzymes are able to cleave glycosidic bonds in one or more forms of cellulose, including cellulose found in plant biomass. Preferable cellobiohydrolases are from the GH6 and GH7 enzyme families, such as cellobiohydrolase 12 and 13 from *Aspergillus niger* (SEQ ID NO:20 and 21) more preferably, Cel6A or Cel7A enzymes derived from *Trichoderma reesei* (SEQ ID NOs: 10 and 11).

As used herein, "beta-glucosidase" refers to an enzyme that has hydrolytic activity against cellulose and produces mainly glucose as a product. Such enzymes are able to cleave glycosidic bonds in one or more forms of cellulose, including cellulose found in plant biomass. Preferred beta-glucosidases include GH3 beta-glucosidases from *Trichoderma reesei* (SEQ ID NO:22).

As used herein, "lytic polysaccharide monooxygenase" and "LPMO" refer to a class of enzymes able to oxidatively cleave polysaccharides using a copper comprising moiety and using an oxygen source, such as a molecule of dioxygen, peroxide, or any other oxygen source; and a suitable reducing agent. As such, when an LPMO is used, the enzymatic reaction may be carried out under aerobic conditions. Suitable reducing agents are not particularly limited, but examples include ascorbic acid, gallic acid, cysteine, NADH, NADPH, pyrogallol, dithiothreitol, cyanoborohydrides, borohydrides, photosynthetic pigments, lignin, lignols, and a combination of cellobiose and cellobiose dehydrogenase. While the skilled person knows a wide variety of photosynthetic pigments which may be used, thylakoids and purified fractions, or chlorophyllin, are preferred, and light may be supplied. Preferably, LPMOs are selected from the following families: AA9, AA10, AA11, AA13, AA14, and AA15. More preferably, the LPMO is PaLPMO9E (SEQ ID NO:1), an AA9 LPMO originally isolated from the ascomycete fungus *Podospora anserina*. More preferably still, the LPMO is an AA9 LPMO from *Trichoderma reesei* (SEQ ID NO:25).

Aerobic conditions may comprise the addition of oxygen, which may be provided by aeration of the substrate mixture with an oxygen-comprising gas, such as air. Aeration may be conducted by the introduction of oxygen-comprising air bubbles into the aqueous substrate mixtures by various systems, such as an air-injector, an aeration frit, a membrane system, or an internal-loop airlift reactor. Preferably, the concentration of molecular oxygen in the enzymatic reaction is from about 4 mg/L to about 14 mg/L.

Another exemplary enzyme is a lichenase, which may be selected from the GH5, GH7, GH8, GH9, GH12, GH16, GH17, or GH26 families, preferably a GH16 enzyme, more preferably a GH16 enzyme derived from *Bacillus subtilis* (SEQ ID NO:2). The enzyme may be able to act on, for example, mixed-linkage glucans, which are glucans comprising a mixture of β-1,3 and β-1,4 linkages, and may cleave them at β-1,4 glycosidic bonds. In the preferable case in which the lichenase acts on a mixed-linkage glucan, the β-glucans produced may fall largely within the size range of from 3 to about 7 residues, so they are particularly useful in the food, cosmetics, and nutraceutical industries. Mixed-linkage glucans are abundant in members of the grass and horsetail families, and as such, grass-based feedstocks such as straw have high levels of mixed-linkage glucans and may be acted upon usefully with lichenases. Preferred lichenases include GH5 lichenase from *Bacillus subtilis* (SEQ ID NO:2).

Another alternative enzyme is a xylanase, which may act on, for example, feedstocks comprising a xylan backbone. The xylanase may be, for example, a glucuronoxylanase, an arabinoxylanase, or a glucuronoarabinoxylanase. The enzyme may be active on a variety of polymers having a xylan backbone, such as glucuronoxylan, arabinoxylan, and glucuronoarabinoxylan. These polymers are abundant in various plant-derived feedstocks, for example, both hardwood and softwood may comprise appropriate polysaccharides, with hardwood often comprising glucuronoxylan and softwood often comprising arabinoglucuronoxylan. Preferred xylanases include GH5 xylanases from *Ruminiclostridium thermocellum* (SEQ ID NO:3) and *Gonapodya prolifera* (SEQ ID NO:4), and GH30 xylanases from *Dickeya chrysanthemi* (SEQ ID NO:5), *Bacillus subtilis* (SEQ ID NO:6) and *Bacteroides ovatus* (SEQ ID NO:7) and *Trichoderma reesei* (SEQ ID NO:15 and 16).

Another alternative enzyme is a mannanase, which may act on, for example, feedstocks comprising a mannan backbone. The mannanase may be, for example, a mannanase, an glucomannanase, a galactomannanase or a galactoglucomannanase. The enzyme may be active on a variety of polymers having a mannan backbone, such as mannan, glucomannan, galactomannan or galactoglucomannan. These polymers are abundant in various plant-derived feedstocks, for example both hardwood and softwood may comprise appropriate polysaccharides. Preferred mannanases include GH5 mannanases from *Trichoderma reesei* (SEQ ID NO:17) and *Aspergillus niger* (SEQ ID NO:19) and a GH26 mannanase from *Aspergillus niger* (SEQ ID NO:18).

Other enzymes include xyloglucanases and xyloglucan endoglucanases (XEGs), which are produced by numerous organisms, including plant-pathogenic microbes. Xyloglucanases and XEGs may be able to act on xyloglucan, a hemicellulosic β-1,4 glucan chain abundant in the primary cell wall of higher plants, which is decorated with xylose, some of the xylose residues being further decorated with other residues, such as galactose. When appropriate xyloglucanases or XEGs act on xyloglucan, the products may comprise xyloglucan oligosaccharides having a main chain of a length useful in the foodstuff, cosmetics, and nutraceutical industries. Preferred xyloglucanases include is a GH5 xyloglucanase from *Bacteroides ovatus* (SEQ ID NO:8), and a GH74 xyloglucanase from *Trichoderma reesei* (SEQ ID NO:9).

Enzymes used in such enzymatic reactions may have a sequence which has at least 70%, 75%, 80%, 85%, 90%, 95%, or 100% identity to a sequence of SEQ ID Nos: 1-25.

Enzymes used herein may be functional equivalents of enzymes described herein or functional equivalents of SEQ ID Nos: 1-25.

The enzymatic reaction may take place in solution and/or suspension or in a suitable reaction vessel. At a temperature or temperature protocol appropriate for the particular combination of enzyme and feedstock, the reaction may be allowed to progress for a certain amount of time (e.g., a predetermined amount of time), until the products have reached a desired concentration, or until some other requirement has been met.

As used herein, "suspension" refers to a composition comprising at least two immiscible phases, for example, a solid and a liquid phase, wherein the weight of the solid phase may be, as a percentage of the weight of the composition, in the range of from 0.5% to 30%, preferably from 1% to 20%, more preferably from 2% to 15%, yet more preferably from 3% to 10%. The suspension may comprise a suitable solvent, which is preferably water.

In order to ensure optimal contact between the enzymes and feedstock, the reaction mixture may be agitated, either constantly or at intervals. The agitation may take the form of (i) rhythmically moving the entire reaction vessel, (ii) a fan or other stirring device, (iii) a bubble spurging, or any other suitable method of agitation.

The enzymatic reaction may be a microbial fermentation. The temperature and reaction time may be suitable for the growth of the microbial organism used. The microbial organism may be genetically altered to produce an enzyme suitable for the production of an oligosaccharide composition. The microbe may be, for example, a bacterium, for example *Escherichia coli*, or a fungus, such as *Saccharomyces cerevisiae* or *Trichoderma reesei*.

In some embodiments, an expression vector suitable for modifying the subject microorganism may be used such that it produces an enzyme or mixture of enzymes as described elsewhere herein. Where desired, the expression vector, which may be a plasmid or any other nucleic acid able to induce production of the enzyme, may comprise one or more of the following regulatory sequences so as to control the expression of the exogenous enzyme: regulatory sequences of a heat shock gene, regulatory sequences of a toxicity gene, regulatory sequences of a spore formation gene, or any other suitable regulatory sequence.

The enzymatic reaction can be carried out at a temperature or temperature protocol appropriate to the enzymes and substrates used. For example, the enzymatic reaction may be carried out at a constant temperature in the range of from 10° C. to 100° C., preferably from 20° C. to 80° C., more preferably from 40° C. to 60° C. If the enzymatic reaction takes the form of a microbial fermentation the temperature may be appropriate for such, for example, the enzymatic reaction may comprise the growth of *E. coli* and/or the temperature may be substantially constant and about 37° C.

The pH of the solution or suspension may affect the activity of the enzymes. Control of pH may aid in assuring that an enzymatic reaction proceeds at a suitable rate. The enzymatic reaction may take place at a pH in the range of from 2 to 10, preferably 3 to 8, more preferably 4 to 6.

The enzymatic reaction may be allowed to continue for a certain time period before optionally being quenched and the products isolated or otherwise collected. This time period may be from 1 minute to 6 days, and is preferably from 0.5 days to 5 days, more preferably from 16 hours to 96 hours. The reaction may alternatively be allowed to proceed until no further catalysis occurs.

The one or more feedstocks added to the enzymatic reaction may comprise polysaccharides. Such polysaccharides may have been produced by a separate reaction proceeding simultaneously or substantially simultaneously in the reaction vessel. The polysaccharides present in the enzymatic reaction may be partially cleaved by enzymes into useful oligosaccharides, leaving partially cleaved or uncleaved polysaccharides, which may include, but are not limited to, cellulose, xylan (such as glucuronoxylan, arabinoxylan, or glucuronoarabinoxylan), mannan (such as glucomannan, galactomannan, or galactoglucomannan), mixed-linkage glucan, xyloglucan chitin, chitosan, or lignocellulose.

The enzymatic reaction may be allowed to continue to run until there is from 5% to 75% undigested polysaccharide-containing feedstocks remaining, preferably 5% to 70%, preferably 5% to 65%, more preferably 5% to 55%, or more preferably 10% to 50%. This can be monitored or checked by reducing end assays, such as the anthrone assay and/or by chromatographic methods such as thin-layer chromatography and/or high-performance anion exchange chromatography.

Any substance which comprises appropriate polysaccharides may form part of the feedstock. As the foodstuff, cosmetic, and nutraceutical industries generally use a broad variety of oligosaccharides, the polysaccharides appropriate for taking part in the enzymatic reaction are not particularly limited. Feedstocks suitable for producing the oligosaccharide profile may comprise, for example, cellulose, lignocellulose, chitin, chitosan, xylan (such as glucuronoxylan, arabinoxylan, and glucuronoarabinoxylan) and/or mannan (such as glucomannan, galactomannan, or galactoglucomannan), however, any feedstock which can be suitably acted upon is envisaged. Preferably the feedstocks comprise sugar cane, corn stover, corn cob, wheat bran, wheat straw, hardwood, or softwood.

The feedstocks comprising such polysaccharides are also not particularly limited, as most plant matter is rich in such polymers. As such, the feedstock may comprise plant biomass such as grain, grain chaff, bean pods, seed coats, and/or other seed materials: seaweeds: corn stover, straw; bagasse, *miscanthus*, sorghum residue, switch grass, bamboo, and/or other monocotyledonous tissue: water hyacinth, leaf tissue, roots, and/or other vegetative matter: hardwood, hardwood chips, hardwood pulp, softwood, softwood chips, softwood pulp, paper, paper pulp, cardboard, and/or other wood-based feedstocks: crab shells, squid biomass, shrimp shells, and/or other marine biomass, and/or any combination of appropriate feedstocks. Preferably, the feedstock comprises wheat straw or wood. As any given natural feedstock is likely to comprise a mixture of different polysaccharides, it will sometimes be the case that a mixture of different enzymes is beneficial. Such a mixture may comprise one or more of any other enzyme. For example, such a mixture might comprise an LPMO with an endo-glucanase, a xylanase with a lichenase, a cellobiohydrolase with a mannanase, or an endo-glucanase with a cellobiohydrolase, in which the enzyme partners are present in molar ratios preferably from 1:100 to 100:1. In addition, as many appropriate feedstocks are recalcitrant, pre-treatment of the feedstock is envisaged.

As used herein, "pre-treatment" is any process which makes a feedstock more easily acted upon by the enzymes inherent in the enzymatic reaction step. The pre-treatment can occur before the enzymatic reaction, and may comprise acid treatment by, for example, sulphuric acid, phosphoric acid, or trifluoroacetic acid: alkali treatment by, for example, potassium hydroxide, sodium hydroxide, or ammonia fibre expansion: heat treatment by, for example, hot water, hot steam, or hot acid: ionic liquid treatment, and related technologies: Alcell pulping, and related technologies: supercritical solvent, such as supercritical water treatment; and/or enzyme treatment by, for example, a hydrolase, lyase, or LPMO, or any mixture of the above processes.

After the enzymatic reaction has progressed to a desired point, the one or more oligosaccharides and the one or more polysaccharides from the enzymatic reaction mixture are separated. This process can be performed in a variety of ways depending on the composition of the biomass used and the specificity of the enzymes used. As the reaction mixture will often comprise a mixture of soluble oligosaccharides and insoluble polysaccharides, the reaction mixture may be filtered to remove insoluble matter and prepare the soluble oligosaccharide obtained for further processing.

When used herein and otherwise unqualified, "soluble," "solubility," and grammatical variants refer to solubility in water.

The oligosaccharides may also be separated from the polysaccharides in a number of ways. They may be isolated based on solubility, so that a composition of soluble saccharides only is extracted for further processing, and/or isolated chromatographically to produce a composition with a narrower band of oligosaccharide chain lengths. Isolation may, for example, be based on precipitation, size-exclusion chromatography, ion-exchange chromatography, or filtration, ultrafiltration, or nanofiltration. In the case that isolation based on solubility is carried out, the profile of saccharides present in the isolated composition will depend on the original enzymatic reaction, as different polysaccharides decrease in solubility with length at different rates.

Also envisaged is the further treatment of all or part of the produced oligosaccharides to produce further products before incorporation into a foodstuff, cosmetic, or nutraceutical. This further treatment may comprise any chemical, physical, or enzymatic step, such as reduction, preferably reductive amination where appropriate: oxidation, caramelisation, modification with a Schiff base, or via the Maillard reaction, or by any combination of such steps, and may provide different products having properties which are improved for the desired purpose. For example, the caramelisation properties, calorific value, flavour, and colour may be modified. The oligosaccharides may also be purified, for example, through precipitation, size-exclusion chromatography, ion-exchange chromatography, or filtration, ultrafiltration, or nanofiltration.

Also envisaged is the further treatment of all or part of the produced polysaccharide fraction to produce products with improved properties before incorporation into a foodstuff, cosmetic, or nutraceutical. This further treatment may comprise any chemical, physical, or enzymatic step, such as alkylation or acid-treatment. The polysaccharides may also be purified, for example, through precipitation, size-exclusion chromatography, ion-exchange chromatography, or filtration, ultrafiltration, or nanofiltration.

Following optional modification and/or purification of the oligosaccharide and polysaccharide fractions, all or part of the fractions are then recombined at a ratio of from 1:100 to 1:1 polysaccharide:oligosaccharide, preferably from 1:10 to 1:1, preferably from 1:90 to 1:2, preferably from 1:80 to 1:3, preferably from 1:70 to 1:4, or preferably from 1:60 to 1:5. The specific ratio may depend on the desired properties of the final ingredient as well as the modifications and purifications that have been applied to the fractions. It may not be required to recombine all of the oligosaccharide and polysaccharide isolated from the enzymatic reaction. An example of a composition that can be generated by recombination of oligosaccharides is shown in FIG. 1. As shown in FIG. 1, the composition can have one or more oligosaccharides, wherein each type of oligosaccharide may have oligosaccharides with varying degrees of polymerization.

The fractions can be recombined in a variety of ways, for example, by mixing a solution comprising all or part of the oligosaccharide fraction and a solution and/or suspension comprising all or part of the polysaccharide fraction, which may further be spray-dried. lyophilised, or condensed in some other way. The fractions may also be recombined by mixing a dry form comprising all or part of the oligosaccharide fraction produced by spray-drying, lyophilisation, or condensation in some other way, with a dry form comprising all or part of the polysaccharide fraction, produced by spray-drying, lyophilisation, or condensation in some other way.

The oligosaccharide components of the final composition may comprise one or more of any type of oligosaccharide. Preferably they comprise cello-oligosaccharides, xylo-oligosaccharides, mixed-linkage glucan oligosaccharides, manno-oligosaccharides, xyloglucan oligosaccharides or chito-oligosaccharides, or derivatives of any of the aforementioned oligosaccharides.

Any such dry or liquid composition may be deemed an ingredient suitable for incorporation into a foodstuff, cosmetic, or nutraceutical at any stage of this process. This includes compositions that may be deemed to be an intermediate during the method, such as a composition formed after the recombining of the oligosaccharide and polysaccharide fractions prior to any further purification, optimisation, drying, dissolving, or any other such steps, as well as including the final composition obtained from the method.

As described herein, dry compositions may be formed by well-known methods in the art such as spray-drying and/or lyophilisation. The dry compositions can be dissolved into a solution of various liquids including water, syrups, pastes, solvents, alcohols, etc. to form the liquid composition ingredient suitable for incorporation into a foodstuff, cosmetic, or nutraceutical. Liquid compositions may be particularly useful in foods that require a smooth texture such as candy, chocolate, and yoghurts.

Following optional modification and/or purification of the oligosaccharide and polysaccharide fractions, all or part of the fractions may then be recombined at a ratio of from 1:100 to 1:1 polysaccharide:oligosaccharide, preferably from 1:10 to 1:1, preferably from 1:90 to 1:2, preferably from 1:80 to 1:3, preferably from 1:70 to 1:4, or preferably from 1:60 to 1:5. The specific ratio may depend on the desired properties of the final ingredient as well as the modifications and purifications that have been applied to the fractions.

Once a composition of the oligosaccharide products suitable for the application being considered is obtained, and further treatment and/or isolation is optionally carried out, the derivation of a foodstuff, cosmetic, or nutraceutical from the composition can furnish a very broad array of potential uses. The ingredients as described herein, can be useful in applications in which oligosaccharides, sugar, bulking sweeteners, low-intensity sweeteners, or other related food ingredients are conventionally used.

In some embodiments, a method for producing a foodstuff, cosmetic, or nutraceutical ingredient is described. The ingredient may comprise one or more oligosaccharides and one or more polysaccharides. The method may comprise the steps of:

a) forming the one or more oligosaccharides and the one or more polysaccharides by an enzymatic reaction, said enzymatic reaction comprising the step of contacting, in a solution or suspension, one or more polysaccharide-cleaving enzymes and one or more feedstocks, wherein the one or more feedstocks comprise sugar cane, sugar cane bagasse, corn stover, corn cob, wheat bran, wheat straw, hardwood, softwood, cellulose, chitin, chitosan, xylan, xyloglucan, mixed-linkage glucan, mannan or lignocellulose;

b) separating the one or more oligosaccharides and the one or more polysaccharides from the enzymatic reaction mixture; and then c) recombining the one or more oligosaccharides and the one or more polysaccharides to form the ingredient.

The one or more oligosaccharides may comprise cello-oligosaccharides, xylo-oligosaccharides, mixed-linkage glucan oligosaccharides, manno-oligosaccharides, xyloglucan oligosaccharides or chito-oligosaccharides, or derivatives of any of the aforementioned oligosaccharides.

The polysaccharide-cleaving enzymes may be one of cellulase, xylanase, xyloglucanase, endo-glucanase, cellobiohydrolase, mannanase, lichenase or a lytic polysaccharide monooxygenase (LPMO), preferably selected from the group consisting of AA9, AA10, AA11, AA13, AA14 and AA15. The polysaccharide-cleaving enzyme may be prepared from $T.$ reesei fungi and/or the enzymatic reaction runs until there is 5-75% undigested polysaccharide-containing feedstocks remaining, preferably 5-65%, more preferably 5-50%.

The one or more polysaccharides may comprise cellulose, xylan, mannan, mixed-linkage glucan, chitin, chitosan or lignocellulose. The polysaccharide-containing feedstock may be pre-treated by acid, alkali, heat, pressure, and/or enzyme treatment. The polysaccharide-cleaving enzyme(s) may be operably linked to a catalytic or non-catalytic module, preferably wherein the polysaccharide-cleaving enzyme may be operably linked to a non-catalytic module and the non-catalytic module is a carbohydrate-binding module.

In this embodiment, after the separating of the one or more oligosaccharides and one or more polysaccharides, the one or more oligosaccharides and one or more polysaccharides may be: purified; and/or undergo chemical, physical, or enzymatic treatment, such as reduction, oxidation, caramelisation, or Maillard reaction; and/or may be recombined by combining a spray-dried powder of oligosaccharides with a dried polysaccharide powder.

In some embodiments, the ingredient comprises three or more oligosaccharides of different molecular weights, wherein the method may comprise forming the three or more oligosaccharides by an enzymatic reaction, said enzymatic reaction comprising the step of contacting, in a solution or suspension, one or more polysaccharide-cleaving enzymes and one or more feedstocks.

The polysaccharide-containing feedstock may comprise plant biomass, preferably sugar cane, corn stover, corn cob, wheat bran, wheat straw, hardwood, softwood, cellulose, chitin, chitosan, xylan, xyloglucan, mixed-linkage glucan, mannan or lignocellulose.

At least one of the polysaccharide-cleaving enzymes may comprise one of cellulase, xylanase, xyloglucanase, endo-glucanase, cellobiohydrolase, mannanase, lichenase or a lytic polysaccharide monooxygenase (LPMO) and the polysaccharide-cleaving enzyme may be prepared from $T.$ reesei fungi.

The composition may comprise monosaccharides at <5% w/w of total oligosaccharide component (comprising glucose, xylose and/or mannose), disaccharides at >20% w/w of total oligosaccharide component (comprising cello-, xylo- and/or manno-oligosaccharides), trisaccharides at >5% w/w of total oligosaccharide component (comprising cello-, xylo- and/or manno-oligosaccharides) and tetrasaccharides at >2% w/w of total oligosaccharide component (comprising cello-, xylo- and/or manno-oligosaccharides).

The polysaccharide-containing feedstock may be pre-treated by acid, alkali, heat, pressure, and/or enzyme treatment. The polysaccharide-cleaving enzyme(s) may be operably linked to a catalytic or non-catalytic module, preferably wherein the polysaccharide-cleaving enzyme is operably linked to a non-catalytic module and the non-catalytic module is a carbohydrate-binding module.

The oligosaccharides may be purified; and/or undergo chemical, physical, or enzymatic treatment, such as reduction, oxidation, caramelisation, or Maillard reaction; and/or are recombined by combining a spray-dried powder of oligosaccharides with a dried polysaccharide powder.

EXAMPLES

Example 1—Improved Dissolution of a Cello-Oligosaccharide and Xylo-Oligosaccharide Combination Composition Combining cellobiose with xylo-oligosaccharide improves the dissolution of xylo-oligosaccharides in jam.
1. 280 g strawberries were brought to boil in a saucepan.
2. After heating, the straw berries were blended.
3. 5 g of xylo-oligosaccharides in powder form, or 10 g of a 50:50 mix of xylo-oligosaccharides and cellobiose in powder form, was added to the blend.
4. After being left for 1 minute the powder was mixed in to the jam.
5. The xylo-oligosaccharide sample formed a clump that was difficult to mix into the blended strawberries, whereas the xylo-oligosaccharides and cellobiose mixture readily dispersed into the jam and did not form any clumps.

Example 2—Improved Dissolution of Oligosaccharide Combinations in Water

Dissolution of xylo-oligosaccharides into water are improved when mixed with other oligosaccharides such as cello-oligosaccharide, manno-oligosaccharide, and mixed-linkage glucan oligosaccharides (MLGOs).
1. 50 mg xylo-oligosaccharide powder was (a) left alone, or (b) mixed with 10 mg cellobiose, (c) mixed with 10 mg MLGOs or (d) mixed with 10 mg manno-oligosaccharides.
2. 0.5 mL water was added, and the tubes were incubated at room temperature for 5 minutes until water had fully soaked into the powder.
3. Each tube was then vortexed at high speed for 30 seconds.
4. An undissolved pellet remained in the xylo-oligosaccharide-only tube (a), which was absent from all of the others, whereas none of the other tubes (b-d) had pellets remaining.

Example 3—Baked Goods with Improved Characteristics

Combinations of cellobiose ($cell_2$), xylo-oligosaccharides (XOS), and cellulose produce cookies with improved characteristics 1. 40 g all-purpose flour, ⅛ teaspoon baking soda, and 1/16 teaspoon salt were mixed together.
2. 1 oz unsalted butter, half large egg yolk, and ¼ teaspoon vanilla extract were whisked with 20 g oligosaccharide mix (comprising xylo-oligosaccharides and/or $cell_2$) and optionally 6 g cellulose polysaccharide and was added to the mixture. There were 4 oligosaccharide mixes tested: 100% xylo-oligosaccharides, 67% xylo-oligosaccharides: 33% $cell_2$, 33% xylo-oligosaccharides: 67% $cell_2$, and 100% $cell_2$.
3. 30 g chocolate chips were mixed into the mixture.
4. 40 g balls were baked for 15 minutes at 350° F.

Figure 2:
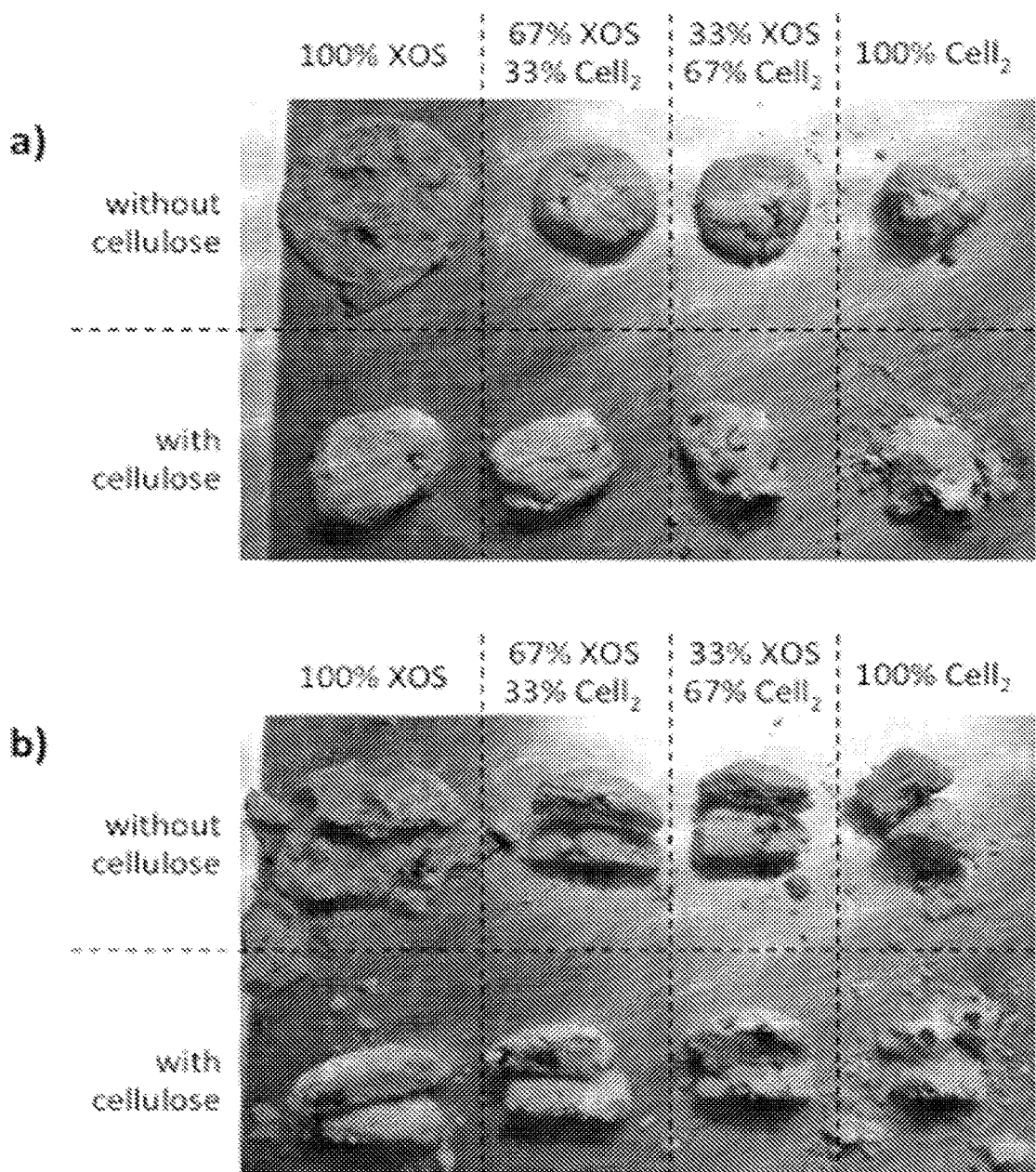
FIG. 2 shows cookies fresh out of the oven (panel a) and cut in half after a cooling period (panel b). The cookies were made using various compositions comprising combinations of cellobiose, xylo-oligosaccharides, and cellulose.

Without cellulose, the xylo-oligosaccharide-only cookies melted too quickly and formed crisp cookies that were too thin, and the $cell_2$-only cookies were dry and crumbly, as shown in FIG. 1. Cookies with combinations of $cell_2$ and xylo-oligosaccharides held their structure better and looked more like cookies. Of the cookies that contained cellulose polysaccharide, all developed cookie properties except for the $cell_2$-cellulose cookie, which was too crumbly. FIG. 2 shows the cookies fresh out of the oven (FIG. 2, panel a) and cut in half after a cooling period (FIG. 2, panel b). When cut, the cookies with combinations of oligosaccharide types, or oligosaccharide-polysaccharide combinations maintained their structure best. Cookies with combinations of cellobiose and xylo-oligosaccharides had better structure and mouth-feel than those made using only a single type of oligosaccharide. In conclusion, oligosaccharide combinations and oligosaccharide-polysaccharide combinations perform better as sugar substitutes in cookies than individual oligosaccharides.

Example 4—Improved Sweetness

Demonstrating improved sweetness of combinations of cello-oligosaccharide and xylo-oligosaccharide combinations
1. Five oligosaccharide solutions were created:
   a. 40 mg/mL xylo-oligosaccharide
   b. 80 mg/mL xylo-oligosaccharide
   c. 120 mg/mL cellobiose
   d. 120 mg/mL cellobiose, 40 mg/mL xylo-oligosaccharide
   e. 120 mg/mL cellobiose, 80 mg/mL xylo-oligosaccharide
2. Eleven participants were asked to taste 2 mL samples of the solutions sequentially from (a)-(e). Before each tasting, participants washed their mouths with water and after each tasting they were asked to assign a numerical value to the sweetness of the solution. The first solution in which they could taste sweetness was arbitrarily assigned a 1, and later solutions were assigned a number based on the factor by which they were sweeter than the former. Values were standardised to 1 for comparison.

Figure 3:
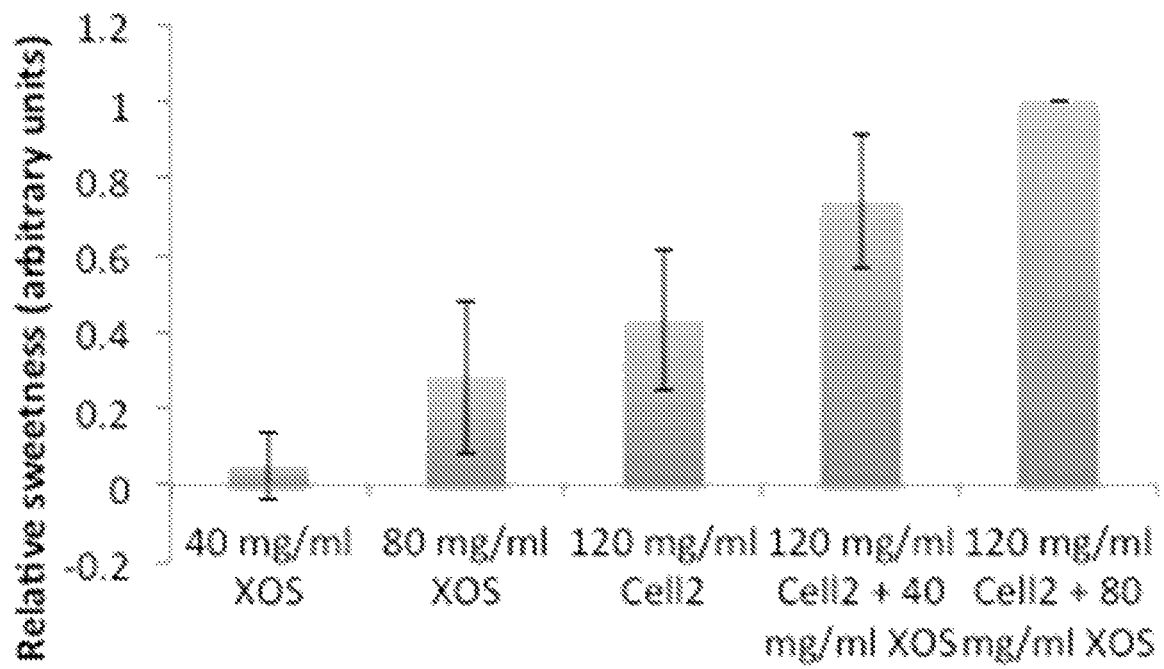
FIG. 3 shows the relative sweetness of various combinations of xylo-oligosaccharide-cellobiose in solution.

As shown in FIG. 3, the results show a synergistic impact of sweetness in the solutions with combinations of cellobiose and xylo-oligosaccharides compared to the solutions with only cellobiose or xylo-oligosaccharides.

Figure 4:
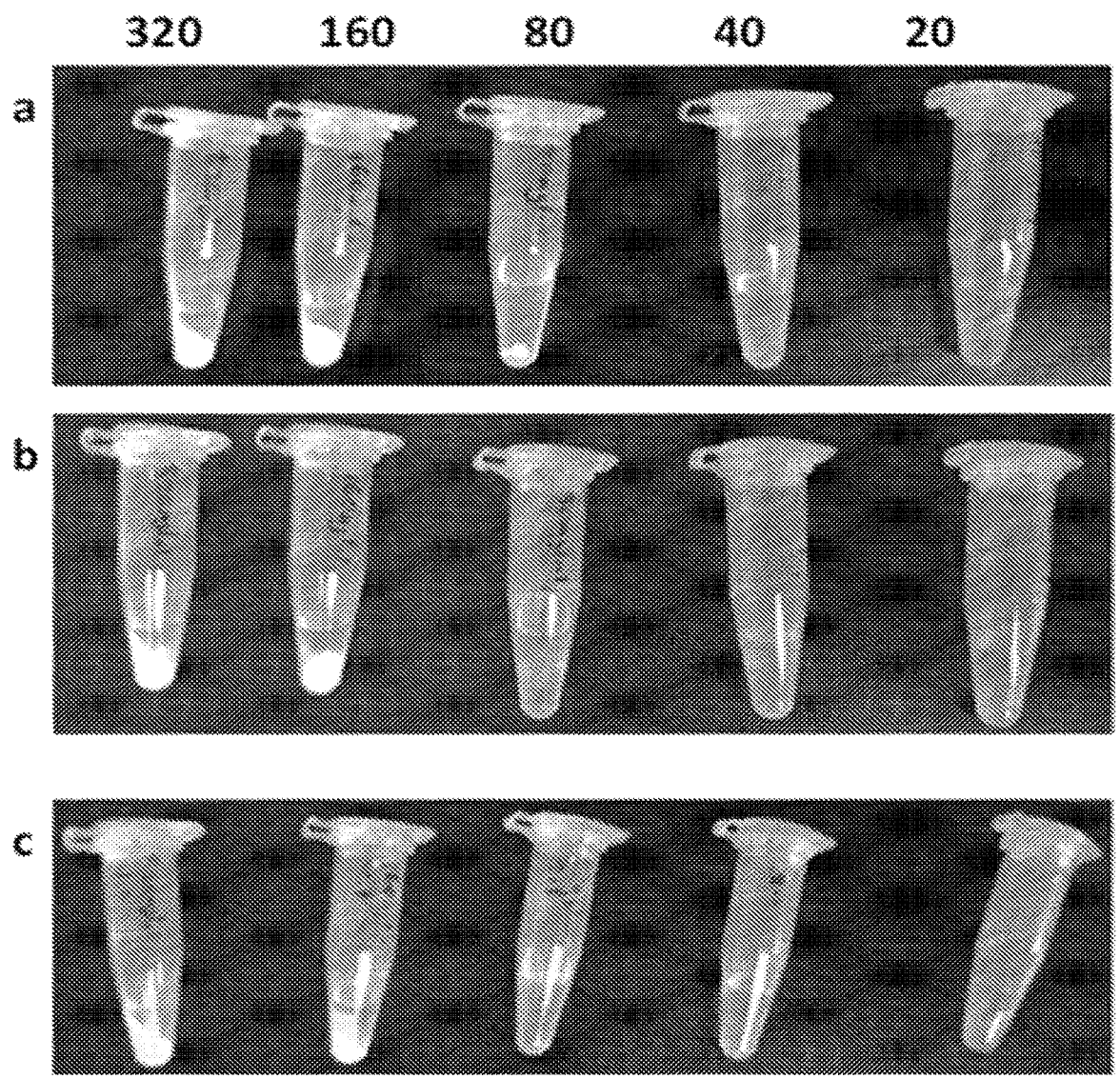
FIG. 4 shows solutions/suspensions of cellobiose at concentrations from 20-320 mg/mL after being vortexed for 30 seconds alone (panel a), or in the presence of half the concentration of xylo-oligosaccharides (panel b) or the same concentration of xylo-oligosaccharides (panel c).

Example 5—Improved Solubility of Cellobiose when Combined with Xylo-Oligosaccharides 1. Solutions/suspensions of cellobiose at concentrations from 20-320 mg/mL were vortexed for 30 seconds alone (FIG. 4, panel a), in the presence of half the concentration of xylo-oligosaccharides (FIG. 4, panel b), or the same concentration of xylo-oligosaccharides (FIG. 4, panel c).

2. Dissolution was enabled more readily at higher concentrations through the presence of xylo-oligosaccharides (e.g., at 80 mg/mL).

Figure 5:
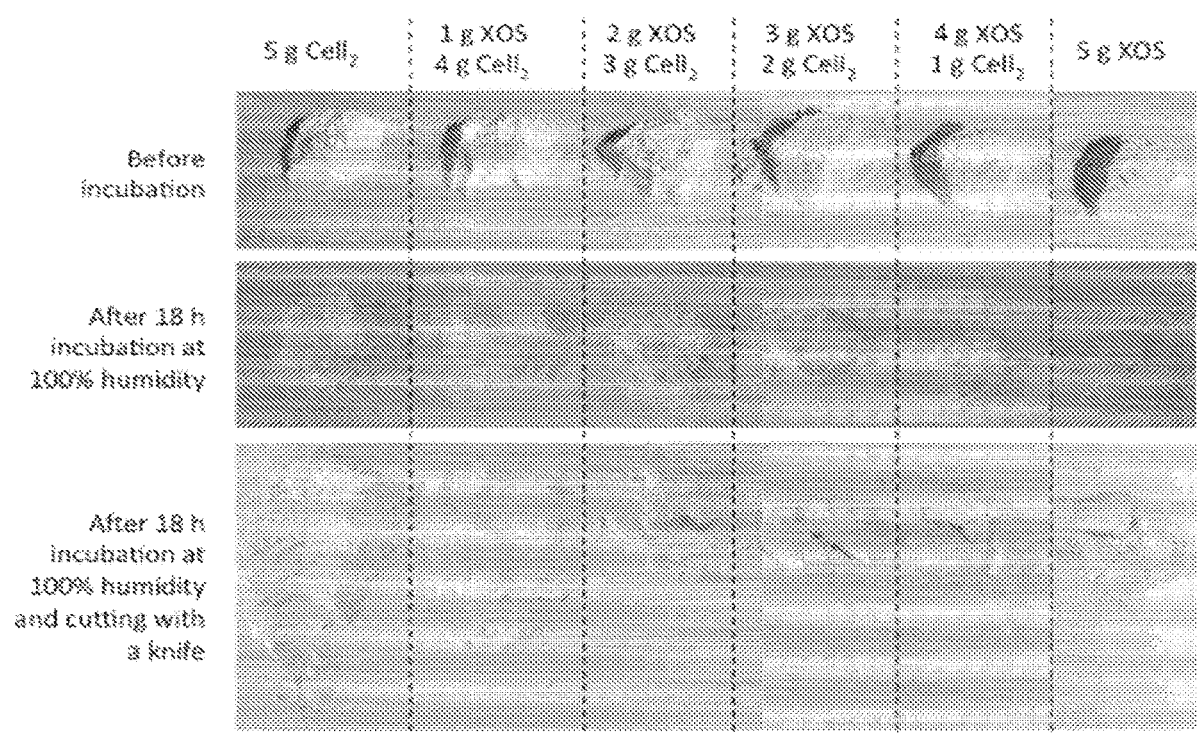
FIG. 5 shows the hygroscopicity of various cellobiose-xylo-oligosaccharide compositions.

Example 6—Modifying Hygroscopicity of Oligosaccharide Powder by Changing Compositions The compositions are to be used in a wide range of foodstuff, cosmetic, or nutraceutical applications, therefore the required hygroscopicity for each application can vary. The aim of this example was to test if hygroscopicity can be adapted by altering the oligosaccharide compositions.
1. 5 g of oligosaccharide compositions (cellobiose, 4:1 cellobiose:xylo-oligosaccharide, 3:2 cellobiose:xylo-oligosaccharide, 2:3 cellobiose:xylo-oligosaccharide, 1:4 cellobiose:xylo-oligosaccharide, xylo-oligosaccharide) were incubated for 10 hours at 25° C. in 100% humidity.
2. After incubation, oligosaccharide samples were cut using a kitchen knife to demonstrate water capture. The cellobiose and the 4:1 cellobiose:xylo-oligosaccharide samples effectively resisted water uptake, whereas the other samples increasingly absorbed water, as shown in FIG. 5. This shows that the hygroscopicity of the composition can be modified to the desired level in order to meet the requirements of its application.

Example 7—Baked Goods Made Using Undigested Polymeric Cellulose

Figure 6:
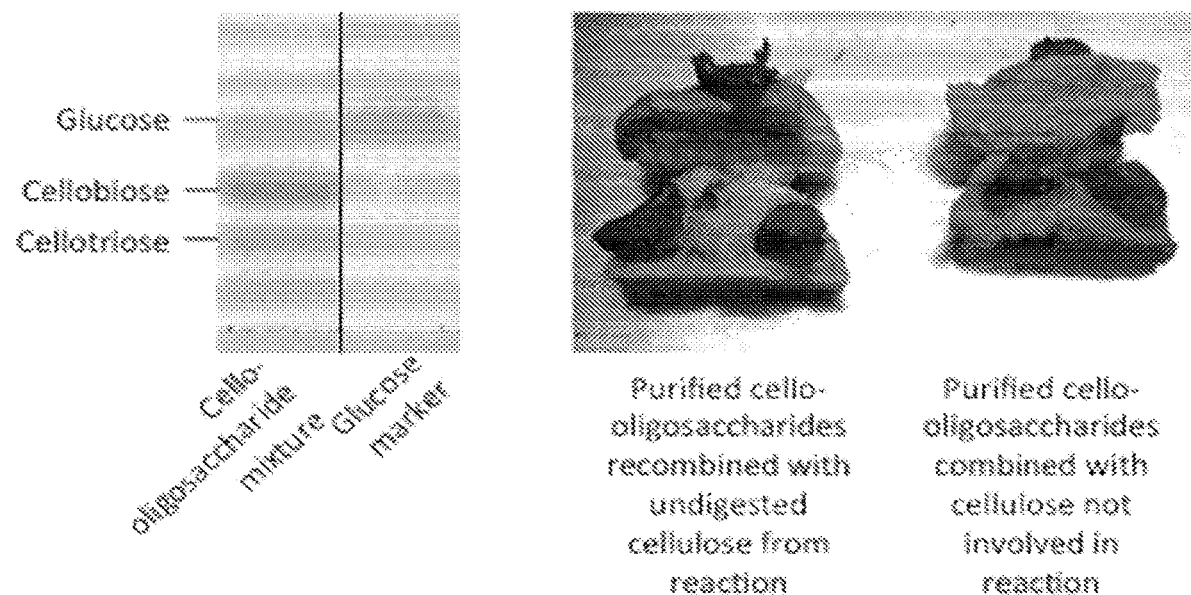
FIG. 6 shows the oligosaccharide profile analysed by thin-layer chromatography of the cello-oligosaccharide mixture produced by the enzymatic reaction on microcrystalline cellulose, and cakes made using the oligosaccharides with either the dried undigested microcrystalline cellulose from cellulolytic reactions or untreated microcrystalline cellulose.

Undigested polymeric cellulose from hydrolase reaction can perform functionally in cakes as well as untreated polymeric cellulose
1. 10 g microcrystalline cellulose was incubated for 36 hours at 37° ° C. in 400 mL solution containing 2 mg GH7 cellobiohydrolase I (*Trichoderma longibrachiatum*), 5 mg GH12 cellulase (*Aspergillus niger*), and 0.3 mg GH6 cellobiohydrolase II (microbial) (all purchased from Megazyme, Ireland) with constant agitation at 800 rpm.
2. After the reaction, the oligosaccharide profile was analysed by thin-layer chromatography showing 41% breakdown of polymeric cellulose into cello-oligosaccharides comprising mainly cellobiose with some cellotriose, cellotetraose, and glucose (shown in FIG. 6).
3. The cello-oligosaccharide mixture was separated from the undigested cellulose through filtration and both were dried.
4. The undigested cellulose from the reaction was heated at 100° ° C. for 1 hour in IM NaOH before being washed with water until neutral and dried.
5. 2 g dried cello-oligosaccharide mixture was mixed with either 2 g dried undigested cellulose from the reaction or 2 g microcrystalline cellulose.
6. The two samples were whipped with 4 g unsalted butter, before mixing in 4 g egg, and then 4 g flour.
7. 4 g semi-sweet chocolate chips were added to the batter.
8. Mini cupcakes were baked at 37° C. for 10 minutes.
9. Cakes were cooled and cut in half. Results showed that the dried undigested cellulose from cellulolytic reactions performed identically to microcrystalline cellulose in cake structure.

Example 8—Baked Goods Made Using Undigested Polymeric Lignocellulose

Figure 7:
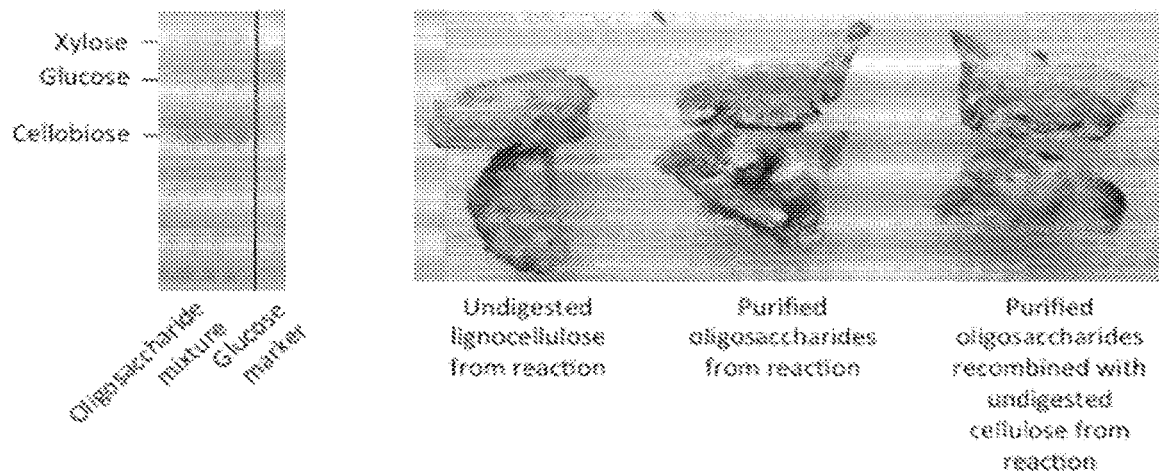
FIG. 7 shows the oligosaccharide profile analysed by thin-layer chromatography of the oligosaccharide mixture produced by the enzymatic reaction on wheat bran lignocellulose, and cakes made using the undigested lignocellulose from cellulolytic reaction alone, the oligosaccharides from cellulolytic reaction alone, and the undigested lignocellulose from cellulolytic reaction in combination with oligosaccharides from cellulolytic reaction.

Undigested polymeric lignocellulose from partial cleavage of corn cob can be added to cake mix without decrease in cake properties.
1. 10 g dried corn cob was grated into very fine pieces, ground in a slurry using a pestle and mortar, and incubated at 100° ° C. for 30 minutes.
2. The slurry was then incubated for 36 hours at 37° C. in 400 ml solution containing 1.6 ml *T. reesei* cellulase extract.
3. After the reaction, the oligosaccharide profile was analysed by thin-layer chromatography showing 68% breakdown of polymeric lignocellulose into oligosaccharide comprising mainly cellobiose with some xylose and glucose.
4. The oligosaccharide mixture was separated from the undigested lignocellulose through filtration and dried.
5. Three samples (4 g dried oligosaccharide mixture: 2 g dried oligosaccharide mixture plus 2 g dried undigested lignocellulose; and 4 g dried undigested lignocellulose) were whipped with 4 g unsalted butter, before mixing in 4 g egg, and then 4 g flour.
6. Mini cupcakes were baked at 37° C. for 10 minutes.
7. Cakes were cooled and cut in half. As shown in FIG. 7, the results showed that undigested lignocellulose from cellulolytic reactions alone gave poor structural support to the cake. However, in combination with oligosaccharides, undigested lignocellulose gave comparable support to cake structure.

Example 9—Baked Goods with Undigested Polymeric Lignocellulose from Partial Cleavage of Mahogany Wood, Wheat Bran, and Poplar Wood Undigested polymeric lignocellulose from partial cleavage of mahogany wood, wheat bran, and poplar wood functions better in cakes than fresh mahogany wood, wheat bran, and poplar wood
1. 10 g dried mahogany wood, wheat bran, and poplar wood were ground in a slurry using a pestle and mortar and incubated at 100° C. for 30 minutes.
2. The mahogany slurry was incubated for 36 hours at 37° C. in 400 ml solution containing 1.6 ml *T. reesei* cellulase extract and 2 mg GH26 Mannanase (Cellvibrio japonicas; purchased from Megazyme, Ireland). The wheat bran slurry was incubated for 36 hours at 37° ° C. in 400 mL solution containing 1.6 ml *T. reesei* cellulase extract. The poplar slurry was incubated for 36 hours at 37° C. in 400 mL solution containing 2 mg GH7 cellobiohydrolase I (*Trichoderma longibrachiatum*), 5 mg GH12 cellulase (*Aspergillus niger*), 0.3 mg GH6 cellobiohydrolase II (microbial) (all purchased from Megazyme, Ireland), 10 mg *Aspergillus oryzae* xylanase (purchased from Sigma).
3. After the reaction, the oligosaccharide profile was analysed by thin-layer chromatography showing 68% breakdown of polymeric lignocellulose into oligosaccharide comprising mainly cellobiose with some xylose and glucose.
4. The oligosaccharide mixture was separated from the undigested lignocellulose through filtration and dried.
5. For each of the three lignocellulose types, 2 g dried oligosaccharide mixture was mixed with 1 g dried undigested polysaccharide from the reaction or 1 g fresh lignocellulose. For each of the three lignocellulose types, the two 3 g saccharide compositions made were whipped with 3 g unsalted butter, before mixing in 3 g egg, and then 3 g flour.

Figure 8:
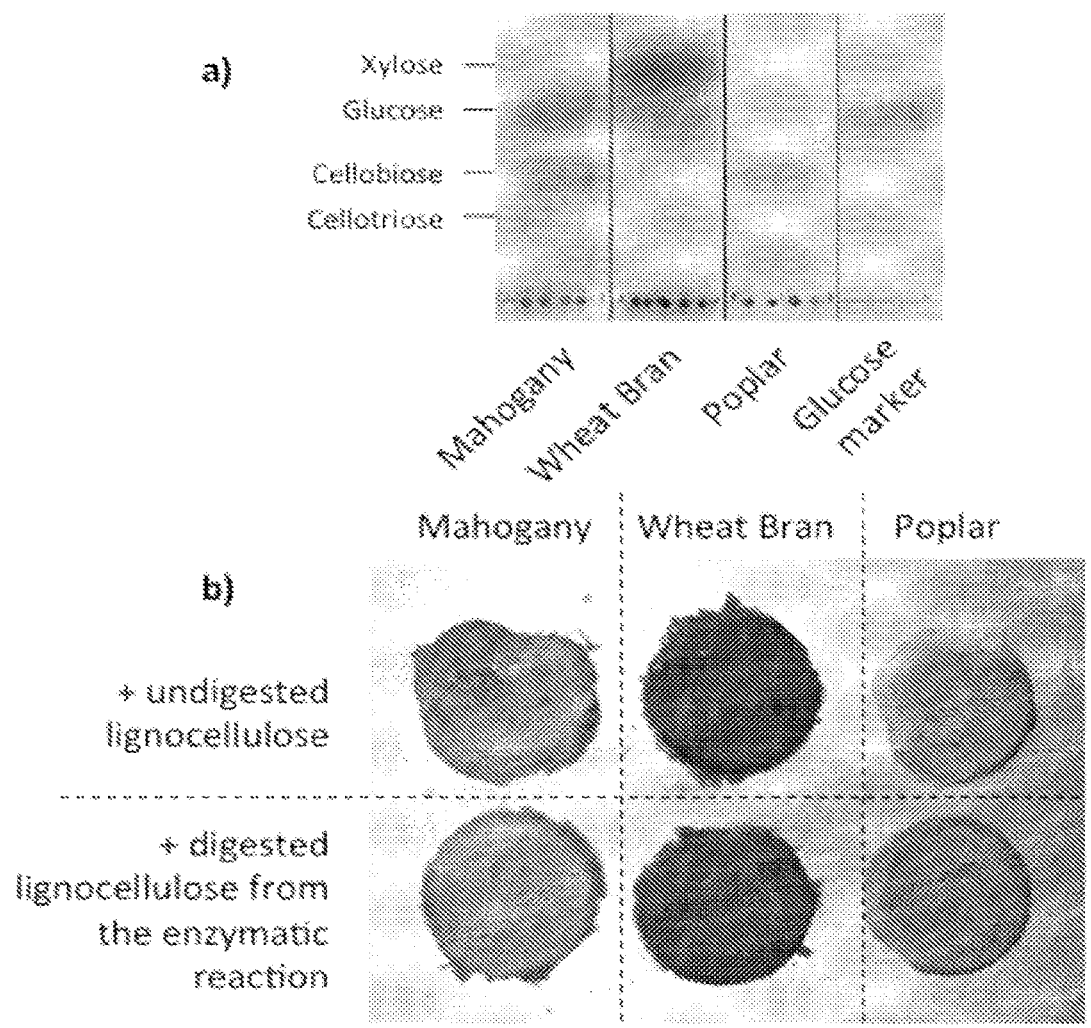
FIG. 8 shows the oligosaccharide profile analysed by thin-layer chromatography of the oligosaccharide mixture produced by the enzymatic reaction, and cakes made using the oligosaccharides from cellulolytic reaction along with the undigested lignocellulose from cellulolytic reactions or with fresh lignocellulose.

6. Mini cupcakes were baked at 37° C. for 10 minutes.
7. Cakes were cooled and analysed. As shown in FIG. 8, the results showed that the fresh lignocellulose incorporated less-well into the structure of the cake than the recombined undigested lignocellulose from the enzymatic reactions did. In the former, distinct pieces of lignocellulose were conspicuous in the mahogany and wheat bran cakes, and less so in the poplar cake. In contrast, lignocellulose pieces were hardly noticeable in the cakes containing recombined undigested lignocellulose from the enzymatic reactions.

Example 10—Gastrointestinal Tolerance

Addition of polymeric cellulose to cellobiose-xylo-oligosaccharide compositions improves gastrointestinal tolerance.

The compositions are to be used in a wide range of foodstuffs, ideally up to levels comparable to sugar consumption in the average Western diet (~80 g/day). It is known that, at these levels, oligosaccharides, such as xylo-oligosaccharides, can cause gastrointestinal distress, including diarrhoea, discomfort, and bloating. For xylo-oligosaccharides the highest tolerated dose is 12 g/day. The aim of this example was to test if adding different polysaccharides to the oligosaccharide preparation before consumption would increase the gastrointestinal tolerance of the oligosaccharides, for example, by slowing gastric emptying, and enable far higher volumes to be comfortably consumed.

1. The experiments were performed on 2 healthy male volunteers aged 22 and 31.
2. For 17 days, each volunteer consumed an average of 30 g test oligosaccharides comprising cellobiose and xylo-oligosaccharides at ratios from 0:1 to 4:1. The maximum consumed on a single day was 50 g and the minimum was 20 g.
3. One volunteer reported diarrhea on day 2 and heavy diarrhoea on day 17. The second volunteer reported minor discomfort and bloating on some days.
4. For the next 12 days, each volunteer consumed an average of 70 g of test saccharides comprising cellobiose and xylo-oligosaccharides at ratios from 0:1 to 4:1, supplemented with microcrystalline cellulose or carboxymethylcellulose at κ-33% of the total test saccharide. The maximum consumed on a single day was 110 g and the minimum was 40 g.
5. No gastrointestinal symptoms were observed.

This confirmed that concomitant consumption of polysaccharides with the oligosaccharides improves tolerance and enables comfortable consumption of much larger amounts of oligosaccharide and at levels comparable to sugar consumption in the average Western diet (~80 g/day).

Example 11—Moisture Content

Four different compositions were made by mixing individual saccharide powders and undigested biomass. Sample 1 comprises 15% undigested biomass mixed with 45% xylo-oligosaccharide and 40% cellobiose w/w. Sample 2 comprises 50% xylo-oligosaccharide mixed with 50% cellobiose w/w. Sample 3 comprises 10% xylo-oligosaccharide mixed with 90% cellobiose w/w. Sample 4 comprises 90% xylo-oligosaccharide mixed with 10% cellobiose w/w.

The TES-AC-097 (UKAS) method was used to measure the moisture content. In this method the sample was heated to 70° C. in a vacuum chamber overnight and the loss in weight was measured. The moisture content results are given in Table 1 below. Sample 1 had the highest moisture content whereas sample 3 had the lowest. Samples 2 and 4 had intermediate moisture content between these two extremes and had similar moisture content to each other. The effect of moisture on flowability of particles can vary depending on the nature of the material. When particles absorb water, they can become cohesive and flow properties can be adversely affected. The higher moisture content found in Sample 1 may provide improved characteristics such as binding, moistness, etc. in baked goods.

TABLE 1

Moisture content of powders (TES-AC-097 (UKAS))

| Sample number | Moisture content (g/100 g) |
| --- | --- |
| Sample 1 | 4.01 |
| Sample 2 | 1.2 |
| Sample 3 | 0.7 |
| Sample 4 | 1.4 |

Example 12—Digi Eye Imaging

Figure 9:
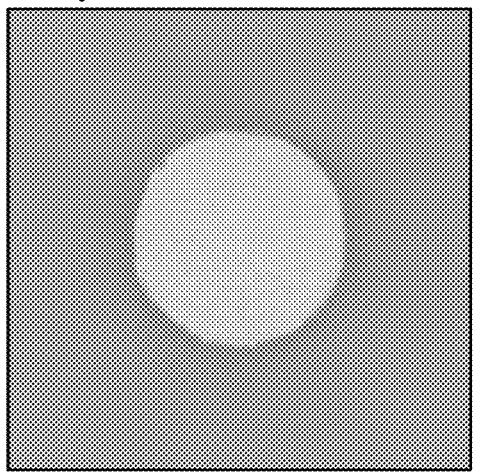
FIG. 9 shows colour images captured for samples 1, 2, 3, and 4 using a Digi Eye system.
Figure 9:
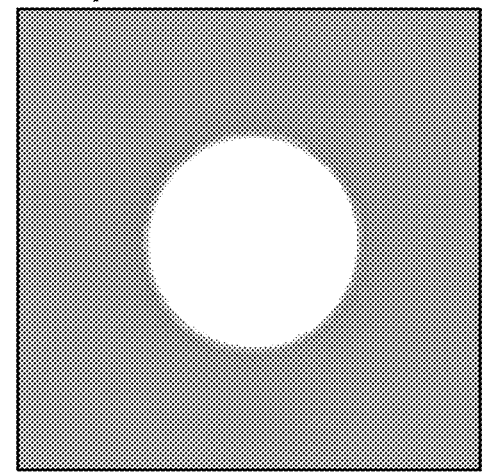
Figure 9:
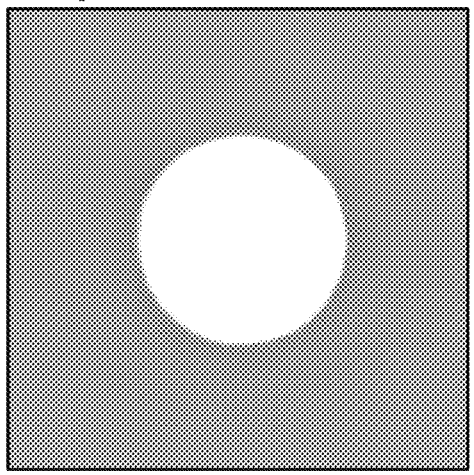
Figure 9:
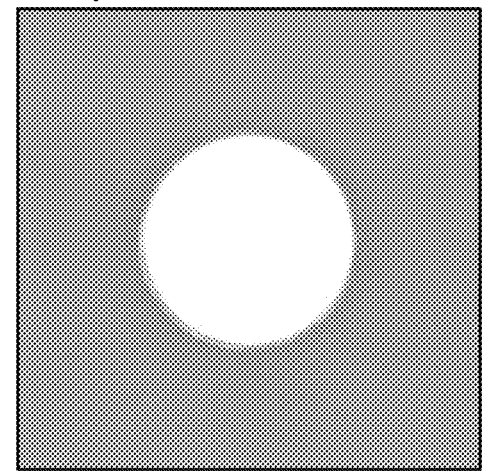

Samples from Example 11 were used and colour images were captured using a DigiEye system (Verivide). This instrument comprises an imaging cabinet with controlled D65 lighting conditions and a camera. Diffuse lighting, a fixed magnification, and consistent presentation conditions were used for all images. FIG. 9 shows colour calibrated DigiEye images for all samples. The results for the imaging show that Sample 1 has a different colour due to the presence of biomass as compared to oligosaccharide mixtures in samples 2, 3 and 4.

Example 13—Colour Analysis

Colour measurements for samples from Example 11 were taken in triplicate using a CM-5 instrument (Konica Minolta) according to method TES-CM-126. The samples were transferred into a glass petri dish and the average colour measurements were performed on a 30 mm diameter surface area in reflectance mode using a D65 illumination and 10° observation.

Figure 10A:
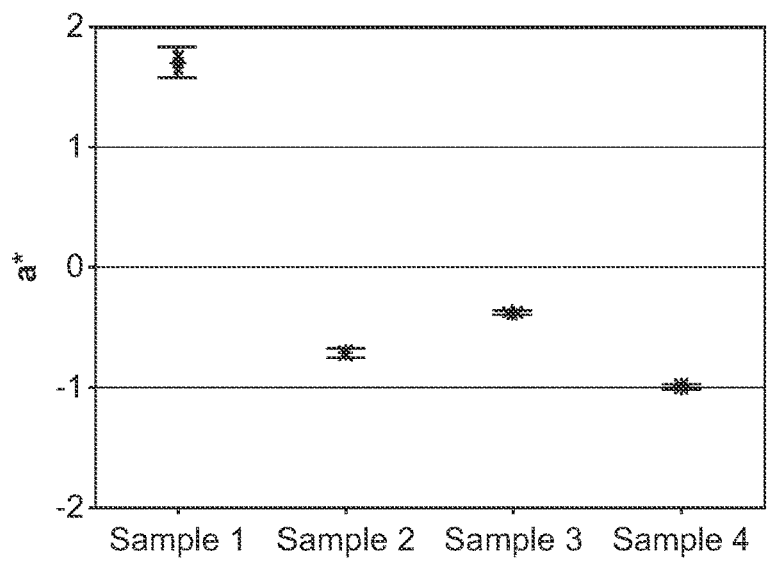
FIGS. 10A-10C show colour measurements of oligosaccharide samples.
Figure 10B:
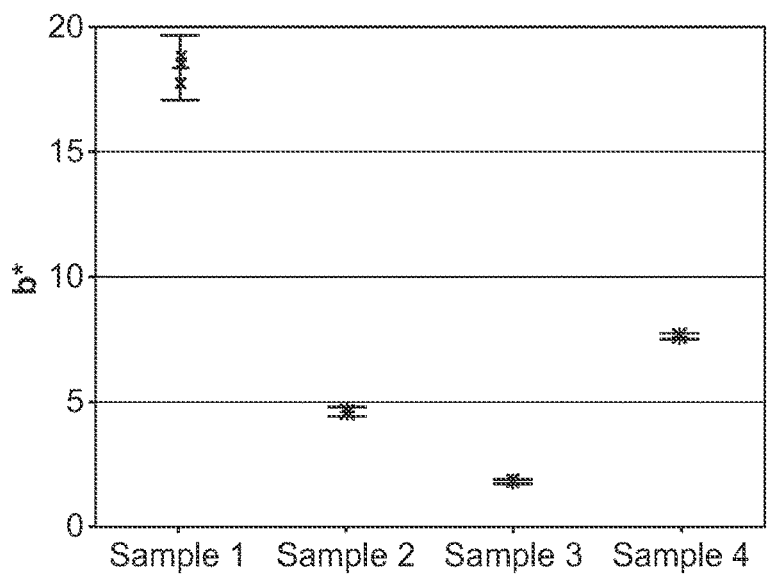
Figure 10C:
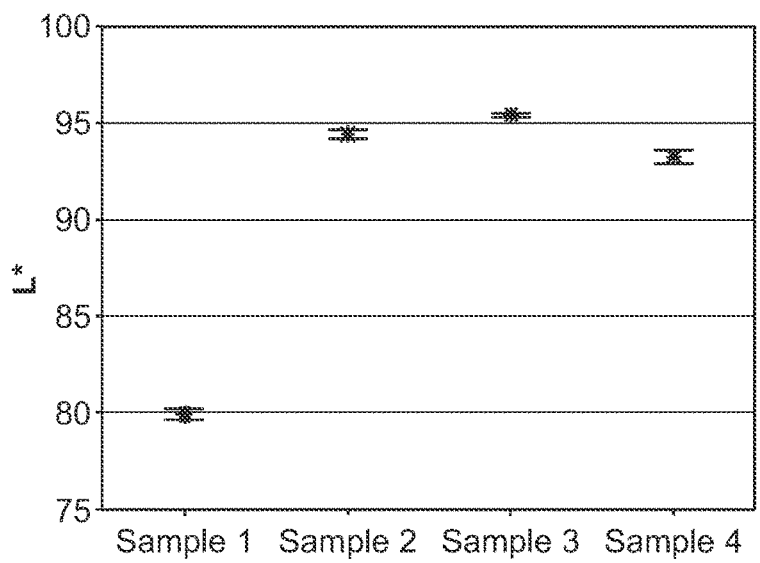

Colour measurements were recorded using CIELAB colour space, three coordinates ($L^*$, $a^*$, $b^*$) are associated with each colour:

$L^*$: Lightness (where $L^*=0$ is black and $L^*=100$ is white) is as shown in FIG. 10C.

$a^*$: Position along an axis from green to red (where positive $a^*$ values indicate redness and negative $a^*$ values indicate greenness) is as shown in FIG. 10A.

$b^*$: Position along an axis from blue to yellow (where positive $b^*$ values indicate yellowness and negative $b^*$ values indicate blueness) is as shown in FIG. 10B.

The four samples all had significantly different $L^*$, $a^*$, $b^*$ values from each other, Sample 1 being the most different as shown by the colour differences ΔE in Table 2. Sample 3 had the whitest colour, white being defined by the $L^*$, $a^*$, $b^*$ values 100, 0, 0, respectively. Sample 1 had the darkest colour and had the strongest red and yellow colour. Sample 1 also showed the widest confidence intervals due to the non-uniformity of the powder with some dark and light particles. The colour differences ΔE between all the samples are greater than 1, representing a visually perceptible colour difference. In summary, the colour of Sample 1 was the most different from the other samples and Sample 3 was the closest to a white colour.

TABLE 2

Table of the colour differences ΔE between samples

|  | Sample 1 | Sample 2 | Sample 3 | Sample 4 | White |
|---|---|---|---|---|---|
| Sample 1 | — | 20.13 | 22.77 | 17.34 | 27.28 |
| Sample 2 | 20.13 | — | 2.99 | 3.25 | 7.30 |
| Sample 3 | 22.77 | 2.99 | — | 6.23 | 5.00 |
| Sample 4 | 17.34 | 3.25 | 6.23 | — | 10.24 |
| White | 27.28 | 7.30 | 5.00 | 10.24 | — |

Example 14—Hygroscopicity Measurements

Figure 11:
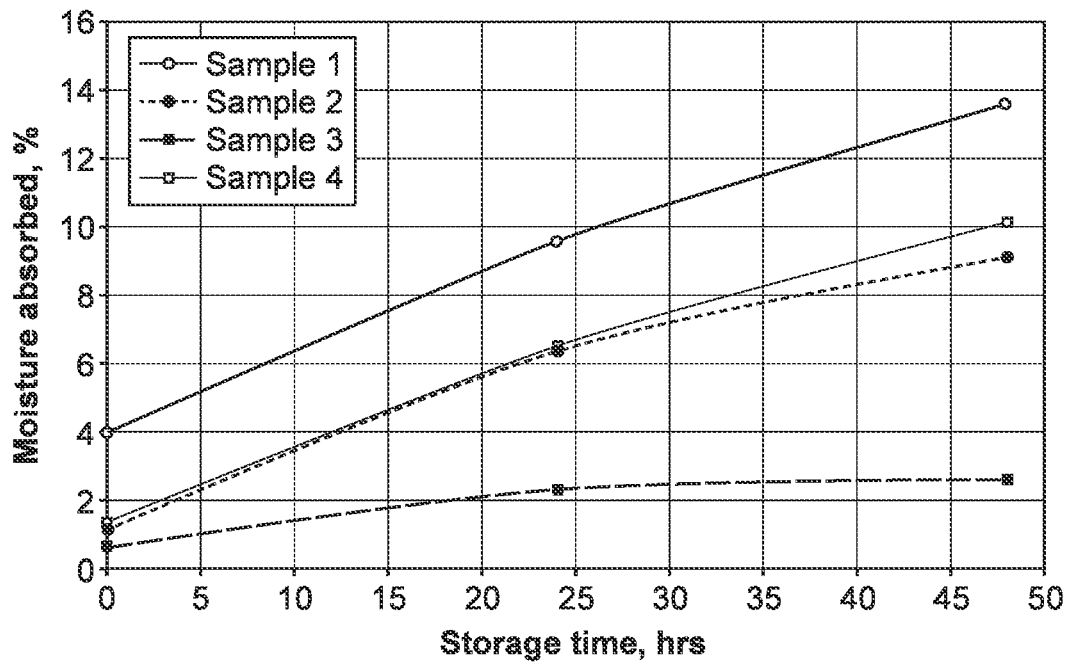
FIG. 11 shows hygroscopicity profiles of samples 1, 2, 3, and 4.

Approximately 5 g of each sample from Example 11 was weighed into aluminium foil dishes and covered with foil. Several holes were made in the foil cover to allow moisture to enter the dish but prevent contamination from airborne debris or powder being lost. The samples were stored in a temperature and humidity-controlled room (20° C. and 70% relative humidity) and the change in weight of the samples measured after 24 and 48 hours. Each sample was measured in duplicate. The results of the hygroscopicity measurements as shown in FIG. 11 show that all samples had the tendency to pick up moisture from the atmosphere at 20° C. and 70% relative humidity. Sample 3 had the lowest moisture content to begin with and picked up less moisture than the other samples. The trend on graph for sample 3 suggests that moisture pickup had reached an equilibrium or was very close to an equilibrium with the surrounding atmosphere. This sample had not clumped together after 48 hours. Sample 1 had the highest moisture content and absorbed moisture at a faster rate than sample 3 which is unexpected. The rate of moisture pick-up of sample 1 was similar to samples 2 and 4. After 48 hours, sample 1 had formed some clumps. Samples 2 and 4 had intermediate moisture content between samples 1 and 3 and absorbed moisture from the atmosphere at a similar rate to each other up to 24 hours. Sample 4 absorbed more moisture between 24 and 48 hours compared with sample 2. Sample 3 did not show any clump formation but sample 4 had lost its particulate nature and formed a viscous liquid. It could therefore be described as deliquescent.

The hygroscopicity measurements were repeated on samples that had been dried overnight at 70° C. under vacuum. This was to ensure that any historical moisture absorbed by the samples was removed and were dry when the hygroscopicity test was started. It was noteworthy to report that after drying sample 1 was in the form of hard lumps of various sizes and difficult to break. The lumps were broken up and the powder sieved through a 500 μm sieve to obtain free flowing particles of the sample. Samples 2-4 were free-flowing powders after drying. The percentage moisture gained is given in FIG. 6 and as before sample 3 absorbed the least amount of moisture from the atmosphere over the 96-hour period. Sample 4 absorbed the highest amount of moisture in the same period and had changed to a viscous liquid as was found in the first study. The rate of moisture pickup by sample 4 was greater than the other three samples. Sample 1 absorbed more moisture than sample 2, but the rate of moisture pickup appeared to be similar for these two samples Example 15—Cohesion Strength of Powders The cohesion strength describes a powder's internal flow resistance, which depends on the adhesive forces between the particles. The measurements for samples made in Example 11 were conducted with an Anton Paar MCR Rheometer MCR102 equipped with a Powder Cell, a powder fluidizer with mass-flow controller (Fluidization Set Scientific), and a two-blade stirrer. The cohesion strength is determined with the two-blade stirrer from the torque recorded during the measurement and a geometry-specific factor. The method consists of two steps. During the first interval, residual influences from previous powder handling are erased. This is known as the Pressure-Drop Method. This was achieved by fully fluidizing the sample for 60 seconds. During the second interval, a constant rotational speed of 8 rpm was set while the volumetric flow was zero. The cohesion strength S in Pa was calculated by using linear regression over the last 20 data points.

Figure 12:
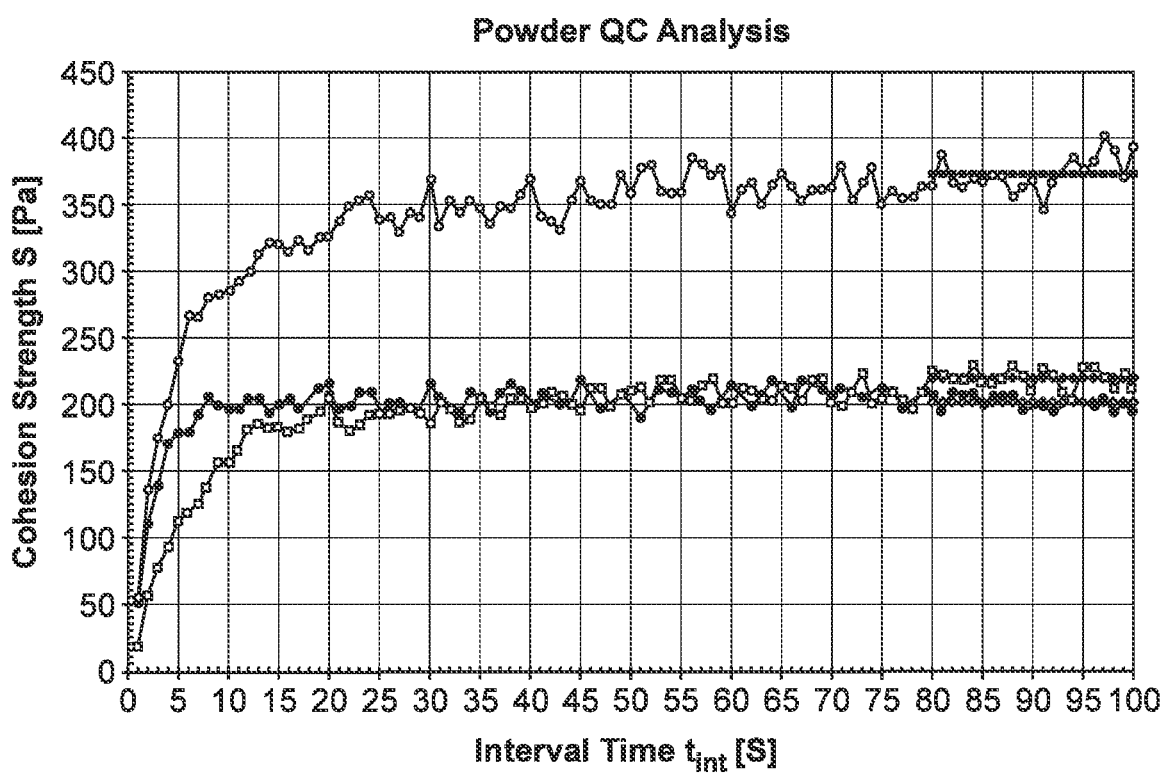
FIG. 12 shows cohesion strength of samples 1, 2, 3, and 4.

The examples of the traces of the cohesion strength obtained of samples 2 to 4 are shown in FIG. 12. The analysis of the traces is given in Table 3. The cohesion strength of samples 2 and 3 was significantly lower than that of sample 4. The higher value of sample 4 indicate higher cohesive forces between the particles. This might be due to different particle sizes and particle-size distributions and thus, different cohesion strengths. Sample 4 also had higher bulk density, suggesting greater inter-particle interaction and this may also be a factor contributing to the higher cohesion strength. Sample 1 was not measured as it could not be fluidised. This suggests that the cohesion strength of this powder was high, and this may be due to the high moisture content of this sample as well as other factors.

TABLE 3

Cohesion strength of powder samples.

| Sample number | Cohesion Strength (Pa) |
|---|---|
| Sample 1 | Did not fluidise |
| Sample 2 | 207.1 ± 4.6 |
| Sample 3 | 217.5 ± 2.6 |
| Sample 4 | 380.5 ± 7.6 |

Example 16—Viscosity

Figure 13:
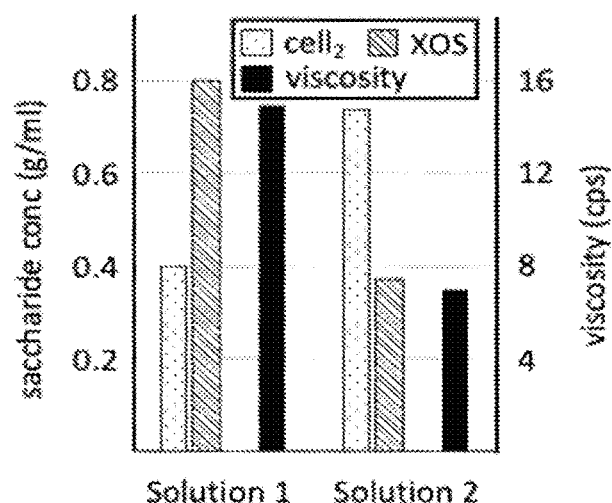
FIG. 13 shows viscosity of cellobiose and xylo-oligosaccharide mixtures.

For viscosity measurements, 2 solutions were made comprising a 1:2 and a 2:1 ratio of cellobiose and xylo-oligosaccharides. The samples were tested using a Brookfield HDB VE roto-viscometer using standard testing procedures, a 400 mL sample is taken in a tall-form beaker to ensure that no container effects occur. The instrument is operated as per the manufacturer's instructions with respect to ranges. Roto-viscometry using spindle code 61, spindle speed 100 rpm, and at 22° C. (see FIG. 13).

Figure 14:
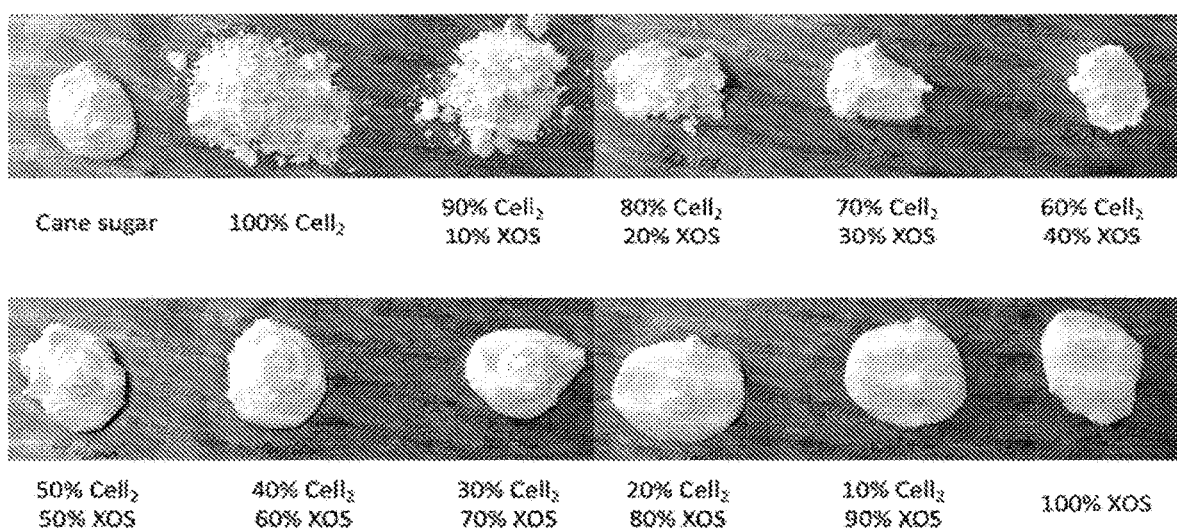
FIG. 14 shows examples of cream cheese icing made using oligosaccharide mixtures.

Example 17—Cream Cheese Icing Made Using Oligosaccharide Mixtures 7 g butter and 21 g cream cheese were combined. 50 g icing sugar or premade $Cell_2$/XOS mixture were mixed in. Results are shown in FIG. 14.

When $Cell_2$ is used alone the structure of the icing is very dry and crumbly and as a result it is unable to hold a proper structure of icing and function as icing properly. As $Cell_2$ is replaced by XOS in 10% increments the structure becomes increasingly better able to stick together. Between about 50:50 and about 20:80 $Cell_2$:XOS w/w ratios the texture of the icing compositions is similar to that when using sugar and has a sturdy thick cream cheese icing consistency. Between about 50:50 and about 20:80 $Cell_2$:XOS w/w ratios the surface appearance of the icing compositions is similar to that when using sugar and has a smooth, shiny surface that retains structure like it does when sugar is used. As the mixture approaches and reaches 100% XOS the texture becomes increasingly thick and lumpy and/or crystallised as the XOS fails to incorporate properly into the icing, and the surface is unable to hold the whipped appearance of icing. Acceptable $Cell_2$:XOS w/w ratio ranges for cream cheese icing include 50:50 to 20:80 with optimal being 30:70.

Example 18—Meringue Made Using Oligosaccharide Mixtures

The product was made as follows:
1. Whisk 30 g egg whites until foamy.
2. Add 30 g sugar or premade $Cell_2$/XOS mixture half at a time.
3. Whisk to stiff peaks.

Figure 15:
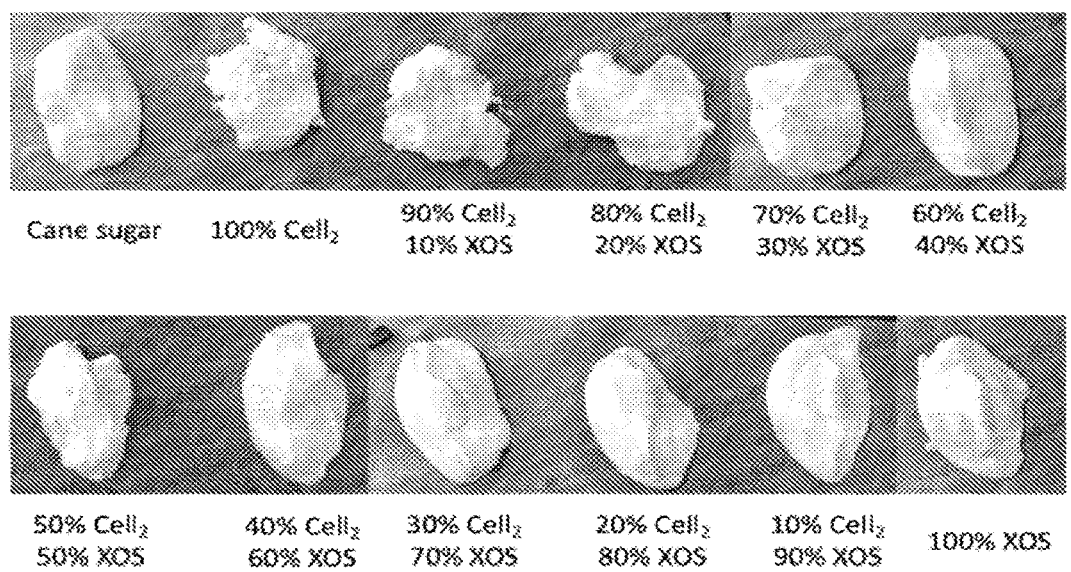
FIG. 15 shows examples of meringue made using oligosaccharide mixtures.

Results are shown in FIG. 15. When $Cell_2$ is used alone the structure of the meringue is dry, dull and brittle and as a result it is unable to hold a proper structure of meringue and function as meringue properly. As $Cell_2$ is replaced by XOS in 10% increments the structure becomes increasingly better able to stick together. Between about 70:30 and about 10:90 $Cell_2$:XOS w/w ratios the texture of the meringue composition is similar to that when using sugar and has a sturdy thick meringue consistency. Between about 70:30 and about 10:90 $Cell_2$:XOS w/w ratios the surface appearance of the meringue compositions is similar to that when using sugar and has a smooth, shiny surface that retains structure like it does when sugar is used. As the mixture approaches and reaches 100% XOS the texture becomes increasingly thin and the surface becomes shinier. Acceptable $Cell_2$:XOS w/w ratio ranges for meringue include 70:30 to 10:90 with optimal being 30:70

Example 19: Chocolate Chip Muffin/Cupcakes Made Using Oligosaccharide Mixtures

The products were made as follows:
1. Combine 64 g flour, ¾ tsp baking powder, ⅛ tsp salt, and 25 g sugar or premade $Cell_2$/XOS mixture.
2. Separately combine 45 g milk, 17 g sunflower oil, and 13 g egg.
3. Mix the wet ingredients into the dry.
4. Fold in 30 g chocolate chips.
5. Weigh out 55 g batter per muffin.
6. Bake 12 minutes in a preheated oven at 170° C.

Figure 16:
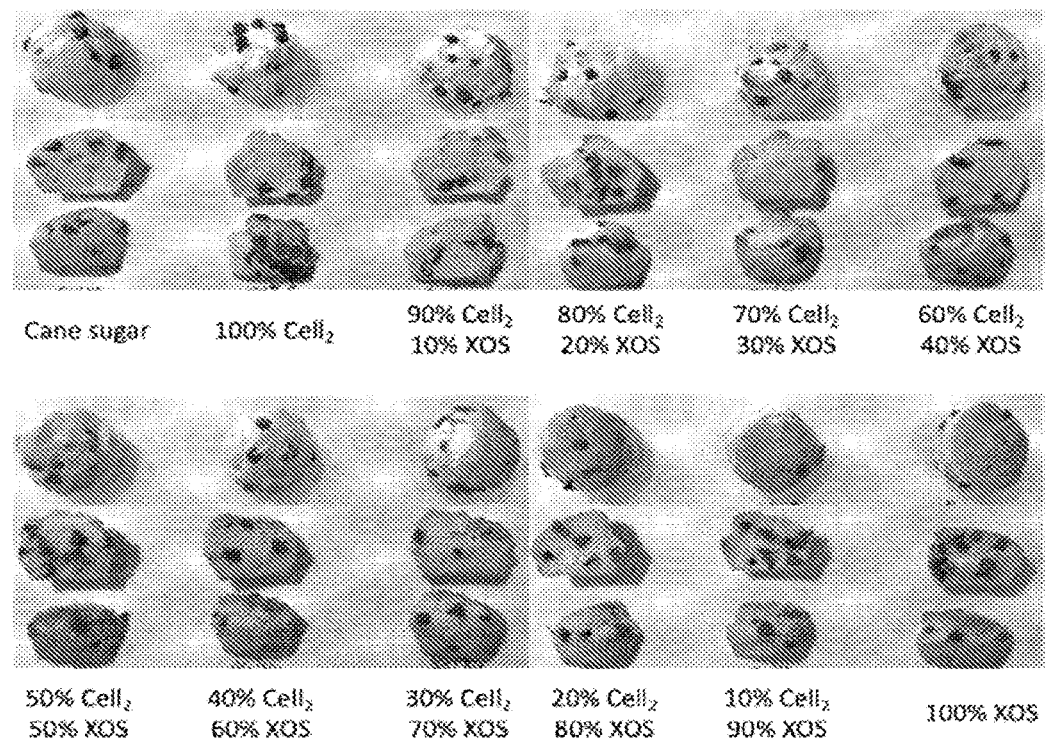
FIG. 16 shows examples of chocolate chip muffin or cupcakes made using oligosaccharide mixtures.

Results are shown in FIG. 16. When $Cell_2$ is used alone the structure of the muffin is dry, dense, lumpy and readily crumbles and as a result it is unable to hold a proper structure of muffin and function as muffin properly. The surface browns unevenly and wrinkles far more and is far lumpier than with sugar. As $Cell_2$ is replaced by XOS in 10% increments the structure becomes increasingly better able to stick together. Between about 90:10 and about 10:90 $Cell_2$:XOS w/w ratios the texture of the muffin compositions is similar to that when using sugar and has a soft, cakey, chewy consistency, is able to hold moisture better and has a more sugar-like rise and colour. Between about 90:10 and about 10:90 $Cell_2$:XOS w/w ratios the surface appearance of the muffin compositions is similar to that when using sugar: it browns more evenly and has a more cake-like wrinkling structure.

As the mixture approaches and reaches 100% XOS the texture becomes increasingly thick and dense, and the surface becomes excessively brown and does not display the typical wrinkled/cracked structure of a muffin surface, instead forming a solid film-like surface. Acceptable $Cell_2$:XOS w/w ratio ranges for muffins/cupcakes include 90:10 to 10:90 with optimal being between 60:40 and 40:60.

Example 20: Peanut Butter Cookies Made Using Oligosaccharide Mixtures

The products were made as follows:
1. Cream 14 g butter and 23 g sugar or premade $Cell_2$/XOS mixture.
2. Add 7 g egg and 0.7 g vanilla extract and combine thoroughly.
3. Add 15 g peanut butter and mix until combined.
4. Mix in 20 g flour, 0.35 g baking powder, and 0.35 g baking soda.
5. Weigh out 20 g of dough, roll into a ball.
6. Bake 9 minutes in a preheated oven at 160° C.

Figure 17:
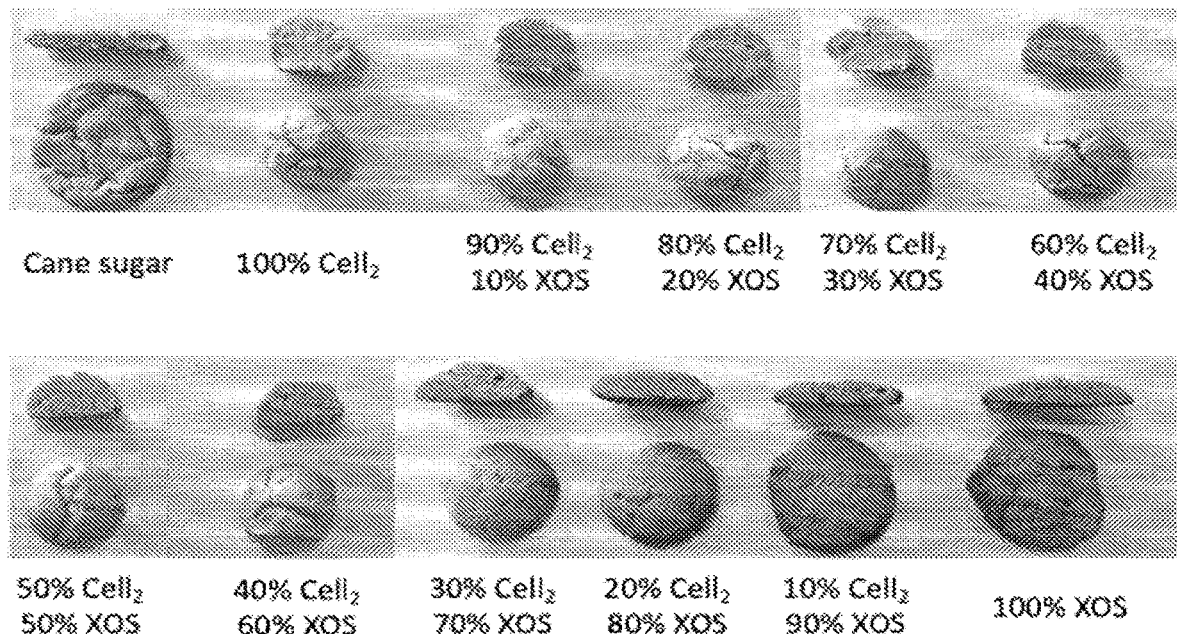
FIG. 17 shows examples of peanut butter cookie made using oligosaccharide mixtures.

Results are shown in FIG. 17. When $Cell_2$ is used alone the structure of the cookie is very dry and dense as $Cell_2$ does not incorporate well into the dough. As a result the composition is unable to hold a proper structure of a cookie. When $Cell_2$ is used alone the surface is also too light-colored and does not brown enough. As $Cell_2$ is replaced by XOS in 10% increments the structure becomes increasingly better able to stick together. Between about 30:70 and about 10:90 $Cell_2$:XOS w/w ratios the texture of the cookie compositions is similar to that when using sugar and has a chewy, crumbly consistency. Between about 30:70 and about 10:90 $Cell_2$:XOS w/w ratios the surface appearance of the cookie compositions is similar to that when using sugar and has a cracked, wrinkled, evenly-browned surface that retains structure like it does when sugar is used. As the mixture approaches and reaches 100% XOS the surface becomes too dark and pitted, the shape is unevenly distributed and partly burns at the edges, and the texture becomes increasingly thick, lumpy and granular as the XOS fails to incorporate properly into the cookie and sometimes forms clumps that will not readily break apart. Acceptable $Cell_2$:XOS w/w ratio ranges for cookies include about 30:70 to about 10:90 with optimal being between about 20:80 and about 10:90.

Example 21: Jams Made Using Oligosaccharide Mixtures

Products were made as follows:
1. Combine 60 g raspberries and 30 g sugar or premade $Cell_2$/XOS mixtures in a small sauce pan.
2. Cook over medium low heat until it reaches thread stage.

Figure 18:
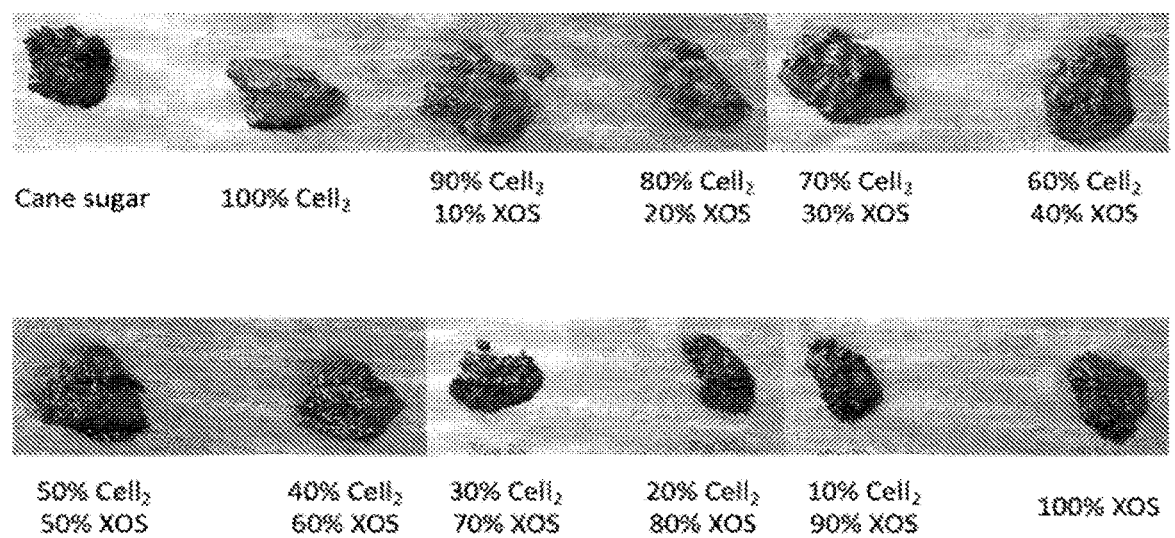
FIG. 18 shows examples of jam made using oligosaccharide mixtures.

Results are shown in FIG. 18. When $Cell_2$ is used alone the structure of the jam is dry, sandy, dull, dense and solid and so unable to hold a proper structure of jam and function as jam properly.

As $Cell_2$ is replaced by XOS in 10% increments the structure becomes increasingly better able to stick together and hold moisture. Between about 50:50 and about 10:90 $Cell_2$:XOS w/w ratios the texture of the jam compositions is similar to that when using sugar and has a moist, smooth, and soft consistency that easily flows and can be spread. Between about 50:50 and about 10:90 $Cell_2$:XOS w/w ratios the surface appearance of the jam compositions is similar to that when using sugar and has a smooth, shiny surface like it does when sugar is used. As the mixture approaches and reaches 100% XOS the texture becomes increasingly thin and translucent and the XOS can fail to incorporate properly into the jam and sometimes forms clumps that will not readily break apart. Acceptable $Cell_2$:XOS w/w ratio ranges for jam icing include about 50:50 to about 10:90 with optimal being about 30:70 to about 10:90.

Example 22: Ice Cream Made Using Oligosaccharide Mixtures

A recipe that can be used to make such products is as follows:
1. Place ice cream maker insert into the freezer at least one day ahead of making ice cream.
2. Heat 284 g double cream, 300 g full fat milk, and 57.5 g sugar or premade $Cell_2$/XOS mixture in a medium sauce pan until just steamy.
3. Whisk together 60 g egg yolks and 57.5 g sugar or premade $Cell_2$/XOS mixture until lightened in colour.
4. Pour about ⅓ of the steamy cream mixture into the egg mixture. Combine and pour back into the sauce pan.
5. Cook, stirring constantly until the mixture thickens enough to coat the back of a spoon.
6. Chill custard overnight.
7. Pour custard into ice cream machine and churn for 10-30 minutes.
8. Scoop into a container and freeze at least 3 hours before serving.

100% $Cell_2$ is expected to be too dull, thick and grainy and 100% XOS is expected to be shiny, lumpy with crystallised XOS and too liquid. A combination of the two would be expected to hold well, be smooth, and have the proper amount of shine.

Example 23: Chocolate Made Using Oligosaccharide Mixtures

A recipe that can be used to make such products is as follows:
1. Combine 700 g cocoa mass, 50 g cocoa butter and 250 g sugar or premade $Cell_2$/XOS mixture with mild heat until sugar or premade $Cell_2$/XOS mixture melts and everything is well combined.
2. Temper the chocolate and use as needed.

100% $Cell_2$ is expected to be dry, crumbly, and dull. 100% XOS is expected to be runny, shiny, and crystallised/lumpy. A combination of the two is expected to result in shiny chocolate with the proper density and texture.

Example 24: Pate De Fruits Made Using Oligosaccharide Mixtures

A recipe that can be used to make such products is as follows:
1. Bring 500 g fruit puree to boil.
2. Combine 100 g sugar or premade $Cell_2$/XOS mixture with 12.5 g pectin powder.
3. Add the dry mix to the puree and bring to boil whisking continually.
4. Add 200 g sugar or premade $Cell_2$/XOS mixture and bring to softball stage (112° C.-116) ° ° C.
5. Remove from heat and add 5 g lemon juice.
6. Pour into paper lined mould.
7. Allow to set before removing from the pan.
8. Cut into pieces.

100% $Cell_2$ is expected to be dull, dry, opaque, and crumbly. 100% XOS is not expected to set properly and will be shiny and translucent (neither will reach temperatures). A combination of the two is expected to result in a pate de fruits that is soft, chewy/sticky, and slight translucent.

Example 25: Soft Caramels Made Using Oligosaccharide Mixtures

A recipe that can be used to make such products is as follows:
1. In a sauce pan cook 250 g sugar or premade $Cell_2$/XOS mixture, 250 g double cream, and 125 g glucose to 112° C.
2. Remove from heat and add 65 g soft butter.
3. Cook further to firm ball stage (118-120°) C.
4. Pour into a paper lined fudge tray and allow to cool.
5. Once cold cut into bite sized pieces.

100% $Cell_2$ is expected to be dry, dull, and crumbly. 100% XOS is not expected to set properly and will be shiny and crystallised/lumpy (neither will reach temperatures). A combination of the two should result in a soft chewy caramel that is slightly shiny.

Example 26: Marshmallows Made Using Oligosaccharide Mixtures

A recipe that can be used to make such products is as follows:
1. Bloom 25 g gelatine in 180 g of water in a bowl of a mixer.
2. Once the gelatine is bloomed, heat the over a bain-marie to dissolve the gelatin.
3. Heat 180 g of water, 300 g sugar or premade $Cell_2$/XOS mixture, and 150 g glucose to 116° C., remove and stir in the remaining 60 g of glucose.
4. Pour the syrup into the gelatine mixture and whisk till cooled and thickened. Transfer to a piping bag.
5. Sieve 500 g icing sugar and 500 g corn flour together and divide onto trays.
6. Pipe marshmallow mix onto icing sugar mixture.
7. Allow to set.
8. Cut into bite sized pieces and dust-off excess sugar.

100% $Cell_2$ is expected to be dry, dull, and crumbly. 100% XOS is expected to be shiny but will not set (neither will reach temperatures). A combination of the two may result in a properly set marshmallow that has the correct aeration and chewy texture.

TABLE 4

Sequence listings

| Name | SEQ ID | Sequence |
|---|---|---|
| LPMO: AA9 LPMO from *Podospora anserine* | 1 | MKGLLSVAAL SLAVSEVSAH YIFQQLSTGS TKHGVFQYIR QNTNYNSPVT DLSSNDLRCN EGGASGANTQ TVTVRAGDSF THILDTPVYH QGPVSVYLSK APGSASSYDG SGTWFKIKDW GPTFPGGQWT LAGSYTAQLP SCITDGEYLL RIQSLGIHNP YPAGTPQFYI SCAQIKVTGG GSVNPSGVAI PGAFKATDPG YTANIYSNFN SYTVPGPSVF SCGSNGGGSS PVEPQPQPTT TLVTSTRAPV ATQPAGCAVA KWGQCGGNGW TGCTTCAAGS TCNTQNAYYH QCV |

TABLE 4-continued

Sequence listings

| Name | SEQ ID | Sequence |
|---|---|---|
| Lichenase GH16 Lichenase from *Bacillus subtilis* subsp. *subtilis* str. 168 | 2 | MPYLKRVLLL LVTGLFMSLF AVTATASAQT GGSbbDPFNG YNSGFWQKAD GYSNGNMFNC TWRANNVSMT SLGEMRLALT SPAYNKFDCG ENRSVQTYGY GLYEVRMKPA KNTGIVSSFF TYTGPTDGTP WDEIDIEFLG KDTTKVQFNY YTNGAGNHEK IVDLGFDAAN AYHTYAFDWQ PNSIKWYVDG QLKHTATNQI PTTPGKIMMN LWNGTGVDEW LGSYNGVNPL YAHYDWVRYT KK |
| Xylanase: GH5 Arabinoxylanase from *Ruminiclostridium thermocellum* | 3 | MGASIKTS1K IRTVAFVSII AIALSILSFI PNRAYASPQR GRPRLNAART TFVGDNGQPL RGPYTSTEWT AAAPYDQIAR VKELGFNAVH LYAECFDPRY PAPGSKAPGY AVNEIDKIVE RTRELGLYLV ITIGNGANNG NHNAQWARDF WKFYAPRYAK ETHVLYEIHN EPVAWGPPYS SSTANPPGAV DMEIDVYRII RTYAPETPVL LFSYAVFGGK GGAAEALKDI RAFNKAVFGN ENAVWTNEAV APHGYAGWQE TTIAVEELLK AGYPCFMTEY AGGAWGSGMG GLDVELTYEL ERLGVSWLTF QYIPPTGVSD DVTKPEYFSA LVENSGLSWT PDYGNWPAAR GVYGNGGLAR ETATWINNFL TGTTRIEAED FDWGGNGVSY YDTDSVNVGG QYRPDEGVDI EKTSDTGGGY NVGWISEGEW LEYTIRVRNP GYYNLSLRVA GISGSRVQVS FGNQDKTGVW ELPATGGFQT WTTATRQVFL GAGLQKLRIN ALSGGFNLNW IELSPISTGT IPDGTYKFLN RANGKTLQEV TGNNSIITAD YKGITEQHWK IQHIGGGQYR ISSAGRGWNW NWWMGFGTVG WWGTGSSTCF IISPTGDGYY RIVLVGDGTN LQISSGDPSK IEGKAFHGGA NQQWAILPVS APAFPTGLSA VLDSSGNTAN LTWNAAPGAN SYNVKRSTKS GGPYTTIATN ITSTNYTDTG VATGTKYYYV VSAVSNGVET LNSAEAILQY PKLTGTVIGT QGSWNNIGNT IHKAFDGDLN TFFDGPTANG CWLGLDFGEG VRNVITQIKF CPRSGYEQRM IGGIFQGANK EDFSDAVTLF TTTSLPGSGT LTSVDVDNPT GFRYVRYLSP DGSNGNIAEL QFFGTPAGEE NDDVHLGDIN DDGNINSTDL QMLKRHLLRS IRLTEKQLLN ADTNRDGRVD STDLALLKRY ILRVITTL |
| Xylanase: GH5 Xylanase from *Gonapodya prolifera* | 4 | MARLSSLIAL VLAFVAVSAP ALAARGRPRL NGKTFVADSG VPLRGPFTST EWTPAVPAAN IANMRNYNFN AIHLYAETFD PNYPAAGSQK PGYAATRVDQ IVAATKAANM YVVIVLANGA NNGKFNLNYA KDFWSFYAAR YKNETHVIYE IHNEPVQWGP PYISSTQSPG AVSMNADCYK IIRAVAPDTP VLLFTYASIG GGSSAAGAVK DAQSFNTAVF GNANAQWTNE AIAIHGYWGA QGASDAAKAL NAAGFSVVLT EFAAATSPTS PNGGQDTVLT GFMEQQGVSW LTFLHVPPTG VSGDVTDPNQ YTNRMTAAGI GFDRDPGLNA VGGGQAAPVP VPAPAPVPSP VPAPVPAVPA VRTTTARPAP SPSPVPAPVP APAPVPAPVP APVPAPVPAP VPAPVPASPA ATTTRRHRTR PPRTTTAPAV PAPPPAATPK VCG |
| Xylanase: GH30 xylanase from *Dickeya chrysanthemi* | 5 | MNGNVSLWVR HCLHAALFVS ATAGSFSVYA DTVKIDANVN YQIIQGFGGM SGVGWINDLT TEQINTAYGS GVGQIGLSIM RVRIDPDSSK WNIQLPSARQ AVSLGAKIMA TPWSPPAYMK SNNSLINGGR LLPANYSAYT SHLLDFSKYM QTNGAPLYAI SIQNEPDWKP DYESCEWSGD EFKSYLKSQG SKFGSLKVIV AESLGFNPAL TDPVLKDSDA SKYVSIIGGH LYGTTPKPYP LAQNAGKQLW MTEHYVDSKQ SANNWTSAIE VGTELNASMV SNYSAYVWWY IRRSYGLLTE DGKVSKRGYV MSQYARFVRP GALRIQATEN PQSNVHLTAY KNTDGKMVIV AVNTNDSDQM LSLNISNANV TKFEKYSTSA SLNVEYGGSS QVDSSGKATV WLNPLSVTTF VSK |
| Xylanase: GH30 xylanase from *Bacillus subtilis* subsp. *subtilis* str. 168 | 6 | MIPRIKKTIC VLLVCFTMLS VMLGPGATEV LAASDVTVNV SAEKQVIRGF GGMNHPAWAG DLTAAQRETA FGNGQNLQGF SILRIHVDEN RNNWYKEVET AKSAVKHGAI VFASPWNPPS DMVETFNRNG DTSAKRLKYN KYAAYAQHLN DFVTFMKNNG VNLYAISVQN EPDYAHEWTW WTPQEILRFM RENAGSINAR VIAPESFQYL KNLSDPILND PQALANMDIL GTHLYGTQVS QFPYPLFKQK GAGKDLWMTE VYYPNSDTNS ADRRWPEALDV SQHIHNAMVE GDFQAYVWWY IRRSYGPMKE DGTISKRGYN MAUFSKFVRP GYVRIDATKN PNANVYVSAY KGDNKVVIVA INKSNTGVNQ NFVLQNGSAS NVSRWITSSS SNLQPGTNLT VSGNHFWAHL PAQSVTTFVV NR |
| Xylanase: GH30 Xylanase from *Bacteroides oyatus* | 7 | MKNITLLFCL FLANILLGAC SGGEDEKKEM DEGKGAYALF LKKSITVSTG ESQTDVVVEW AKTSWEITLG EGDIVKSVTP TSGGSNTGEK QYTKVRVSCG ANSTMKKRTQ TIHLFDKTNE TTVDLLVEQE PPFKSVTLTV DPSVKYQPVV GFGGMYNPKI WCGDNLISAS QLDKMYGAGG LGYSILRLMI YPNESDWSAD VEAAKAAQAN GAIIFACPWD CTDALADKIT VNGKEMKHLK KENYEAYANH LIRYVTFMKE KGVNLYAISV QNEPDMEFTY WTPSEVVDFV KQYGARIRET GVKLMSPEAC GMQPEYTDPI INNAEAFAQT DILAGHLYQG FTDLSSGYVK NRHDYICGVY SRIQGKTWWM TEHLFNDGEN SDDSSKWEFL KWQYSLNHLG KEIHMCMEGY CSAYIYWYLK RFYGLMGDTD KRSPTSEGEI TKNGYIMAHY AQYATETTRI KVVTNNEEVC ATAYWDEKTG EVTIVLLNLN GASQWLEIPL AGIKKASAVE TNETKNMEVI DTGLMESAEG ITVLLSANSI TSVRLTF |
| Xyloglucanase: GH5 Xyloglucanase from *Bacteroides oyatus* | 8 | MEKQSFSDGL FSPLGIKRVI FMLVLLTTSF ISCSNSDEKG GSLEVAQEYR NLEFDARGSR QTIQIDPAE WHISTSESWC KSSHTIGEGK QYVNITVEAN DTQKERTATV TVSASGAPDI IINVKQSLYS VPAYDEYIAP DNTGMRDLTS MQLSALMKAG VNVGNTFEAV IVGNDGSLSG DETCWGNPTP NKVLFEGIKA AGFDVVRIPV AYSHQFEDAA TYKIKSAWMD KVEAAVKAAL DAGLYVIINI HWEGGWLNHP VDANKEALDE RLEAMWKQIA LRFRDYDDRL LFAGTNEVNN DDANGAQPTE ENYRVQNGFN QVFVNTVRAT GGRNHYRHLI VQAYNTDVAK AVAHFTMPLD IVQNRIFLEC HYYDPYDFTI MPNDENFKSQ WGAAFAGGDV SATGQEGDIE ATLSSLNVFI NNNVPVIIGE YGPTLRDQLT GEALENHLKS RNDYIEYVVK TCVKNKLVPL YWDAGYTEKL FDRTTGQPHN AASIAAIMKG LN |

TABLE 4-continued

Sequence listings

| Name | SEQ ID | Sequence |
|---|---|---|
| Xyloglucanase: GH74 Xyloglucanase from *Trichoderma reesei* | 9 | MKVSRVLALV LGAVIPAHAA FSWKNVKLGG GGGFVPGIIF HPKTKGVAYA RTDIGGLYRL<br>NADDSWTAVT DGIADNAGWH NWGIDAVALD PQDDQKVYAA VGMYTNSWDP SNGAIIRSSD<br>RGATWSFTNL PFKVGGNMPG RGAGERLAVD PANSNIIYFG ARSGNGLWKS TDGGVTFSKV<br>SSFTATGTYI PDPSDSNGYN SDKQGLMWVT FDSTSSTTGG ATSRIFVGTA DNITASVYVS<br>TNAGSTWSAV PGQPGKYFPH KAKLQPAEKA LYLTYSDGTG PYDGTLGSVW RYDIAGGTWK<br>DITPVSGSDL YFGFGGLGLD LQKPGTLVVA SLNSWWPDAQ LFRSTDSGTT WSPIWAWASY<br>PTETYYYSIS TPKAPWIKNN FIDVTSESPS DGLIKRLGWM IESLEIDPTD SNHWLYGTGM<br>TIFGGHDLTN WDTRHNVSIQ SLADGIEEFS VQDLASAPGG SELLAAVGDD NGFTFASRND<br>LGTSPQTVWA TPTWATSTSV DYAGNSVKSV VRVGNTAGTQ QVAISSDGGA TWSIDYAADT<br>SMNGGTVAYS ADGDTILWST ASSGVQRSQF QGSFASVSSL PAGAVIASDK KTNSVFYAGS<br>GSTFYVSKDT GSSFTRGPKL GSAGTIRDIA AHPTTAGTLY VSTDVGIFRS TDSGTTFGQV<br>STALTNTYQI ALGVGSGSNW NLYAFGTGPS GARLYASGDS GASWTDIQGS QGFGSIDSTK<br>VAGSGSTAGQ VYVGTNGRGV FYAQGTVGGG TGGTSSSTKQ SSSSTSSASS STTLRSSVVS<br>TTRASTVTSS RTSSAAGPTG SGVAGHYAQC GGIGWTGPTQ CVAPYVCQKQ NDYYYQCV |
| Cellobiohydrolase: GH7 Cel7A cellobiohydrolase from *Trichoderma reesei* | 10 | MYRKLAVISA FLATARAQSA CTLQSETHPP LTWQKCSSGG TCTQQTGSVV IDANWRWTHA<br>TNSSTNCYDG NTWSSTLCPD NETCAKNCCL DGAAYASTYG VTTSGNSLSI GFVTQSAQKN<br>VGARLYLMAS DTTYQEFTLL GNEFSFDVDV SQLPCGLNGA LYFVSMDADG GVSKYPTNTA<br>GAKYGTGYCD SQCPRDLKFI NGQANVEGWE PSSNNANTGI GGHGSCCSEM DIWEANSISE<br>ALTPHPCTTV GQEICEGDGC GGTYSDNRYG GTCDPDGCDW NPYRLGNTSF YGPGSSFTLD<br>TTKKLTVVTQ FETSGAINRY YVQNGVTFQQ PNAELGSYSG NELNDDYCTA EEAEFGGSSF<br>SDKGGLTQFK KATSGGMVLV MSLWDDYYAN MLWLDSTYPT NETSSTPGAV RGSCSTSSGV<br>PAQVESQSPN AKVTFSNIKF GPIGSTGNPS GGNPPGGNRG TTTTRRPATT TGSSPGPTQS<br>HYGQCGGIGY SGPTVCASGT TCQVLNPYYS QCL |
| Cellobiohydrolase: GH6 Cel6A cellobiohydrolase from *Trichoderma reesei* | 11 | MIVGILTTLA TLATLAASVP LEERQACSSV WGQCGGQNWS GPTCCASGST CVYSNDYYSQ<br>CLPGAASSSS STRAASTTSR VSPTTSRSSS ATPPPGSTTT RVPPVGSGTA TYSGNPFVGV<br>TPWANAYYAS EVSSLAIPSL TGAMATAAAA VAKVPSFMWL DTLDKTPLME QTLADIRTAN<br>KNGGNYAGQF VVYDLPDRDC AALASNGEYS IADGGVAKYK NYIDTIRQIV VEYSDIRTLL<br>VIEPDSLANL VTNLGTPKCA NAQSAYLECI NYAVTQLNLP NVAMYLDAGH AGWLGWPANQ<br>DPAAQLFANV YKNASSPRAL RGLATNVANY NGWNITSPPS YTQGNAVYNE KLYIHAIGPL<br>LANHGWSNAF FITDQGRSGK QPTGQQQWGD WCNVIGTGFG IRPSANTGDS LLDSFVWVKP<br>GGECDGTSDS SAPRFDSHCA LPDALQPAPQ AGAWFQAYFV QLLTNANPSF L |
| Endoglucanase A eglA- *Aspergillus niger* GH12 | 12 | MKLPVTLAML AATAMGQTMC SQYDSASSPP YSVNQNLWGE YQGTGSQCVY VDKLSSSGAS<br>WHTEWTWSGG EGTVKSYSNS GVTFNKKLVS DVSSIPTSVE WKQDNTNVNA DVAYDLFTAA<br>NVDHATSSGD YELMIWLARY GNIQPIGKQI ATATVGGKSW EVWYGSTTQA GAEQRTYSFV<br>SESPINSYSG DINAFFSYLT QNQGFPASSQ YLINLQFGTE AFTGGPATFT VDNWTASVN |
| *Aspergillus niger* Endo-β-1,4-glucanase GH5, CBM1 | 13 | MRISNLIVAA SAASMVSALP SRQMKKRDSG FKWVGTSESG AEFGSALPGT LGTDYTWPET<br>SKIQVLRNKG MNIFRIPFLM ERLTPDGLTS SFASTYLSDL KSTVEFVTNS GAYAVLDPHN<br>YGRPFDGSIIT STSDFKTWWK NVATEFADND KVIFDTNNEY HDMEQSLVLD LNQAAINGIR<br>AAGATTQYIF VEGNAYTGAW DWTTYNDNLS GLTDSEDKII YEMHQYLDSD SSGTSETCVS<br>STIGQERLEK ATEWLKTNNK QGIVGEFAGY VNSVCEEAVE GMLAYMSENS DVWVGASWWS<br>AGPWWGTYMY SLEPTDGTAY STYLPILEKY FPSGDASASS SASVSVAAAT STASTTTAAF<br>EQTTTPATQG PSATNSAGEV NQYYQCGGIN WTGPTVCASP YTCKVQNDYY YQCVAE |
| *Aspergillus niger* Endo-β-1,4-glucanase B GH5 | 14 | MKFQSTLLLA AAAGSALAVP HGSGHKKRAS VFEWFGSNES GAEFGTNIPG VWGTDYIFPD<br>PSTISTLIGK GMNFFRVQFM MERLLPDSMT GSYDEEYLAN LTINVKAVTD GGAHALIDPH<br>NYGRYNGEII SSTSDFQTFW QNLAGOYKDN DLVMFDTNNE YYDMDQDLVL NLNQAAINGI<br>RAAGASQYIF VEGNSWTGAW TWVDVNDNMK NLTDPEDKIV YEMHQYLDSD GSGTSETCVS<br>GTIGKERITD ATQWLKDNKK VGFIGEYAGG SNDVCRSAVS GMLEYMANNT DVWKGASWWA<br>AGPWWGDYIF SLEPPDGTAY TGMLDILETY L |
| GH30 Xylanase from *Trichoderma reesei* | 15 | MKSSISVVLA LLGHSAAWSY ATKSQYRANI KINARQTYQT MIGGGCSGAF GIACQQFGSS<br>GLSPENQQKV TQILFDENIG GLSIVRNDIG SSPGTTILPT CPATPQDKFD YVWDGSDNCQ<br>FNLTKTALKY NPNLYVYADA WSAPGCMKTV GTENLGGQIC GVRGTDCKHD WRQAYADYLV<br>QYVRFYKEEG IDISLLGAWN EPDFNPFTYE SMLSDGYQAK DFLEVLYPTL KKAFPKVDVS<br>CCDATGARQE RNILYELQQA GGERYFDIAT WHNYQSNPER PFNAGGKPNI QTEWADGTGP<br>WNSTWDYSGQ LAEGLQWALY MHNAFVNSDT SGYTHWWCAQ NTNGDNALIR LDRDSYEVSA<br>RLWAFAQYFR FARPGSVRIG ATSDVENVYV TAYVNKNGTV AIPVINAAHP PYDLTIDLEG<br>42 IKKRKLSEYL TDNSHNVTLQ SRYKVSGSSL KVTVEPRAMK TFWLE |
| *Aspergillus niger* Endo-β-1,4-xylanase 1 GH11 | 16 | MKVTAAFAGL LVTAFAAPVP EPVLVSRSAG INYVQNYNGN LGDFTYDESA GTFSMYWEDG<br>VSSDFVVGLG WTTGSSKAIT YSAEYSASGS SSYLAVYGWV NYPQAEYYIV EDYGDYNPCS<br>SATSLGTVYS DGSTYQVCTD TRTNEPSITG TSTFTQYFSV RESTRTSGTV TVANHFNFWA<br>QHGFGNSDFN YQVMAVEAWS GAGSASVTIS S |
| GH5 mannanase from *Trichoderma reesei* | 17 | MMMLSKSLLS AATAASALAA VLQPVPRASS FVTISGTQFN IDGKVGYFAG TNCYWCSFLT<br>NHADVDSTFS HISSSGLKVV RVWGFNDVNT QPSPGQIWFQ KLSATGSTIN TGADGLQTLD<br>YVVQSAEQHN LKLIIPFVNN WSDYGGINAY VNAFGGNATT WYTNTAAQTQ YRKYVQAVVS<br>RYANSTAIFA WELGNEPRCN GCSTDVIVQW ATSVSQYVKS LDSNHLVTLG DEGLGLSTGD<br>GAYPYTYGEG TDPAKNVQ1K SLDFGTFHLY PDSWGTNYTW GNGWIQTHAA ACLAAGKPCV<br>FEEYGAQQNP CTNEAPWQTT SLTTRGMGGD MFWQGWGDTFA NGAQSNSDPY TVWYNSSNWQ |

TABLE 4-continued

Sequence listings

| Name | SEQ ID | Sequence |
|---|---|---|
| | | CLVKNHVDAI NGGTTTPPPV SSTTTTSSRT SSTPPPPGGS CSPLYGQCGG SGYTGPTCCA QGTCIYSNYW YSQCLNT |
| Aspergillus niger Endo-β-1,4-mannanase GH26 | 18 | MFAKLSLLSL LFSSAALGAS NQTLSYGNID KSATPEARAL LKYIQLQYGS HYISGQQDID SWNNWVEKNIG VAPAILGSDF TYYSPSAVAH GGKSHAVEDV IQHAGRNGIN ALVWHWYAPT CLLDTAKEPW YKGFYTEATC FNVSEAVNDH GNGTNYKLLL RDIDAIAAQI KRLDQAKVPI LFRPLHEPEG GWFWWGAQGP APFKKLWDIL YDRITRYHNL HNMVWVCNTA DPAWYPGNDK CDIATIDHYP AVGDHGVAAD QYKKLQTVTN NERVLAMAEV GPIPDPDKQA RENVNWAYWM VWSGDFIEDG KQNPNQFLHK VYNDTRVVAL NWEGA |
| Aspergillus niger β-mannanase GH5 | 19 | MKLSNALLTL ASLALANVST ALPKASPAPS TSSSAASTSF ASTSGLQFTI DGETGYFAGT NSYWIGFLTD NADVDLVMGH LKSSGLKILR VWGFNDVTSQ PSSGTVWYQL HQDGKSTINT GADGLQRLDY VVSSAEQHDI KLIINFVNYW TDYGGMSAYV SAYGGSGETD FYTSDTMQSA YQTYIKTVVE RYSNSSAVFA WELANEPRCP SCDTSVLYNW IEKTSKFIKG LDADRMVCIG DEGFGLNIDS DGSYPYQFSE GLNFTMNLGI DTIDFGTLHL YPDSWGTSDD WGNGWITAHG AACKAAGKPC LLEEYGVTSN HCSVEGSWQK TALSTTGVGA DLFWQYGDDL STGKSPDDGN TIYYGTSDYQ CLVTDHVAAI GSA |
| Aspergillus niger Cellobiohydrolase A GH7 | 20 | MHQRALLFSA LLTAVRAQQA GTLTEEVHPS LTWQKCTSEG SCTEQSGSVV IDSNWRWTHS VNDSTNCYTG NTWDATLCPD DETCAANCAL DGADYESTYG VTTDGDSLTL KFVTGSNVGS RLYLMDTSDE GYQTFNLLDA EFTFDVDVSN LPCGLNGALY FTAMDADGGV SKYPANKAGA KYGTGYCDSQ CPRDLKFIDG QANVDGWEPS SNNDNTGIGN HGSCCPEMDI WEANKISTAL TPHPCDSSEQ TMCEGNDCGG TYSDDRYGGT CDPDGCDFNP YRMGNDSFYG PGKTIDTGSK MTVVTQFITD GSGSLSEIKR YYVQNGNVIA NADSNISGVT GNSITTDFCT AQKKAFGDED IFAEHNGLAG ISDAMSSMVL ILSLWDDYYA SMEWLDSDYP ENATATDPGV ARGTCDSESG VPATVEGAHP DSSVTFSNIK FGPINSTFSA SA |
| Aspergillus niger Cellobiohydrolase B GH7, CBM1 | 21 | MSSFQIYRAA LLLSILATAN AQQVGTYTTE THPSLTWQTC TSDGSCTTND GEVVIDANWR WVHSTSSATN CYTGNEWDTS ICTDDVTCAA NCALDGATYE ATYGVTTSGS ELRLNFVTQG SSKNIGSRLY LMSDDSNYEL FKLLGQEFTF DVDVSNLPCG LNGALYFVAM DADGGTSEYS GNKAGAKYGT GYCDSQCPRD LKFINGEANC DGWEPSSNNV NTGVGDHGSC CAEMDVWEAN SISNAFTAHP CDSVSQTMCD GDSCGGTYSA SGDRYSGTCD PDGCDYNPYR LGNTDFYGPG LTVDTNSPFT VVQTFITDDG TSSGTLTEIK RLYVQNGEVI ANGASTYSSV NGSSITSAFC ESEKTLFGDE NVFDKHGGLE GMGEAMAKGM VLVLSLWDDY AADMLWLDSD YPVNSSASTP GVARGTCSTD SGVPATVEAE SPNAYVTYSN IKFGPIGSTY SSGSSSGSGS SSSSSSTTTK ATSTTLKTTS TTSSGSSSTS AAQAYGQCGG QGWTGPTTCV SGYTCTYENA YYSQCL |
| GH3 beta-glucosidase from Trichoderma reesei | 22 | MRYRTAAALA LATGPFARAD SHSTSGASAE AVVPPAGTPW GTAYDKAKAA LAKLNLQDKV GIVSGVGWNG GPCVGNTSPA SKISYPSLCL QDGPLGVRYS TGSTAFTPGV QAASTWDVNL IRERGQFIGE EVKASGIHVI LGPVAGPLGK TPQGGRNWEG FGVDPYLTGI AMGQTINGIQ SVGVQATAKH YILNEQELNR ETISSNPDDR TLHELYTWPF ADAVQANVAS VMCSYNKVNT TWACEDQYTL QTVLKDQLGF PGYVMTDWNA QHTTVQSANS GLDMSMPGTD FNGNNRLWGP ALTNAVNSNQ VPTSRVDDMV TRILAAWYLT GQDQAGYPSF NISRNVQGNH KTNVRAIARD GIVLLKNDAN ILPLKKPASI AVVGSAAIIG NHARNSPSCN DKGCDDGALG MGWGSGAVNY PYFVAPYDAI NTRASSQGTQ VTLSNTDNTS SGASAARGKD VAIVFITADS GEGYITVEGN AGDRNNLDPW HNGNALVQAV AGANSNVIVV VHSVGAIILE QILALPQVKA VVWAGLPSQE SGNALVDVLW GDVSPSGKLV YTIAKSPNDY NTRIVSGGSD SFSEGLFIDY KHFDDANITP RYEFGYGLSY TKFNYSRLSV LSTAKSGPAT GAVVPGGPSD LFQNVATVTV DIANSGQVTG AEVAQLYITY PSSAPRTPPK QLRGFAKLNL TPGQSGTATF NIRRRDLSYW DTASQKWVVP SGSFGISVGA SSRDIRLTST LSVA |
| Beta-xylosidase from Trichoderma reesei | 23 | MVNNAALLAA LSALLPTALA QNNQTYANYS AQGQPDLYPE TLATLTLSFP DCEHGPLKNN LVCDSSAGYV ERAQALISLF TLEELILNTQ NSGPGVPRTG LPNYQVWNEA LHGLDRANFA TKGGQFEWAT SFPMPILTTA ALNRTLIHQI ADIISTQARA FSNSNGRYGLD VYAPNVNGFR SPLWGRGQET PGEDAFFLSS AYTYEYITGI QGGVDPEHLK VAATVKHFAG YDLENWNNQS RLGFDAIITQ QDLSEYYTPQ FLAAARYAKS RSLMCAYNSV NGVPSCANSF FLQTLLRESW GFPEWGYVSS DCDAVYNVFN PHDYASNQSS AAASSLRAGT DIDCGQTYPW BLNESEVAGE VSRGEIERSV TRLYANLVRL GYFDKKNQYR SLGWKDVVKT DAWNISYEAA VEGIVLLKND GTLPLSKKVR SIALIGPWAN ATTQMQGNYY GPAPYLISPL EAAKKAGYHV NFELGTEIAG NSTTGFAKAI AAAKKSDAII YLGGIDNTIE QEGADRTDIA WPGNQLDLIK QLSEVGKPLV VLQMGGGQVD SSSLKSNKKV NSLVWGGYPG QSGGVALFDI LSGKRAPAGR LVTTQYPAEY VHQFPQNDMN LRPDGKSNPG QTYIWYTGKP VYEFGSGLFY TTFKETLASH PKSLKFNTSS ILSAPHPGYT YSEQIPVETF EANIKNSGKT ESPYTAMLFV RTSNAGPAPY PNKWLVGFDR LADIKPGHSS KLSIPIPVSA LARVDSHGNR IVYPGKYELA LNTDESVKLE FELVGEEVTI ENWPLEEQQI KDATPDA |
| Beta-mannosidase from Trichoderma reesei | 24 | MARHSIQLDK GWTFRQHQGS SPEWLPVEKV PTQVHMDLLA NKQIPDPFVD LNERAVQWIG YKDWEYQVTF TPEAAQVEDA TRDLVFNGLD TFATVYLNEA KILEAENMFV SYRVNVTDRI KASSENTLRI VFHSAIVRGE EL1KEHPEHN FLVRQTERSR VPVRKAQYNW GWDWGPILMT AGPMKPVALE TYVARIDDVW AQSDVSQDDL TVSGIIFARV AGRPSQDDQV SLTLSLDGKA VFQQTVDVAS AKDGLIKVPF KLEDPKLWYP RGYGSQPRYQ LNADLARKAS DASQIDSLSK LVGFRRAELV QEPDAFGKSF YFPRINNVDVF AGGSCWIPAD SYLAGVPPER YHAWAKLIAD GNQVMLRVWG GGVYEEDALI EACDELGILV FHDFQFACAS YPAYPSYLEN LEVEARQQIR RLRTHPSVII WAGNNEDYQV QERYKLDYEF ENKDPESWLK SSFPARYIYE BFLPKLVEEE DPGKIYHPSS PWGDGKPTAD PTVGDIHQWN XPPPPISTQI THTQHPTDHP LHTVWHGTMN |

TABLE 4-continued

Sequence listings

| Name | SEQ ID | Sequence |
|---|---|---|
| | | KYQEAVNMGG RFVSEFGMEA YPHLSTTRRM ASDPAQLYPG SMVLDAHNKA IGHERRMMSY |
| | | VVDNFRPRHD LGGYTHLTQV VQSETMRAAY KAWRRQWGKP GARRCGGALV WQLNDCWPTM |
| | | SWAVVDYRLV KKPAYYAIAR ALRRVDVGVC RTWHDWTQTG AWVDENSGLV TGQVDHTLAA |
| | | REGTFDVWVV SSDTQPVALD LVVRFISVRT GRDVVDPILH SRVVAAANSA TDILQGKTLP |
| | | PSIPNPEDIT KPPPLAEYDP YVVHATITDA ATGTVIAADT AWPEPIKYLD LSDRGIAFEV |
| | | SSAGDEVVVS AEKPVKGFVF EEVEGLELSD NGFDVVPGEK QLVKVGGALK AGELLWTCIG |
| | | ADSASLKIEA SSSLAPR |
| AA9 LPMO from *Trichoderma reesei* | 25 | MIQKLSNLLV TALAVATGVV GHGHINDIVI NGVWYQAYDP TTFPYESNPP IVVGWTAADL |
| | | DNGFVSPDAY QNPDIICHKN ATNAKGHASV KAGDTILFQW VPVPWPHPGP IVDYLANCNG |
| | | DCETVDKTTL EFFKIDGVGL LSGGDPGTWA SDVLISNNNT WVVKIPDNLA PGNYVLRHEI |
| | | IALHSAGQAN GAQNYPQCFN IAVSGSGSLQ PSGVLGTDLY HATDPGVLIN IYTSPLNYII |
| | | PGPTVVSGLP TSVAQGSSAA TATASATVPG GGSGPTSRTT TTARTTQASS RPSSTPPATT |
| | | SAPAGGPTQT LYGQCGGSGY SGPTRCAPPA TCSTLNPYYA QCLN |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition for use in consumer products, comprising at least 50% by dry weight saccharides, wherein the saccharides comprise:
   i) less than 50% by dry weight disaccharides, wherein at least 20% by dry weight of the disaccharides comprise cellobiose;
   ii) greater than 5% by dry weight trisaccharides;
   iii) greater than 2% by dry weight tetrasaccharides; and
   iv) unbranched and branched oligosaccharides in a ratio of at least 1:1 by dry weight.

2. The composition of claim 1, wherein the saccharides further comprise insoluble polysaccharides.

3. The composition of claim 1, wherein the saccharides comprise from 5-50% by dry weight polysaccharides.

4. The composition of claim 1, wherein the saccharides comprise cello-oligosaccharides with a DP of 2-6 and xylo-oligosaccharides in a ratio of between 1:9 and 9:1, by dry weight.

5. The composition of claim 3, wherein the source of the polysaccharides is a biomass.

6. The composition of claim 5, wherein the biomass comprises corn stover, corn cob, wheat bran, wheat straw, hardwood, softwood, cellulose, chitin, chitosan, xylan, xyloglucan, mixed-linkage glucan, mannan, lignocellulose, or a combination thereof.

7. The composition of claim 1, wherein the saccharides comprise at least three different types of oligosaccharide.

8. The composition of claim 1, wherein a solubility of the composition in water is greater w/w when compared to a composition comprising only cello-oligosaccharides with a degree of polymerization from two to six.

9. The composition of claim 1, wherein the composition comprises less than 5% monosaccharides w/w.

10. The composition of claim 1, wherein the composition is a hygroscopicity modulator.

11. The composition of claim 1, wherein the composition has a comparable hygroscopicity to, or greater hygroscopicity than, an identical amount of a control composition wherein the control composition comprises primarily monosaccharides and/or disaccharides.

12. The composition of claim 1 wherein the composition is included at 1% w/w or more of a consumer product.

13. The composition of claim 12, wherein the consumer product is a cosmetic product.

14. The composition of claim 13, wherein the cosmetic product is a mascara, a foundation, a lip gloss, an eyeshadow, an eyeliner, a primer, a lipstick blush, a nail polish, a bronzer, a makeup, a shampoo, a conditioner, a styling mousse, a styling gel, a hairspray, a hair dye, a hair wax, a moisturizer, a exfoliant, a sun cream, a cleanser, a toothpaste, a cream, a lotion, an ointment, or a face mask.

15. The composition of claim 12, wherein the consumer product is a nutraceutical product.

16. The composition of claim 15, wherein the nutraceutical product is a probiotic formulation or a prebiotic formulation.

17. The composition of claim 12, wherein the consumer product is a binding product.

18. The composition of claim 12, wherein consumer product comprises 1-30% by dry weight of polysaccharides.

19. The composition of claim 12, wherein the the composition comprises a phenolic compound, a portion of lignin, and/or a product of lignin breakdown.

20. The composition of claim 1, wherein the composition is a raw material for processing to a further composition.

* * * * *